US006946255B1

(12) United States Patent
Kayagaki et al.

(10) Patent No.: US 6,946,255 B1
(45) Date of Patent: *Sep. 20, 2005

(54) MONOCLONAL ANTIBODY REACTING SPECIFICALLY REACTING WITH FAS LIGAND AND PRODUCTION PROCESS THEREOF

(75) Inventors: Nobuhiko Kayagaki, Tokyo (JP); Hideo Yagita, Tokyo (JP); Ko Okumura, Tokyo (JP); Motomi Nakata, Kanagawa (JP)

(73) Assignee: Ko Okumura, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 08/913,555

(22) PCT Filed: Mar. 21, 1996

(86) PCT No.: PCT/JP96/00734

§ 371 (c)(1),
(2), (4) Date: Sep. 17, 1997

(87) PCT Pub. No.: WO96/29350

PCT Pub. Date: Sep. 26, 1996

(30) Foreign Application Priority Data

Mar. 20, 1995 (JP) ............................................. 7/087420
Oct. 27, 1995 (JP) ............................................. 7/303492

(51) Int. Cl.$^7$ ......................... G01N 33/53; C12P 21/08; C07K 16/28; C07K 21/08
(52) U.S. Cl. ..................... 435/7.1; 435/70.21; 435/810; 530/388.15; 530/388.2; 530/391.2; 530/391.3
(58) Field of Search .................. 530/388.15, 388.2, 530/391.1, 391.3, 387.7; 435/70.21, 810, 7.1, 7.94, 7.95, 7.5; 424/138.1

(56) References Cited

U.S. PATENT DOCUMENTS 4,950,588 A * 8/1990 Dattagupta et al.

FOREIGN PATENT DOCUMENTS

WO     WO95/18819     7/1995
WO     WO 95/27735     10/1995

OTHER PUBLICATIONS

Stryer et al, in Biochemistry, Third edition, W H Freeman Company, New York, pp. 31–33, 1998.*
Kuby et al., 1994, Immunology, second edition, pp. 85–96.*
Abaza et al, J of Protein Chemistry 11(5): 433–444, 1992.*
Ngo et al., 1994, The Protein Folding Problem and Tertiary Structure Prediction, pp. 492–495.*
Harlow et al, in Antibodies a Laboratory Manual, 1988, Cold Spring harbor laboratory publication, Cold Spring Harbor, NY, pag chapter 6, pp. 155–149, 296–297, 340–341 and 626–629.*
Campbell et al (in Monoclonal Antibody Technology, 1984, Elsevier Science Publisher, New York, NY, p. 1–32.*

Suda et al, Cell 75: 1169–78, Dec. 1993.*
Takahashi et al, International Immunology 6(10): 1567–74, Jun. 1994.*
Harlow, E. and Lane, D, Antibodies: A Laboratory Manual. Cold Spring Harbor Laboratory Press, pp. 555–612, 1988.*
Goding, JW, Monoclonal Antibodies: Principles and Practice. Academic Press, New York, pp. 5–58, 1986.*
Smith, JA, Current Protocols in Molecular Biology, Ausubel, et al., eds., Green Pub. Assn & Wiley Intersciences, pp. 11.0.1–11.16.13, 1992.*
"Expression of the functional soluble form of human Fas ligand in activated lymphocytes", Tanaka et al., The EMBO Journal, vol. 14, No. 6, pp. 1129–1135, Mar. 15, 1995.
"The Fas Death Factor", Nagata et al., Science, vol. 267, No. 5203, pp. 1449–1456, Mar. 10, 1995.
"Role of Fas Ligand in Apoptosis Induced by Hepatitis C Virus Infection", Mita et al., Biochemical and Biophysical Research Communication, vol. 204, No. 2, pp. 468–474, Oct. 28, 1994.
"Continuous cultures of fused cells secreting antibody of predefined specificity", Köhler, et al. Nature, vol. 256, pp. 495–497, Aug. 7, 1995.
"Metalloproteinase–mediated Release of Human Fas Ligand", Kayagaki et al., J. Exp. Med., vol. 182, pp. 1777–1783, Dec. 1995.
Takashi Suda et al. *The Structure and the Function of the Fas Ligand, Abstract of Cell Technology,* 13(8), 738–744 (1994).
Takahashi, T. et al. "Human Fas ligand: gene structure, chromosomal location and species specificity", International Immunology (1994) vol. 6, No. 10, P. 1567–1574.
Takahashi, T. et al. "Generalized lymphoproliferative disease in mice, caused by a point mutation in the Fas ligand", Cell (1994) vol. 76, P. 969–976.
Suda, T. et al. "Purification and characterization of the Fas–ligand that induces apoptosis", J. Exp. Med. (1994) vol. 179, No. 3, p. 873–879.
Nobuyuki Kobayashi, et al., *Anti–Fas Monoclonal Antibody is Cytocidal to Human Immunodeficiency Virus–Infected Cells Without Augmenting Viral Replication,* vol. 87. pp. 9620–9624 Dec. 1990.
Jun Ogasawara et al. *Lethal Effect of the Anti–Fas Antibody in Mice* vol. 364 Aug. 26, 1993.

(Continued)

*Primary Examiner*—Christina Chan
*Assistant Examiner*—Phuong Huynh
(74) *Attorney, Agent, or Firm*—McDermott Will & Emery LLP

(57) ABSTRACT

The invention provides monoclonal antibodies, which specifically react with a Fas ligand, or active fragments thereof, a production process of the monoclonal antibodies, which specifically react with a Fas ligand, hybridomas separately producing a monoclonal antibody, which specifically reacts with a Fas ligand present on a cell surface, a method of detecting a Fas ligand in a solution, and a kit for use in detecting a Fas ligand, comprising plurality of monoclonal antibodies against Fas ligand in combination.

15 Claims, 14 Drawing Sheets

OTHER PUBLICATIONS

Naoki Hiramatsu et al. *Immunohistochemical Detection of Fas Antigen in Liver Tissue of Patients With Chronic Hepatitis C,* vol. 19, 1994 1354–1359.

Shino Hanabuchi et al. *Fas and its Ligand in a General Mechanism of T–Cell Mediated Cytotoxicity,* vol. 91, pp. 4930–4934, May 1994.

Rie Watanabe–Fukunaga et al. *Lymphoproliferation Disorder in Mice Explained by Defects in Fas Antigen That Mediates Apoptosis.*

Naoto Itoh et al. *The Polypeptide Encoded by the CDNA for Human Cell Surface Antigen Fas can Mediate Apoptosis,* Cell vol. 66, 233–234, Jul. 26, 1991.

Takashi Suda et al. *Molecular Cloning and Expression of the Fas Ligand, a Novel Member of the Tumor Necrosis Factor Family,* vol. 75–1169–1178, Dec. 17, 1993, Cell.

* cited by examiner

Fig. 13

```
                          CDR1        CDR2
NOK1VH .amino  1:VQLQESGPELVKPGASVKISCKASGYAF--SSSWMNWVKQRPGKGLEWIGRIYPGDGDTN  58
NOK2VH .amino  1:VQLQQSGAELVRPGTSVKMSCKAAGYTF--TNYWIGWVKQRPGHGLEWIGYLYPGGLYTN  58
NOK3VH .amino  1:VKLQESGPELVKPGASVKISCKASGYAF--SSSWMNWVKQRPGKGLEWIGRIYPVNGDTN  58
NOK4VH .amino  1:VQLQESGPGLVKPSQSLSLTCSVTGYSITSGYYW-NWIRQFPGNKLEWMG-YISYDGSNN  58
NOK5VH .amino  1:VQLQESGAEPAKPGASVKMSCKASGYTF--TTYWMHWVKQRPGQGLEWIGYINPSSGYTE  58
               * ** **     *  *    *   **     *  *  * **  *** *
                                                        CDR3
NOK1VH .amino  59:DNGKFKGKATLTADKSSSTAYMQLSSLTSEDSAVYFCARSYYYDGSPW-FTYWGQGTTVT 117
NOK2VH .amino  59:YNEKFKGKATLTADTSSSTAYMQLSSLTSEDSAIYYCARYRDYD-YAMDY--WGQGTTVT 115
NOK3VH .amino  59:YNGKFKGKATLTADKSSSTAYMQLSSLTSEDSAVYFCA-T---DGY-WYFDVWGQGTTVT 113
NOK4VH .amino  59:YNPSLKNRISITRDTSKNQFFLKLNSVTTEDTATYYCA-VYYYDG--SSFDYWGQGTTVT 115
NOK5VH .amino  59:YNQKFKDKATLTADKSSSTAYMQLISLTSEDSAVYYCARRGNY--YYFDY--WGQGTTVT 114
                  *   *       * * *      * * * ** * ** **         *******

NOK1VH .amino  118:VSS                                                        120
NOK2VH .amino  116:VSS                                                        118
NOK3VH .amino  114:VSS                                                        116
NOK4VH .amino  116:VSS                                                        118
NOK5VH .amino  115:VSS                                                        117
                   ***
```

Fig. 14

```
                           CDR1                         CDR2
NOK1VL.amino  1:DIQMTQSPSSLSASLGDRVTISCRASQDISNY-----LNWYQQKPDGTVKLLIYYTSRLH   55
NOK2VL.amino  1:DVLMTQTPLSLPVNIGDQASISCKSTKSLLNSDGFTYLGWCLQKPGQSPQLLIYLVSNRF   60
NOK4VL.amino  1:DIVLTQSPASLAVSLRQRATISCRASEGVDSY-GISFMHWYQQKPGQPPKLLIYRASYLK   59
NOK5VL.amino  1:DVLMTQTPKFLPVSAGDRVTMTCKASQS-V---G-NNVAWYQQKPGQSPKLLIYYTSNRY   55
                * ** *  *              *            *  ***    ****  *
                                                 CDR3
NOK1VL.amino 56:SGVPSRFSGSGSGTDYSLTISNLEPEDIATYFC-QQYSEFPWTFGGGTKLEIKR       108
NOK2VL.amino 61:SGVPDRFSGSGSGTDFTLKISRVEAEDLGVYYCFQSNY-LPLTFGSTKLEIKR        113
NOK4VL.amino 60:SGVPARFSGSGSRTDFTLTIDPVEADDAATYYC-QQNNEDPWTFGGGTKLEIKR       112
NOK5VL.amino 56:TGVPDRFTGSGSGTDFTFTISSVQVEDLAVYFC-QQHYSSPYTFGSGTKLE---       105
                *** ** **** **       *     *  * *   *  *** *****
```

Fig. 15

```
                      FR1          CDR1    FR2       CDR2
NOK1VH.amino  1:QVQLQQSGPELVKPGASVKISCKASGYAFSSSWMNWVKQRPGKGLEWIGRIYPGDGDTND   60
NOK2VH.amino  1:QVHLQQSGAELVRPGTSVKMSCKAAGYTFTNYWIGWVKQRPGHGLEWIGYLYPGGLYTNY   60
NOK3VH.amino  1:QVQLQQSGPELVKPGASVKISCKASGYAFSSSWMNWVKQRPGKGLEWIGRIYPVNGDTNY   60

FR3               CDR3           FR4
NOK1VH.amino 61:NGKFKGKATLTADKSSSTAYMQLSSLTSEDSAVYFCARSYYYDGSPW-FTYWGQGTLVTVSA  121
NOK2VH.amino 61:NEKFKGKATLTADTSSSTAYMQLSSLTSEDSAIYYCARYRDYD-YAMDY--WGQGTSVTVSS  119
NOK3VH.amino 61:NGKFKGKATLTADKSSSTAYMQLSSLTSEDSAVYFCA-T---DGY-WYFDVWGAGTTVTVSS  117
```

Fig. 16

```
                    FR1                      CDR1          FR2         CDR2
NOK1VL.amino   1:DIQMTQTTSSLSASLGDRVTISC RASQDISNY-----LN WYQQKPDGTVKLLIY YTSRLHS   56
NOK2VL.amino   1:DVVLTQTPLSLPVNIGDQASISC KSTKSLLNSDGFTYLG WCLQKPGQSPQLLIY LVSNRFS   61
NOK3VL.amino   1:NIVMTQSPKSMSMSVGERVTLSC KASENVDIY-----VS WYQQKPEQSPKLLIY GTSNRYT   56

FR3                     CDR3         FR4
NOK1VL.amino  57:GVPSRFSGSGSGTDYSLTISNLEPEDIATYFC QQYSEFPWT FGGGTKLEIKR      108
NOK2VL.amino  62:GVPDRFSGSGSGTDFTLKISRVEAEDLGVYYC FQSNYLPLT FGSGTKLEIKR      113
NOK3VL.amino  57:GVPDRFTGSGSATDFTLTISNVQAEDLSDYYC VQSYSYPWT FGGGTKLEIKR      108
```

Fig. 17

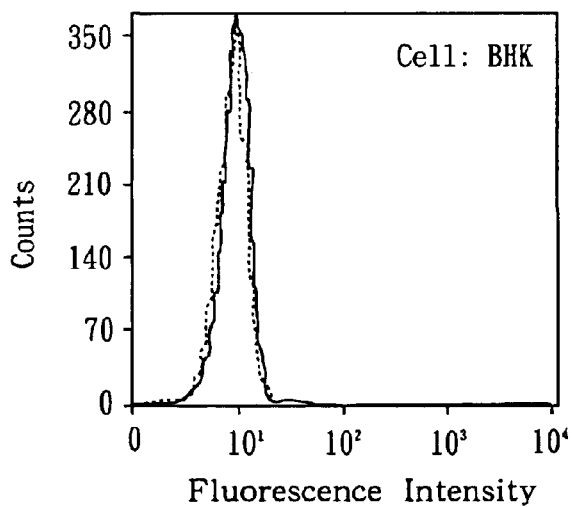

SEQUENCE LISTING (1) GENERAL INFORMATION:

(iii) NUMBER OF SEQUENCES: 31

(2) INFORMATION FOR SEQ ID NO:1:

(i) SEQUENCE CHARACTERISTICS:
       (A) LENGTH: 120 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:1:

Val Gln Leu Gln Glu Ser Gly Pro Glu Leu Val Lys Pro Gly Ala Ser
1               5                   10                  15

```
Val Lys Ile Ser Cys Lys Ala Ser Gly Tyr Ala Phe Ser Ser Trp
            20                  25                  30

Met Asn Trp Val Lys Gln Arg Pro Gly Lys Gly Leu Glu Trp Ile Gly
        35                  40                  45

Arg Ile Tyr Pro Gly Asp Gly Asp Thr Asn Asp Asn Gly Lys Phe Lys
    50                  55                  60

Gly Lys Ala Thr Leu Thr Ala Asp Lys Ser Ser Thr Ala Tyr Met
65                  70                  75                  80

Gln Leu Ser Ser Leu Thr Ser Glu Asp Ser Ala Val Tyr Phe Cys Ala
                85                  90                  95

Arg Ser Tyr Tyr Tyr Asp Gly Ser Pro Trp Phe Thr Tyr Trp Gly Gln
                100                 105                 110

Gly Thr Thr Val Thr Val Ser Ser
            115                 120

(2) INFORMATION FOR SEQ ID NO:2:

(i) SEQUENCE CHARACTERISTICS:
        (A) LENGTH: 360 base pairs
        (B) TYPE: nucleic acid
        (C) STRANDEDNESS: double
        (D) TOPOLOGY: linear (ii) MOLECULE TYPE: cDNA to mRNA (xi) SEQUENCE DESCRIPTION: SEQ ID NO:2:

GTGCAGCTGC AGGAGTCTGG ACCTGAGCTG GTGAAGCCTG GGGCCTCAGT GAAGATTTCC      60

TGCAAGGCTT CTGGCTATGC ATTCAGTAGC TCCTGGATGA ACTGGGTGAA GCAGAGGCCT     120

GGAAAGGGTC TTGAGTGGAT TGGACGAATT TATCCTGGAG ATGGAGATAC TAACGACAAC     180

GGGAAGTTCA AGGGCAAGGC CACACTGACC GCAGACAAAT CCTCCAGCAC AGCCTACATG     240

CAACTCAGCA GTCTGACATC TGAGGACTCT GCGGTCTACT TCTGTGCAAG ATCGTATTAC     300

TACGATGGTA GCCCCTGGTT TACTTACTGG GGCCAAGGGA CCACGGTCAC CGTCTCCTCA     360

(2) INFORMATION FOR SEQ ID NO:3:

(i) SEQUENCE CHARACTERISTICS:
        (A) LENGTH: 108 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

Asp Ile Gln Met Thr Gln Ser Pro Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Pro
65                  70                  75                  80

Glu Asp Ile Ala Thr Tyr Phe Cys Gln Gln Tyr Ser Glu Phe Pro Trp
                85                  90                  95

Thr Phe Gly Gly Gly Thr Lys Leu Glu Ile Lys Arg
```

```
                     100                 105

(2) INFORMATION FOR SEQ ID NO:4:

(i) SEQUENCE CHARACTERISTICS:
        (A) LENGTH: 324 base pairs
        (B) TYPE: nucleic acid
        (C) STRANDEDNESS: double
        (D) TOPOLOGY: linear (ii) MOLECULE TYPE: cDNA to mRNA (xi) SEQUENCE DESCRIPTION: SEQ ID NO:4:

GACATCCAGA TGACGCAGTC TCCATCCTCC CTGTCTGCCT CTCTGGGAGA CAGAGTCACC      60

ATCAGTTGCA GGGCAAGTCA GGATATTAGC AATTATTTAA ACTGGTATCA GCAGAAACCA     120

GATGGAACTG TTAAACTCCT GATCTACTAC ACATCAAGAT TACACTCAGG AGTCCCATCA     180

AGGTTCAGTG GCAGTGGGTC TGGGACAGAT TATTCTCTCA CCATCAGCAA CCTGGAACCT     240

GAAGATATTG CCACTTACTT TTGTCAGCAA TATAGTGAAT TCCGTGGAC GTTCGGTGGA      300

GGCACCAAGC TGGAAATCAA ACGG                                           324

(2) INFORMATION FOR SEQ ID NO:5:

(i) SEQUENCE CHARACTERISTICS:
        (A) LENGTH: 118 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

Val Gln Leu Gln Gln Ser Gly Ala Glu Leu Val Arg Pro Gly Thr Ser
1               5                   10                  15

Val Lys Met Ser Cys Lys Ala Ala Gly Tyr Thr Phe Thr Asn Tyr Trp
            20                  25                  30

Ile Gly Trp Val Lys Gln Arg Pro Gly His Gly Leu Glu Trp Ile Gly
        35                  40                  45

Tyr Leu Tyr Pro Gly Gly Leu Tyr Thr Asn Tyr Asn Glu Lys Phe Lys
    50                  55                  60

Gly Lys Ala Thr Leu Thr Ala Asp Thr Ser Ser Thr Ala Tyr Met
65                  70                  75                  80

Gln Leu Ser Ser Leu Thr Ser Glu Asp Ser Ala Ile Tyr Tyr Cys Ala
                85                  90                  95

Arg Tyr Arg Asp Tyr Asp Tyr Ala Met Asp Tyr Trp Gly Gln Gly Thr
            100                 105                 110

Thr Val Thr Val Ser Ser
        115

(2) INFORMATION FOR SEQ ID NO:6:

(i) SEQUENCE CHARACTERISTICS:
        (A) LENGTH: 354 base pairs
        (B) TYPE: nucleic acid
        (C) STRANDEDNESS: double
        (D) TOPOLOGY: linear (ii) MOLECULE TYPE: cDNA to mRNA (xi) SEQUENCE DESCRIPTION: SEQ ID NO:6:

GTGCAGCTGC AGCAGTCAGG AGCTGAGCTG GTAAGGCCTG GGACTTCAGT GAAGATGTCC      60
```

```
TGCAAGGCTG CTGGATACAC CTTCACTAAC TACTGGATAG GTTGGGTAAA GCAGAGGCCT    120

GGACATGGCC TTGAGTGGAT TGGATATCTT TACCCTGGAG GTCTTTATAC TAACTACAAT    180

GAGAAGTTCA AGGGCAAGGC CACACTGACT GCAGACACAT CCTCCAGCAC AGCCTACATG    240

CAGCTCAGCA GCCTGACATC TGAGGACTCT GCCATCTATT ACTGTGCAAG ATACAGGGAT    300

TACGACTATG CTATGGACTA CTGGGGCCAA GGGACCACGG TCACCGTCTC CTCA          354
```

(2) INFORMATION FOR SEQ ID NO:7:

(i) SEQUENCE CHARACTERISTICS:
        (A) LENGTH: 113 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:7:

```
Asp Val Leu Met Thr Gln Thr Pro Leu Ser Leu Pro Val Asn Ile Gly
1               5                   10                  15

Asp Gln Ala Ser Ile Ser Cys Lys Ser Thr Lys Ser Leu Leu Asn Ser
            20                  25                  30

Asp Gly Phe Thr Tyr Leu Gly Trp Cys Leu Gln Lys Pro Gly Gln Ser
        35                  40                  45

Pro Gln Leu Leu Ile Tyr Leu Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Ser
                85                  90                  95

Asn Tyr Leu Pro Leu Thr Phe Gly Ser Gly Thr Lys Leu Glu Ile Lys
            100                 105                 110

Arg
```

(2) INFORMATION FOR SEQ ID NO:8:

(i) SEQUENCE CHARACTERISTICS:
        (A) LENGTH: 339 base pairs
        (B) TYPE: nucleic acid
        (C) STRANDEDNESS: double
        (D) TOPOLOGY: linear (ii) MOLECULE TYPE: cDNA to mRNA (xi) SEQUENCE DESCRIPTION: SEQ ID NO:8:

```
GATGTTTTGA TGACCCAAAC TCCACTCTCT CTGCCTGTCA ATATTGGAGA TCAAGCCTCT     60

ATCTCTTGCA AGTCTACTAA GAGCCTTCTG AATAGTGATG GATTCACTTA TTTGGGCTGG    120

TGCCTGCAGA AGCCAGGCCA GTCTCCACAG CTCCTAATAT ATTTGGTTTC TAATCGATTT    180

TCTGGAGTTC CAGACAGGTT CAGTGGTAGT GGGTCAGGGA CAGATTTCAC CCTCAAGATC    240

AGCAGAGTGG AGGCTGAGGA TTTGGGAGTT TATTATTGCT TCCAGAGTAA CTATCTTCCT    300

CTTACGTTCG GATCGGGGAC CAAGCTGGAA ATAAAACGG                           339
```

(2) INFORMATION FOR SEQ ID NO:9:

(i) SEQUENCE CHARACTERISTICS:
        (A) LENGTH: 116 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:9:

| | | | | | | | | | | | | | | |
|---|---|---|---|---|---|---|---|---|---|---|---|---|---|---|
| Val | Lys | Leu | Gln | Glu | Ser | Gly | Pro | Glu | Leu | Val | Lys | Pro | Gly | Ala | Ser |
| 1 | | | | 5 | | | | | 10 | | | | | 15 | |

| | | | | | | | | | | | | | | |
|---|---|---|---|---|---|---|---|---|---|---|---|---|---|---|
| Val | Lys | Ile | Ser | Cys | Lys | Ala | Ser | Gly | Tyr | Ala | Phe | Ser | Ser | Ser | Trp |
| | | | 20 | | | | | 25 | | | | | 30 | | |

| | | | | | | | | | | | |
|---|---|---|---|---|---|---|---|---|---|---|---|
| Met | Asn | Trp | Val | Lys | Gln | Arg | Pro | Gly | Lys | Gly | Leu | Glu | Trp | Ile | Gly |
| | | | 35 | | | | | 40 | | | | | 45 | | |

| | | | | | | | | | | | | | | | |
|---|---|---|---|---|---|---|---|---|---|---|---|---|---|---|---|
| Arg | Ile | Tyr | Pro | Val | Asn | Gly | Asp | Thr | Asn | Tyr | Asn | Gly | Lys | Phe | Lys |
| | 50 | | | | | 55 | | | | | 60 | | | | |

| | | | | | | | | | | | | | | | |
|---|---|---|---|---|---|---|---|---|---|---|---|---|---|---|---|
| Gly | Lys | Ala | Thr | Leu | Thr | Ala | Asp | Lys | Ser | Ser | Ser | Thr | Ala | Tyr | Met |
| 65 | | | | | 70 | | | | | 75 | | | | | 80 |

| | | | | | | | | | | | | | | | |
|---|---|---|---|---|---|---|---|---|---|---|---|---|---|---|---|
| Gln | Leu | Ser | Ser | Leu | Thr | Ser | Glu | Asp | Ser | Ala | Val | Tyr | Phe | Cys | Ala |
| | | | | 85 | | | | | 90 | | | | | 95 | |

| | | | | | | | | | | | | |
|---|---|---|---|---|---|---|---|---|---|---|---|---|
| Thr | Asp | Gly | Tyr | Trp | Tyr | Phe | Asp | Val | Trp | Gly | Gln | Gly | Thr | Thr | Val |
| | | | 100 | | | | | 105 | | | | | 110 | | |

Thr Val Ser Ser
     115

(2) INFORMATION FOR SEQ ID NO:10:

(i) SEQUENCE CHARACTERISTICS:
        (A) LENGTH: 348 base pairs
        (B) TYPE: nucleic acid
        (C) STRANDEDNESS: double
        (D) TOPOLOGY: linear (ii) MOLECULE TYPE: cDNA to mRNA (xi) SEQUENCE DESCRIPTION: SEQ ID NO:10:

```
GTGAAGCTGC AGGAGTCTGG ACCTGAGCTG GTGAAGCCTG GGGCCTCAGT GAAGATTTCC    60
TGCAAGGCTT CTGGCTATGC ATTCAGTAGC TCCTGGATGA ACTGGGTGAA ACAGAGGCCT   120
GGGAAGGGTC TTGAGTGGAT TGGACGGATT TATCCTGTAA ATGGAGATAC TAACTACAAT   180
GGGAAGTTCA AGGGCAAGGC CACACTGACT GCAGACAAAT CCTCCAGCAC AGCCTACATG   240
CAACTCAGCA GCCTGACATC TGAGGACTCT GCGGTCTACT TCTGTGCAAC CGATGGTTAC   300
TGGTACTTCG ATGTCTGGGG CCAAGGGACC ACGGTCACCG TCTCCTCA                348
```

(2) INFORMATION FOR SEQ ID NO:11:

(i) SEQUENCE CHARACTERISTICS:
        (A) LENGTH: 118 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:11:

| | | | | | | | | | | | | | | | |
|---|---|---|---|---|---|---|---|---|---|---|---|---|---|---|---|
| Val | Gln | Leu | Gln | Glu | Ser | Gly | Pro | Gly | Leu | Val | Lys | Pro | Ser | Gln | Ser |
| 1 | | | | 5 | | | | | 10 | | | | | 15 | |

| | | | | | | | | | | | | | | | |
|---|---|---|---|---|---|---|---|---|---|---|---|---|---|---|---|
| Leu | Ser | Leu | Thr | Cys | Ser | Val | Thr | Gly | Tyr | Ser | Ile | Thr | Ser | Gly | Tyr |
| | | | 20 | | | | | 25 | | | | | 30 | | |

| | | | | | | | | | | | | | | | |
|---|---|---|---|---|---|---|---|---|---|---|---|---|---|---|---|
| Tyr | Trp | Asn | Trp | Ile | Arg | Gln | Phe | Pro | Gly | Asn | Lys | Leu | Glu | Trp | Met |
| | | | 35 | | | | | 40 | | | | | 45 | | |

| | | | | | | | | | | | | | | | |
|---|---|---|---|---|---|---|---|---|---|---|---|---|---|---|---|
| Gly | Tyr | Ile | Ser | Tyr | Asp | Gly | Ser | Asn | Asn | Tyr | Asn | Pro | Ser | Leu | Lys |
| | 50 | | | | | 55 | | | | | 60 | | | | |

```
Asn Arg Ile Ser Ile Thr Arg Asp Thr Ser Lys Asn Gln Phe Phe Leu
 65                  70                  75                  80

Lys Leu Asn Ser Val Thr Thr Glu Asp Thr Ala Thr Tyr Tyr Cys Ala
                 85                  90                  95

Val Tyr Tyr Tyr Asp Gly Ser Ser Phe Asp Tyr Trp Gly Gln Gly Thr
            100                 105                 110

Thr Val Thr Val Ser Ser
            115
```

(2) INFORMATION FOR SEQ ID NO:12:

(i) SEQUENCE CHARACTERISTICS:
        (A) LENGTH: 354 base pairs
        (B) TYPE: nucleic acid
        (C) STRANDEDNESS: double
        (D) TOPOLOGY: linear (ii) MOLECULE TYPE: cDNA to mRNA (xi) SEQUENCE DESCRIPTION: SEQ ID NO:12:

```
GTGCAGCTGC AGGAGTCTGG ACCTGGCCTC GTGAAACCTT CTCAGTCTCT GTCTCTCACC    60

TGCTCTGTCA CTGGCTACTC CATCACCAGT GGTTATTACT GGAACTGGAT CCGGCAGTTT   120

CCAGGAAACA AACTGGAATG GATGGGCTAC ATAAGCTACG ATGGTAGCAA TAACTACAAC   180

CCATCTCTCA AAAATCGAAT CTCCATCACT CGTGACACAT CTAAGAACCA GTTTTTCCTG   240

AAGTTGAATT CTGTGACTAC TGAGGACACA GCCACATATT ACTGTGCCGT TTATTACTAC   300

GATGGTAGCT CTTTTGACTA CTGGGGCCAA GGGACCACGG TCACCGTCTC CTCA         354
```

(2) INFORMATION FOR SEQ ID NO:13:

(i) SEQUENCE CHARACTERISTICS:
        (A) LENGTH: 112 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:13:

```
Asp Ile Val Leu Thr Gln Ser Pro Ala Ser Leu Ala Val Ser Leu Arg
 1               5                  10                  15

Gln Arg Ala Thr Ile Ser Cys Arg Ala Ser Glu Gly Val Asp Ser Tyr
                 20                  25                  30

Gly Ile Ser Phe Met His Trp Tyr Gln Gln Lys Pro Gly Gln Pro Pro
             35                  40                  45

Lys Leu Leu Ile Tyr Arg Ala Ser Tyr Leu Lys Ser Gly Val Pro Ala
         50                  55                  60

Arg Phe Ser Gly Ser Gly Ser Arg Thr Asp Phe Thr Leu Thr Ile Asp
 65                  70                  75                  80

Pro Val Glu Ala Asp Asp Ala Ala Thr Tyr Tyr Cys Gln Gln Asn Asn
                 85                  90                  95

Glu Asp Pro Trp Thr Phe Gly Gly Gly Thr Lys Leu Glu Ile Lys Arg
            100                 105                 110
```

(2) INFORMATION FOR SEQ ID NO:14:

(i) SEQUENCE CHARACTERISTICS:
        (A) LENGTH: 336 base pairs
        (B) TYPE: nucleic acid
        (C) STRANDEDNESS: double
        (D) TOPOLOGY: linear (ii) MOLECULE TYPE: cDNA to mRNA (xi) SEQUENCE DESCRIPTION: SEQ ID NO:14:

```
GACATTGTGC TGACCCAATC TCCAGCTTCT TTGGCTGTGT CTCTAAGGCA GAGGGCCACC      60
ATATCCTGCA GAGCCAGTGA AGGTGTTGAT AGTTATGGCA TTAGTTTTAT GCACTGGTAC     120
CAGCAGAAAC AGGACAGCC ACCCAAACTC CTCATCTATC GTGCATCCTA CCTAAAATCT     180
GGGGTCCCTG CCAGGTTCAG TGGTAGTGGG TCTAGGACAG ACTTCACCCT CACCATTGAT     240
CCTGTGGAGG CTGATGATGC TGCAACCTAT TACTGTCAGC AAAATAATGA GGATCCGTGG     300
ACGTTCGGTG GAGGCACCAA GCTGGAAATC AAACGG                                336
```

(2) INFORMATION FOR SEQ ID NO:15:

(i) SEQUENCE CHARACTERISTICS:
        (A) LENGTH: 117 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:15:

```
Val Gln Leu Gln Glu Ser Gly Ala Glu Pro Ala Lys Pro Gly Ala Ser
  1               5                  10                  15

Val Lys Met Ser Cys Lys Ala Ser Gly Tyr Thr Phe Thr Thr Tyr Trp
             20                  25                  30

Met His Trp Val Lys Gln Arg Pro Gly Gln Gly Leu Glu Trp Ile Gly
         35                  40                  45

Tyr Ile Asn Pro Ser Ser Gly Tyr Thr Glu Tyr Asn Gln Lys Phe Lys
     50                  55                  60

Asp Lys Ala Thr Leu Thr Ala Asp Lys Ser Ser Thr Ala Tyr Met
 65                  70                  75                  80

Gln Leu Ile Ser Leu Thr Ser Glu Asp Ser Ala Val Tyr Tyr Cys Ala
                 85                  90                  95

Arg Arg Gly Asn Tyr Tyr Tyr Phe Asp Tyr Trp Gly Gln Gly Thr Thr
                100                 105                 110

Val Thr Val Ser Ser
            115
```

(2) INFORMATION FOR SEQ ID NO:16:

(i) SEQUENCE CHARACTERISTICS:
        (A) LENGTH: 351 base pairs
        (B) TYPE: nucleic acid
        (C) STRANDEDNESS: double
        (D) TOPOLOGY: linear (ii) MOLECULE TYPE: cDNA to mRNA (xi) SEQUENCE DESCRIPTION: SEQ ID NO:16:

```
GTGCAGCTGC AGGAGTCTGG GGCTGAACCG GCAAAACCTG GGGCCTCAGT GAAGATGTCC      60
TGCAAGGCTT CTGGCTACAC CTTTACTACC TACTGGATGC ACTGGGTAAA ACAGAGGCCT     120
GGACAGGGTC TGGAATGGAT TGGATACATT AATCCTAGCA GTGGTTATAC TGAGTACAAT     180
CAGAAGTTCA AGGACAAGGC CACATTGACT GCAGACAAAT CCTCCAGCAC AGCCTACATG     240
CAACTAATCA GCCTGACATC TGAGGACTCT GCAGTCTATT ACTGTGCAAG AAGGGGTAAT     300
TACTACTACT TTGACTACTG GGGCCAAGGG ACCACGGTCA CCGTCTCCTC A              351
```

(2) INFORMATION FOR SEQ ID NO:17:

(i) SEQUENCE CHARACTERISTICS:
        (A) LENGTH: 105 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:17:

```
Asp Val Leu Met Thr Gln Thr Pro Lys Phe Leu Pro Val Ser Ala Gly
 1               5                  10                  15

Asp Arg Val Thr Met Thr Cys Lys Ala Ser Gln Ser Val Gly Asn Asn
            20                  25                  30

Val Ala Trp Tyr Gln Gln Lys Pro Gly Gln Ser Pro Lys Leu Leu Ile
        35                  40                  45

Tyr Tyr Thr Ser Asn Arg Tyr Thr Gly Val Pro Asp Arg Phe Thr Gly
50                  55                  60

Ser Gly Ser Gly Thr Asp Phe Thr Phe Thr Ile Ser Ser Val Gln Val
65                  70                  75                  80

Glu Asp Leu Ala Val Tyr Phe Cys Gln Gln His Tyr Ser Ser Pro Tyr
                85                  90                  95

Thr Phe Gly Ser Gly Thr Lys Leu Glu
            100                 105
```

(2) INFORMATION FOR SEQ ID NO:18:

(i) SEQUENCE CHARACTERISTICS:
        (A) LENGTH: 315 base pairs
        (B) TYPE: nucleic acid
        (C) STRANDEDNESS: double
        (D) TOPOLOGY: linear (ii) MOLECULE TYPE: cDNA to mRNA (xi) SEQUENCE DESCRIPTION: SEQ ID NO:18:

```
GATGTTTTGA TGACCCAAAC TCCAAAATTC CTGCCTGTAT CAGCAGGAGA CAGGGTTACC    60

ATGACCTGCA AGGCCAGTCA GAGTGTGGGT AATAATGTGG CCTGGTACCA ACAGAAGCCA   120

GGACAGTCTC CTAAACTGCT GATATACTAT ACATCCAATC GCTACACTGG AGTCCCTGAT   180

CGCTTCACTG GCAGTGGATC TGGGACAGAT TTCACTTTCA CCATCAGCAG TGTGCAGGTT   240

GAAGACCTGG CAGTTTATTT CTGTCAGCAG CATTATAGCT CTCCGTATAC GTTCGGATCG   300

GGGACCAAGC TGGAG                                                    315
```

(2) INFORMATION FOR SEQ ID NO:19:

(i) SEQUENCE CHARACTERISTICS:
        (A) LENGTH: 121 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:19:

```
Gln Val Gln Leu Gln Gln Ser Gly Pro Glu Leu Val Lys Pro Gly Ala
 1               5                  10                  15

Ser Val Lys Ile Ser Cys Lys Ala Ser Gly Tyr Ala Phe Ser Ser Ser
            20                  25                  30

Trp Met Asn Trp Val Lys Gln Arg Pro Gly Lys Gly Leu Glu Trp Ile
```

```
               35                  40                  45
Gly Arg Ile Tyr Pro Gly Asp Gly Asp Thr Asn Asp Asn Gly Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Ser Tyr Tyr Tyr Asp Gly Ser Pro Trp Phe Thr Tyr Trp Gly
                100                 105                 110

Gln Gly Thr Leu Val Thr Val Ser Ala
        115                 120

(2) INFORMATION FOR SEQ ID NO:20:

(i) SEQUENCE CHARACTERISTICS:
        (A) LENGTH: 363 base pairs
        (B) TYPE: nucleic acid
        (C) STRANDEDNESS: double
        (D) TOPOLOGY: linear (ii) MOLECULE TYPE: cDNA to mRNA (xi) SEQUENCE DESCRIPTION: SEQ ID NO:20:

CAGGTTCAGC TGCAGCAGTC TGGACCTGAG CTGGTGAAGC CTGGGGCCTC AGTGAAGATT      60

TCCTGCAAGG CTTCTGGCTA TGCATTCAGT AGCTCCTGGA TGAACTGGGT GAAGCAGAGG     120

CCTGGAAAGG GTCTTGAGTG GATTCGAATT TATCCTGGAG ATGGAGATAC TAACGACAAC     180

GGGAAGTTCA AGGGAGGCAA GGCCACACTG ACCGCAGACA AATCCTCCAG CACAGCCTAC     240

ATGCAACTCA GCAGTCTGAC ATCTGAGGAC TCTGCGGTCT ACTTCTGTGC AAGATCGTAT     300

TACTACGATG GTAGCCCCTG GTTTACTTAC TGGGGCCAAG GGACTCTGGT CACTGTCTCT     360

GCA                                                                  363

(2) INFORMATION FOR SEQ ID NO:21:

(i) SEQUENCE CHARACTERISTICS:
        (A) LENGTH: 108 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:21:

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
                20                  25                  30

Leu Asn Trp Tyr Gln Gln Lys Pro Asp Gly Thr Val Lys Leu Leu Ile
            35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Pro
65                  70                  75                  80

Glu Asp Ile Ala Thr Tyr Phe Cys Gln Gln Tyr Ser Glu Phe Pro Trp
                85                  90                  95

Thr Phe Gly Gly Gly Thr Lys Leu Glu Ile Lys Arg
                100                 105
```

(2) INFORMATION FOR SEQ ID NO:22:

(i) SEQUENCE CHARACTERISTICS:
        (A) LENGTH: 324 base pairs
        (B) TYPE: nucleic acid
        (C) STRANDEDNESS: double
        (D) TOPOLOGY: linear (ii) MOLECULE TYPE: cDNA to mRNA (xi) SEQUENCE DESCRIPTION: SEQ ID NO:22:

```
GATATCCAGA TGACACAGAC TACATCCTCC CTGTCTGCCT CTCTGGGAGA CAGAGTCACC    60

ATCAGTTGCA GGGCAAGTCA GGATATTAGC AATTATTTAA ACTGGTATCA GCAGAAACCA   120

GATGGAACTG TTAAACTCCT GATCTACTAC ACATCAAGAT TACACTCAGG AGTCCCATCA   180

AGGTTCAGTG GCAGTGGGTC TGGGACAGAT TATTCTCTCA CCATCAGCAA CCTGGAACCT   240

GAAGATATTG CCACTTACTT TTGTCAGCAA TATAGTGAAT TTCCGTGGAC GTTCGGTGGA   300

GGCACCAAGC TGGAAATCAA ACGG                                          324
```

(2) INFORMATION FOR SEQ ID NO:23:

(i) SEQUENCE CHARACTERISTICS:
        (A) LENGTH: 119 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:23:

```
Gln Val His Leu Gln Gln Ser Gly Ala Glu Leu Val Arg Pro Gly Thr
  1               5                  10                  15

Ser Val Lys Met Ser Cys Lys Ala Ala Gly Tyr Thr Phe Thr Asn Tyr
                 20                  25                  30

Trp Ile Gly Trp Val Lys Gln Arg Pro Gly His Gly Leu Glu Trp Ile
             35                  40                  45

Gly Tyr Leu Tyr Pro Gly Gly Leu Tyr Thr Asn Tyr Asn Glu Lys Phe
         50                  55                  60

Lys Gly Lys Ala Thr Leu Thr Ala Asp Thr Ser Ser Thr Ala Tyr
 65                  70                  75                  80

Met Gln Leu Ser Ser Leu Thr Ser Glu Asp Ser Ala Ile Tyr Tyr Cys
                 85                  90                  95

Ala Arg Tyr Arg Asp Tyr Asp Tyr Ala Met Asp Tyr Trp Gly Gln Gly
                100                 105                 110

Thr Ser Val Thr Val Ser Ser
            115
```

(2) INFORMATION FOR SEQ ID NO:24:

(i) SEQUENCE CHARACTERISTICS:
        (A) LENGTH: 357 base pairs
        (B) TYPE: nucleic acid
        (C) STRANDEDNESS: double
        (D) TOPOLOGY: linear (ii) MOLECULE TYPE: cDNA to mRNA (xi) SEQUENCE DESCRIPTION: SEQ ID NO:24:

```
CAGGTCCACC TGCAGCAGTC TGGAGCTGAG CTGGTAAGGC CTGGGACTTC AGTGAAGATG    60

TCCTGCAAGG CTGCTGGATA CACCTTCACT AACTACTGGA TAGGTTGGGT AAAGCAGAGG   120

CCTGGACATG GCCTTGAGTG GATTGGATAT CTTTACCCTG GAGGTCTTTA TACTAACTAC   180
```

```
AATGAGAAGT TCAAGGGCAA GGCCACACTG ACTGCAGACA CATCCTCCAG CACAGCCTAC      240

ATGCAGCTCA GCAGCCTGAC ATCTGAGGAC TCTGCCATCT ATTACTGTGC AAGATACAGG      300

GATTACGACT ATGCTATGGA CTACTGGGGT CAAGGAACCT CAGTCACCGT CTCCTCA         357
```

(2) INFORMATION FOR SEQ ID NO:25:

(i) SEQUENCE CHARACTERISTICS:
        (A) LENGTH: 113 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:25:

```
Asp Val Val Leu Thr Gln Thr Pro Leu Ser Leu Pro Val Asn Ile Gly
 1               5                  10                  15

Asp Gln Ala Ser Ile Ser Cys Lys Ser Thr Lys Ser Leu Leu Asn Ser
            20                  25                  30

Asp Gly Phe Thr Tyr Leu Gly Trp Cys Leu Gln Lys Pro Gly Gln Ser
        35                  40                  45

Pro Gln Leu Leu Ile Tyr Leu Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Ser
                85                  90                  95

Asn Tyr Leu Pro Leu Thr Phe Gly Ser Gly Thr Lys Leu Glu Ile Lys
            100                 105                 110

Arg
```

(2) INFORMATION FOR SEQ ID NO:26:

(i) SEQUENCE CHARACTERISTICS:
        (A) LENGTH: 339 base pairs
        (B) TYPE: nucleic acid
        (C) STRANDEDNESS: double
        (D) TOPOLOGY: linear (ii) MOLECULE TYPE: cDNA to mRNA (xi) SEQUENCE DESCRIPTION: SEQ ID NO:26:

```
GATGTTGTTC TGACCCAAAC TCCACTCTCT CTGCCTGTCA ATATTGGAGA TCAAGCCTCT       60

ATCTCTTGCA AGTCTACTAA GAGCCTTCTG AATAGTGATG GATTCACTTA TTTGGGCTGG      120

TGCCTGCAGA AGCCAGGCCA GTCTCCACAG CTCCTAATAT ATTTGGTTTC TAATCGATTT      180

TCTGGAGTTC CAGACAGGTT CAGTGGTAGT GGGTCAGGGA CAGATTTCAC CCTCAAGATC      240

AGCAGAGTGG AGGCTGAGGA TTTGGGAGTT TATTATTGCT TCCAGAGTAA CTATCTTCCT      300

CTTACGTTCG GATCGGGGAC CAAGCTGGAA ATAAAACGG                             339
```

(2) INFORMATION FOR SEQ ID NO:27:

(i) SEQUENCE CHARACTERISTICS:
        (A) LENGTH: 117 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:27:

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Ala Phe Ser Ser Ser
            20                  25                  30

Trp Met Asn Trp Val Lys Gln Arg Pro Gly Lys Gly Leu Glu Trp Ile
        35                  40                  45

Gly Arg Ile Tyr Pro Val Asn Gly Asp Thr Asn Tyr Asn Gly Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Thr Asp Gly Tyr Trp Tyr Phe Asp Val Trp Gly Ala Gly Thr Thr
                100                 105                 110

Val Thr Val Ser Ser
            115

(2) INFORMATION FOR SEQ ID NO:28:

(i) SEQUENCE CHARACTERISTICS:
        (A) LENGTH: 351 base pairs
        (B) TYPE: nucleic acid
        (C) STRANDEDNESS: double
        (D) TOPOLOGY: linear (ii) MOLECULE TYPE: cDNA to mRNA (xi) SEQUENCE DESCRIPTION: SEQ ID NO:28:

CAGGTTCAGC TGCAGCAGTC TGGACCTGAG CTGGTGAAGC CTGGGGCCTC AGTGAAGATT    60

TCCTGCAAGG CTTCTGGCTA TGCATTCAGT AGCTCCTGGA TGAACTGGGT GAAACAGAGG   120

CCTGGGAAGG GTCTTGAGTG GATTGGACGG ATTTATCCTG TAAATGGAGA TACTAACTAC   180

AATGGGAAGT TCAAGGGCAA GGCCACACTG ACTGCAGACA AATCCTCCAG CACAGCCTAC   240

ATGCAACTCA GCAGCCTGAC ATCTGAGGAC TCTGCGGTCT ACTTCTGTGC AACCGATGGT   300

TACTGGTACT TCGATGTCTG GGGCGCAGGG ACCACGGTCA CCGTCTCCTC A            351

(2) INFORMATION FOR SEQ ID NO:29:

(i) SEQUENCE CHARACTERISTICS:
        (A) LENGTH: 108 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:29:

Asn Ile Val Met Thr Gln Ser Pro Lys Ser Met Ser Met Ser Val Gly
1               5                   10                  15

Glu Arg Val Thr Leu Ser Cys Lys Ala Ser Glu Asn Val Asp Ile Tyr
            20                  25                  30

Val Ser Trp Tyr Gln Gln Lys Pro Glu Gln Ser Pro Lys Leu Leu Ile
        35                  40                  45

Tyr Gly Thr Ser Asn Arg Tyr Thr Gly Val Pro Asp Arg Phe Thr Gly
    50                  55                  60

Ser Gly Ser Ala Thr Asp Phe Thr Leu Thr Ile Ser Asn Val Gln Ala
65                  70                  75                  80

-continued

```
Glu Asp Leu Ser Asp Tyr Tyr Cys Val Gln Ser Tyr Ser Tyr Pro Trp
                85                  90                  95
Thr Phe Gly Gly Gly Thr Lys Leu Glu Ile Lys Arg
            100                 105
```

(2) INFORMATION FOR SEQ ID NO:30:

(i) SEQUENCE CHARACTERISTICS:
        (A) LENGTH: 324 base pairs
        (B) TYPE: nucleic acid
        (C) STRANDEDNESS: double
        (D) TOPOLOGY: linear (ii) MOLECULE TYPE: cDNA to mRNA (xi) SEQUENCE DESCRIPTION: SEQ ID NO:30:

```
AACATTGTAA TGACCCAATC TCCCAAATCC ATGTCCATGT CAGTAGGAGA GAGGGTCACC      60

TTGAGCTGCA AGGCCAGTGA GAATGTGGAT ATTTATGTAT CCTGGTATCA ACAGAAACCA     120

GAGCAGTCTC CTAAACTGCT GATATACGGG ACATCCAACC GGTACACTGG GGTCCCCGAT     180

CGCTTCACAG GCAGTGGATC TGCAACAGAT TTCACTCTGA CCATCAGCAA TGTGCAGGCT     240

GAAGACCTTT CAGATTATTA CTGTGTACAG AGTTACAGCT ATCCGTGGAC ATTCGGTGGA     300

GGCACCAAGC TGGAAATCAA ACGG                                            324
```

(2) INFORMATION FOR SEQ ID NO:31:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:31:

```
Leu Ser His Lys Val Tyr Met Arg Asn Ser Lys Tyr Pro Gln
1               5                   10
```

MONOCLONAL ANTIBODY REACTING SPECIFICALLY REACTING WITH FAS LIGAND AND PRODUCTION PROCESS THEREOF

TECHNICAL FIELD

The present invention relates to monoclonal antibodies which specifically react with a Fas ligand present on a cell surface, active fragments thereof, a method of detecting a Fas ligand, and kits for use in detecting a Fas ligand. The present invention also relates to a process for producing monoclonal antibodies which specifically react with a Fas ligand present on a cell surface, and hybridomas separately producing these monoclonal antibodies. The monoclonal antibodies according to the present invention are useful in elucidation of a Fas system and the like in cell death, immunothearpy and immunodiagnoses, detection of a Fas ligand, and industrial fields associated with them.

In the present invention, the active fragments mean fragments having the antigen-antibody reaction activity of the antibodies. Specific examples thereof include $F(ab')_2$, Fab', Fab, Fv and recombinant Fv.

BACKGROUND ART

Multicellular organisms skillfully control the proliferation and death of cells to maintain their homeostasis. Many cells are removed by cell death in the course of ontogeny. In an adult, cells constituting organs always maintain their functions while keeping a balance between their proliferation and death. Such cell death is preliminarily programmed death called "programmed cell death" and is distinguished from "accidental cell death" caused by physical and chemical factors. These two deaths are different from each other in process. More specifically, the programmed cell death is caused by a process of apoptosis, while in the accidental cell death, cells are killed via a process of necrosis.

A Fas antigen is a cell-surface protein that mediates cell death (apoptosis). Recently, a cDNA of the Fas antigen was cloned jointly by Dr. Naoto Ito, Dr. Shigekazu Nagata et al. in Osaka Bioscience Institute (Cell, Vol. 66, pp. 223–243, 1991). It was found from the structure of the cDNA thus obtained that a human Fas antigen is a transmembrane protein consisting of 319 amino acid residues and has one transmembrane region. The extracellular region of the Fas antigen is constituted by 157 amino acid residues and has a cysteine residue-rich structure. A mouse Fas antigen consists of 306 amino acid residues and has a homology of 49.3% with the human Fas antigen.

It was found that the cysteine residue-rich structure of the extracellular region in the Fas antigen is a well conserved structure recognized in a low-affinity receptor of NGF (nerve growth factor) and a receptor of TNF (tumor necrosis factor). This fact revealed that the Fas antigen is a cell-surface protein belonging to the NGF/TNF receptor family. Since many of proteins belonging to this family have their ligands in the living body, the Fas antigen is also expected to have its ligand in the living body. A molecule of a rat Fas ligand was identified by a group of Dr. Shigekazu Nagata et al. in Osaka Bioscience Institute in 1993 (Cell, Vol. 75, pp. 1169–1178, 1993), and subsequently molecules of mouse and human Fas ligands were identified by the same group (Int. Immunol., Vol. 6 No. 10, pp. 1567–1574).

It has been understood that the Fas antigen mediates a signal of "death" to cells. Besides, an anti-Fas antibody induces apoptosis against certain cells. In a mouse having 1pr (lymphoproliferation) mutation exhibiting the symptom of autoimmune disease, it has been found that the mutation exists in its Fas gene. These results suggest that the inactivation of proteins mediating apoptosis, such as the Fas antigen, causes abnormal proliferation of cells, while abnormal activation thereof causes certain inflammatory reactions.

For example, it has been reported that the expression of Fas is recognized in acquired immunodeficiency virus-infected T cells (Proc. Natl. Acad. Sci. USA, Vol. 87, pp. 9620–9624, 1990), that when an anti-Fas antibody (Jo-2) is intraperitoneally administered to mice, the mice are attacked by fulminant hepatitis (Nature, Vol. 364, pp. 806–809, 1993), that the expression of Fas is recognized in viral hepatitis (Hepatology, Vol. 19, pp. 1354–1359, 1994), and that even in autoimmune diseases, the expression of Fas is recognized in SLE (systemic lupus erythematodes) and RA (rheumatoid arthritis). These may be considered to be caused by a Fas ligand reacting with a Fas antigen. However, it takes formidable experiments to actually confirm them.

As described above, the researches of Fas antigens prove that in an immune system, a system mediating a signal of "death" works from the outside of cells. However, there has been yet no knowing whether the cell death in development and neurocytes is induced by a like signal from the outside (the system of Fas works) or programmed in cells as called programmed cell death. Its elucidation is an important problem in future.

A signal transfer mechanism for inducing apoptosis against cells, i.e., a problem that apoptosis is induced from a Fas antigen by what signal transfer mechanism, is also not elucidated. In order to exactly understand the system of Fas, it is necessary to make a ligand of the Fas (Fas ligand) and its function clear and to reconsider the system of Fas from the viewpoint of the interaction between ligand and receptor.

As described above, the gene of a Fas ligand was identified by Dr. Shigekazu Nagata et al. As a result, according to the above literature, "Cell", it has been found that the Fas ligand is a protein consisting of 278 amino acids with a molecular weight of 31,138, and it has also been found that 4 N-glycoside-bond sites exist therein, and it is hence a glycoprotein (Cell Technology, Vol. 13 No. 8, pp. 738–744, 1994).

The report in literature by Hanabuchi et al. (Proc. Natl. Acad. Sci. USA, Vol. 91, No. 11, pp. 4930–4934, 1994) has showed that as a result of the analysis of the mechanism of lysing target cells by killer T cells via a Fas antigen, there is a possibility that the transmission of an apoptosis signal via the Fas antigen on the target cells may take part in the lysis of the target cells by $CD4^+$ T cells (CTL) which do not express perforin. This has revealed that a Fas ligand exists on the cell surface of $CD4^+$ CTL.

In a mouse having gld (generalized lymphoproliferative disease) mutation exhibiting the symptom of autoimmune disease, it has been found that the mutation exists in its Fas gene (Cell, Vol. 76, pp. 969–979, 1994).

However, the recognition that a Fas ligand may play an important role in vital reactions has been just gained under circumstances. As described above, the Fas ligand molecule has been just identified at present, and so the mechanism of Fas and the Fas ligand has been just started to be elucidated. In order to make this mechanism clear, analysis at the protein level (immunological analysis), or acquisition of neutralizing antibodies or the like which inhibit the binding action of Fas to the Fas ligand is essential.

DISCLOSURE OF THE INVENTION

It is an object of the present invention to provide monoclonal antibodies, which specifically react with a Fas ligand present on a cell surface, active fragments thereof, a production process of the monoclonal antibodies, and hybridomas separately producing the monoclonal antibodies.

Another object of the present invention is to provide monoclonal antibodies which can inhibit a physiological reaction between a Fas ligand and Fas, and specifically react with the Fas ligand.

A further object of the present invention is to determine the amino acid sequences of variable regions and hypervariable regions of a heavy chain (H chain) and a light chain (L chain) of such a monoclonal antibody, and the base sequences of DNAs encoding these sequences.

A still further object of the present invention is to detect a Fas ligand in a solution and a kit for use in detecting the Fas ligand.

The present inventors have considered that when a monoclonal antibody against Fas ligand is produced, the analysts of a Fas system will be advanced, and carried out an extensive investigation. As a result, the inventors have succeeded in acquiring monoclonal antibodies which specifically react with a Fas ligand, and hybridomas separately producing such antibodies.

The present inventors have further continued researches on the antibodies specifically reacting with a Fas ligand, and the like, and the present invention has been led to completion on the basis of the results of the researches.

According to the present invention, there are provided monoclonal antibodies, which specifically react with a Fas ligand, or active fragments thereof.

According to the present invention, there are also provided amino acid sequences of hypervariable regions and variable regions of the monoclonal antibodies, and the base sequences of DNAs or RNAs encoding said amino acid sequences.

According to the present invention, there are further provided antibodies, which react with a part of the amino acid sequence, LSHKVYMRNSKYPQ (SEQ ID NO: 31), in an extracellular region of a Fas ligand.

According to the present invention, there is still further provided a process for producing monoclonal antibodies specifically reacting with a Fas ligand, which comprises the steps of (1) immunosensitizing an animal with a Fas ligand molecule or cells on which the Fas ligand has been expressed, (2) preparing antibody-producing cells from the immunosensitized animal to form a suspension of the antibody-producing cells, (3) mixing the suspension of the antibody-producing cells with myeloma cells to fuse both cells, (4) diluting the fused cells with a medium which does not favor unfused myeloma cells to culture the fused cells, thereby sorting hybridomas produced by the fusion of the antibody-producing cells with the myeloma cells, (5) determining whether antibodies secreted in a culture supernatant containing the hybridomas are against the desired antigen or not using, as an indicator, the fact that the antibodies inhibit the attack of a Fas ligand present in a supernatant of Fas ligand-expressed COS cells against Fas-expressed cells, (6) cloning a series of cells in culture wells in which cells secreting the desired antibodies exist, (7) selecting a clone from which the desired antibody is secreted, (8) conducting cloning again to establish a hybridoma clone which secretes a monoclonal antibody against the desired antigen, and (9) preparing the monoclonal antibody from a culture supernatant of the hybridoma or ascites fluid obtained by intraperitoneally administering the hybridoma to a mouse.

According to the present invention, there are yet still further provided a process for producing monoclonal antibodies against Fas ligand, which comprises immunosensitizing an animal (excluding the human), which does not express a functional Fas molecule, with a Fas ligand or Fas ligand-expressed cells in the above process, and monoclonal antibodies against Fas ligand obtained by such a process.

According to the present invention, there are yet still further provided hybridomas separately producing monoclonal antibodies which specifically react with a Fas ligand present on a cell surface, a method of detecting a Fas ligand in a solution, which comprises combining a plurality of monoclonal antibodies against Fas ligand with each other, and a kit for use in detecting a Fas ligand, comprising a plurality of monoclonal antibodies against Fas ligand in combination.

BRIEF DESCRIPTION OF THE DRAWINGS

FIG. 13 illustrates amino acid sequences of VH regions (H chains) of monoclonal antibodies, NOK1 to NOK5, wherein portions enclosed with a rectangle represent hypervariable regions (CD1 to CD3).

FIG. 14 illustrates amino acid sequences of VL regions (L chains) of monoclonal antibodies, NOK1, NOK2, NOK4 and NOK5, wherein portions enclosed with a rectangle represent hypervariable regions (CD1 to CD3).

FIG. 15 illustrates amino acid sequences of VH regions (H chains) of mutants of monoclonal antibodies, NOK1 to NOK3, wherein portions enclosed with a rectangle represent hypervariable regions (CD1 to CD3).

FIG. 16 illustrates amino acid sequences of VL regions (L chains) of mutants of monoclonal antibodies, NOK1 to NOK3, wherein portions enclosed with a rectangle represent hypervariable regions (CD1 to CD3).

FIG. 17 is an FACScan chart illustrating stain patterns of BHK cells, wherein a dotted line represents the case where "no monoclonal antibody (KAY-10 antibody) against mouse Fas ligand was added" and a solid line represents the case where "a KAY-10 antibody was added".

Figure 18:
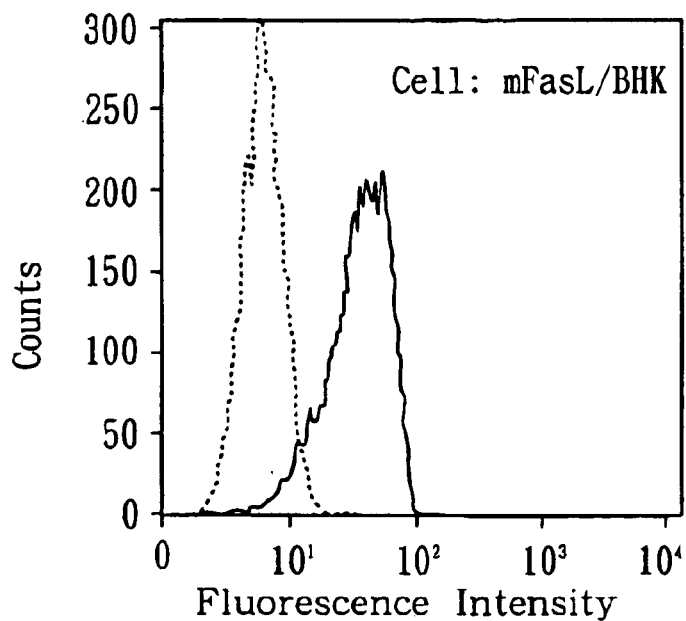
FIG. 18 is an FACScan chart illustrating stain patterns of mouse Fas ligand-expressed BHK cells, wherein a dotted line represents the case where "no monoclonal antibody (KAY-10 antibody) against mouse Fas ligand was added" and a solid line represents the case where "a KAY-10 antibody was added".
Figure 19:
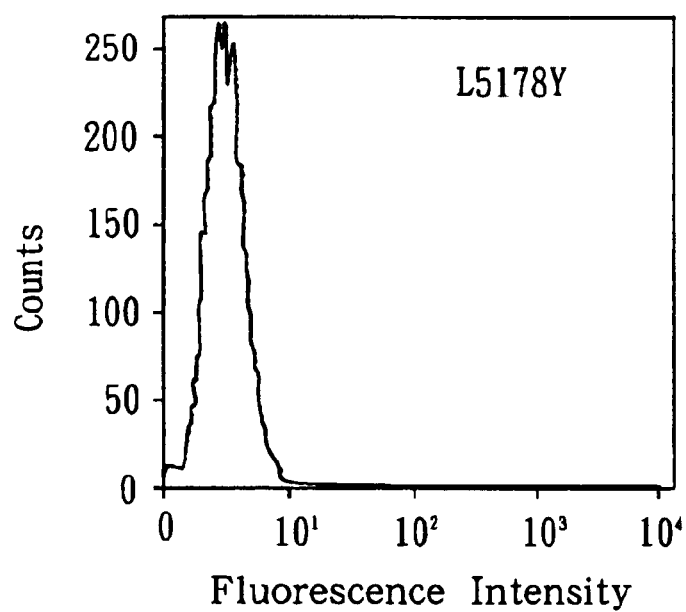
FIG. 19 is an FACScan chart illustrating stain patterns of L5178Y cells, wherein a dotted line represents the case where "no monoclonal antibody (KAY-10 antibody) against mouse Fas ligand was added" and a solid line represents the case where "a KAY-10 antibody was added".
Figure 20:
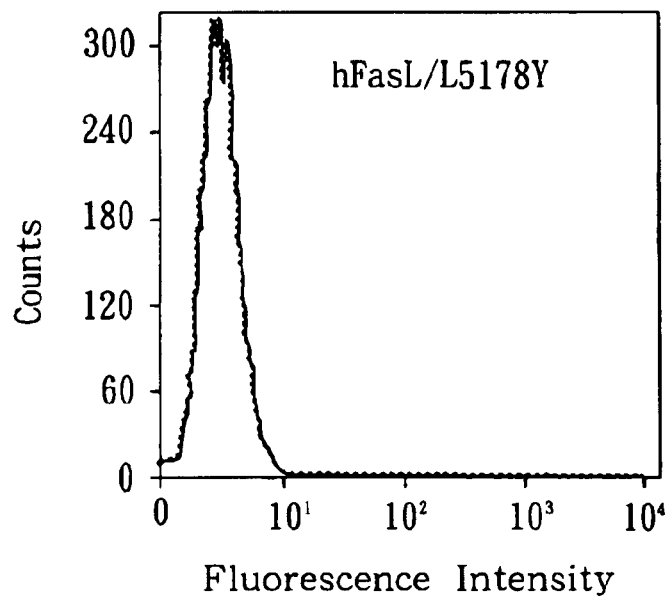
FIG. 20 is an FACScan chart illustrating stain patterns of human Fas ligand-expressed L5178Y cells, wherein a dotted line represents the case where "no monoclonal antibody (KAY-10 antibody) against mouse Fas ligand was added" and a solid line represents the case where "a KAY-10 antibody was added".
Figure 21:
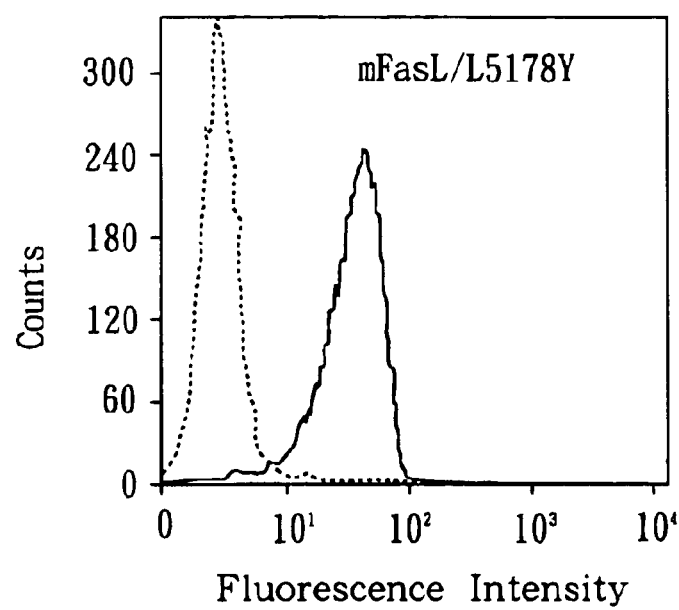
FIG. 21 is an FACScan chart illustrating stain patterns of mouse Fas ligand-expressed L5178Y cells, wherein a dotted line represents the case where "no monoclonal antibody (KAY-10 antibody) against mouse Fas ligand was added" and a solid line represents the case where "a KAY-10 antibody was added".

Slippage in peak was observed only in FIG. 18 and FIG. 21, and this fact demonstrates that the monoclonal antibody (KAY-10 antibody) against mouse Fas ligand reacts only with the mouse Fas ligand-expressed BHK cells and L5178Y cells, and does not react with their parent strains, BHK cells and L5178Y cells, and the human Fas ligand-expressed L5178Y cells.

Figure 22:
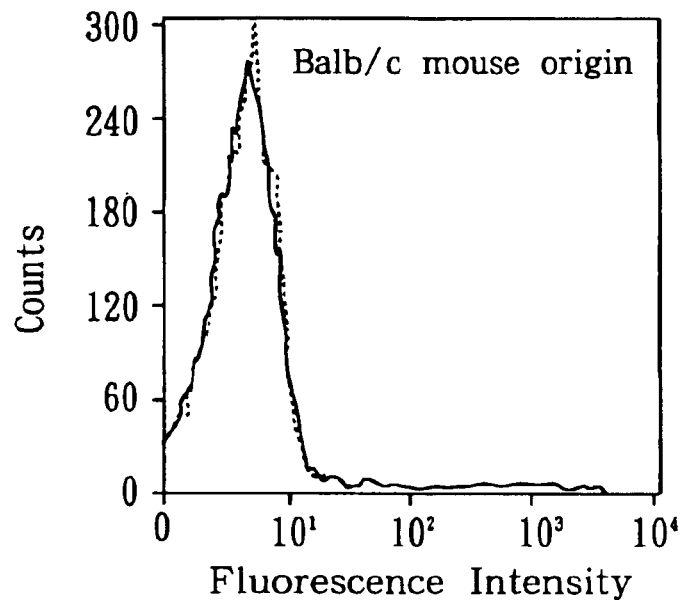

FIG. 22 is an FACScan chart illustrating stain patterns of activated T cells of a Fas ligand-expressed Balb/c mouse, wherein a dotted line represents the case where "no monoclonal antibody (KAY-10 antibody) against mouse Fas ligand was added" and a solid line represents the case where "a KAY-10 antibody was added".

Figure 23:
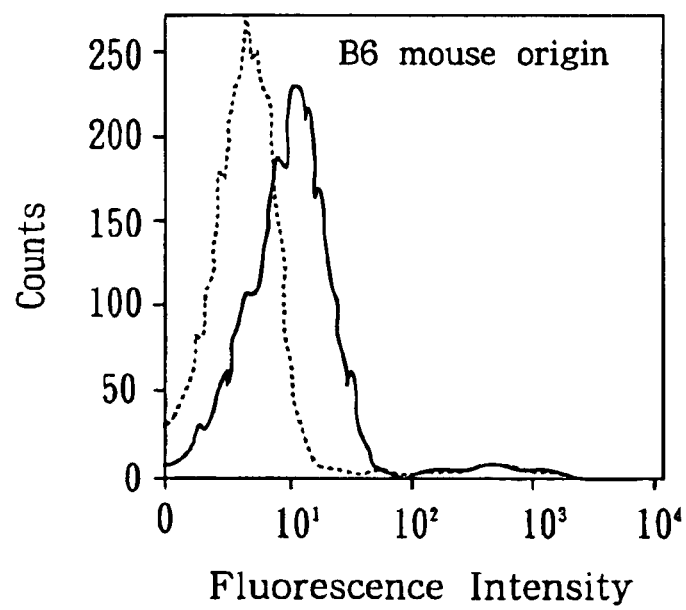

FIG. 23 is an FACScan chart illustrating stain patterns of activated T cells of a Fas ligand-expressed B6 mouse, wherein a dotted line represents the case where "no monoclonal antibody (KAY-10 antibody) against mouse Fas ligand was added" and a solid line represents the case where "a KAY-10 antibody was added".

Figure 24:
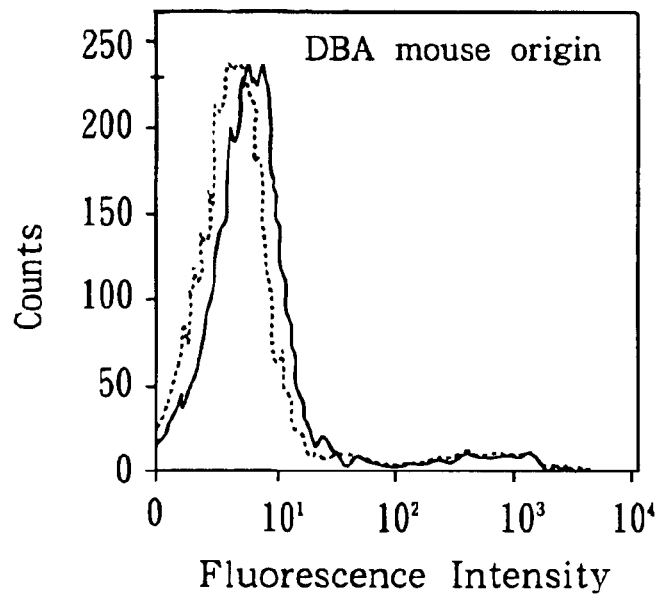

FIG. 24 is an FACScan chart illustrating stain patterns of activated T cells of a Fas ligand-expressed DBA mouse, wherein a dotted line represents the case where "no monoclonal antibody (KAY-10 antibody) against mouse Fas ligand was added" and a solid line represents the case where "a KAY-10 antibody was added".

Figure 25:
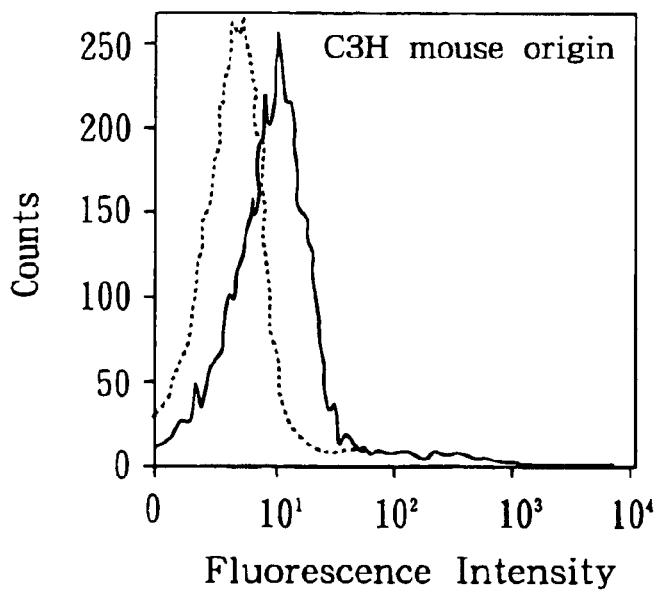

FIG. 25 is an FACScan chart illustrating stain patterns of activated T cells of a Fas ligand-expressed C3H mouse, wherein a dotted line represents the case where "no monoclonal antibody (KAY-10 antibody) against mouse Fas ligand was added" and a solid line represents the case where "a KAY-10 antibody was added".

Slippage in peak was scarcely observed in FIG. 24, and no slippage in peak was observed in FIG. 22. This fact demonstrates that the monoclonal antibody (KAY-10 antibody) against mouse Fas ligand weakly or scarcely reacts with the Fas ligands of cells derived from the DBA mouse and Balb/c mouse. On the other hand, slippage in peak was observed in FIG. 23 and FIG. 25, and this fact demonstrates that the KAY-10 antibody well reacts with the Fas ligands of cells derived from the B6 mouse and C3H mouse.

Figure 26:
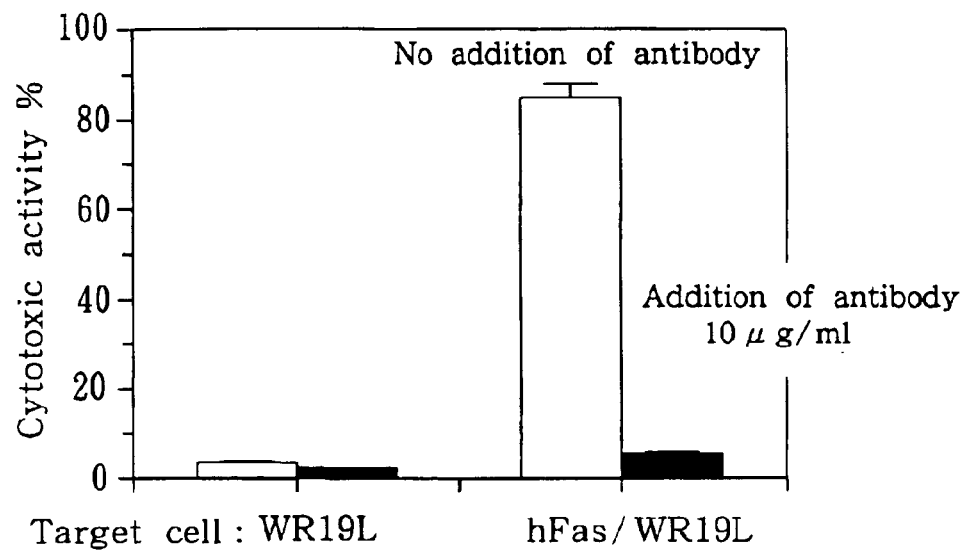

FIG. 26 is a graph illustrating the fact that the monoclonal antibody (KAY-10 antibody) against mouse Fas ligand has an inhibitory effect on the apoptosis inducibility to human Fas-expressed cells that the mouse Fas ligand has.

Figure 27:
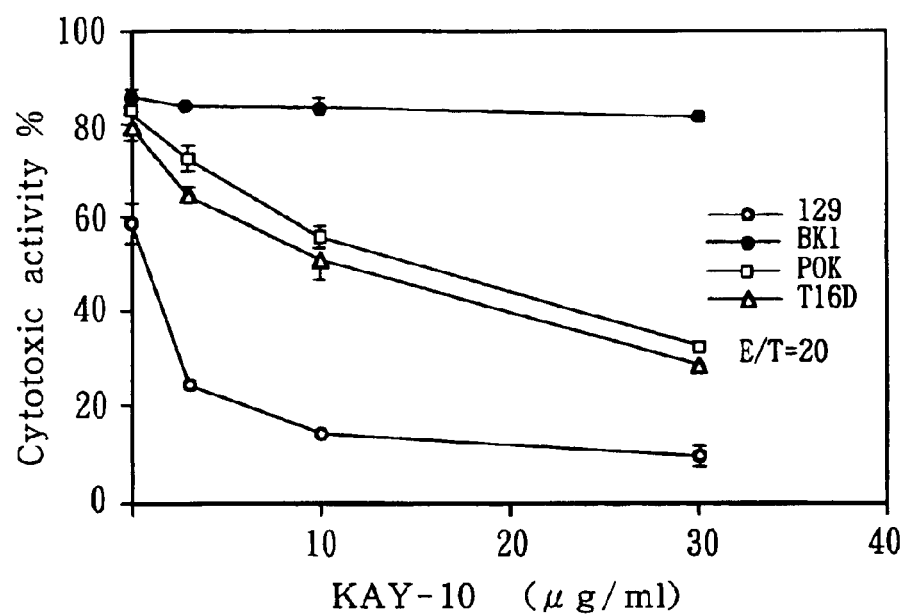

FIG. 27 is a graph illustrating the fact that the monoclonal antibody (KAY-10 antibody) against mouse Fas ligand inhibits apoptosis induction activities that various Th1 type T cells have, depending on its concentration.

BEST MODE FOR CARRYING OUT THE INVENTION

A Fas ligand (FasL) is a ligand of a Fas antigen (hereinafter may be referred to as "Fas" merely) that is a cell-surface protein mediating apoptosis. The identification of its gene has revealed that the Fas ligand is a protein consisting of 278 amino acids with a molecular weight of 31.138. Human, rat and mouse Fas ligands have been identified up to the present. The present invention is generally intended for the Fas ligands. Of these, the Fas ligands, the species of which are the human and mouse, are particularly preferred. Namely, the present invention relates to monoclonal antibodies which specifically react with the respective ligands of human and mouse Fas antigens, and active fragments thereof.

No particular limitation is imposed on the monoclonal antibodies according to the present invention so far as they specifically react with a Fas ligand. However, they can preferably inhibit a physiological reaction between a Fas ligand and Fas. The antibody, which inhibits the physiological reaction, as used herein means an antibody (neutralizing antibody) which can specifically bind to a binding site of a Fas ligand binding to Fas to prevent the Fas ligand from binding to Fas when a Fas ligand-expressed cell or a solubilized Fas ligand (sFas ligand) binds to a Fas-expressed cell to give a signal to the effect that the Fas-expressed cell is killed by apoptosis. Namely, when the monoclonal antibody which inhibits the physiological reaction of the Fas ligand with Fas is present, the Fas ligand-expressed cell or sFas ligand fails to kill the Fas-expressed cell.

In addition, the monoclonal antibodies preferably have stronger avidity than that between the Fas ligand and Fas. Specifically, the avidity can be determined by using, as an indicator, a chimera molecule (Fas-Ig) obtained by binding Fas to Fc of IgG. This Fas-Ig can bind to a Fas ligand with the same avidity as the avidity between the Fas ligand and Fas in vivo. Accordingly, if an antibody against the Fas ligand can inhibit the binding of the Fas ligand to Fas at a lower concentration than the Fas-Ig chimera molecule, in fact, various actions of the Fas ligand in vivo can be effectively inhibited at a practical level.

Examples of the monoclonal antibodies according to the present invention, which specifically react with a human Fas ligand, include respective monoclonal antibodies (NOK1 to NOK5) produced by hybridoma cell lines deposited as Accession Nos. FERM BP-5044 (Hybridoma NOK1), FERM BP-5045 (Hybridoma NOK2), FERM BP-5046 (Hybridoma NOK3), FERM BP-5047 (Hybridoma NOK4) and FERM BP-5048 (Hybridoma NOK5) in National Institute of Bioscience and Human-Technology, Agency of Industrial Science and Technology. On the other hand, examples of the monoclonal antibodies against mouse Fas ligand include a monoclonal antibody produced by a hybridoma cell line deposited as Accession No. FERM BP-5334 (Hybridoma KAY-10) in National Institute of Bioscience and Human-Technology, Agency of Industrial Science and Technology.

Examples of other monoclonal antibodies according to the present invention, which specifically react with a Fas ligand, include antibodies the classes or subclasses of which are mouse $IgG_1$, mouse $IgG_{2a}$, mouse IgM and mouse $IgG_3$, respectively.

The antibodies according to the present invention are useful not only for immunochemical researches, but also for immunotherapy, immunodiagnoses and the like. In order to achieve such objects, it is not always necessary to use the whole antibody molecule. A part of the molecule may be used so far as it is active. As easily understood by those skilled in the art, in some cases, it may be more preferable to use such a part of the molecule. Accordingly, the present invention also includes active fragments of the anti-Fas ligand antibodies. An antibody is a homogeneous immunoglobulin which recognizes a specific antigenic substance. The term "active fragment" means a fragment of an antibody active in antigen-antibody reaction. As specific examples thereof, may be mentioned $F(ab')_2$, Fab', Fab, Fv and recombinant Fv.

The $F(ab')_2$ fragment is one of fragments obtained by digesting an immunoglobulin IgG with pepsin. When IgG is subjected to pepsin digestion at a pH near 4.0, it is cleaved at a hinge area of its H chain to produce a fragment having a molecular weight of about 100,000. This cleavage takes place on the C-terminal side away from the disulfide bond between H chains. This fragment has two antigen-binding sites and hence can bind to antigens, thereby undergoing precipitin reaction and agglutination reaction. The Fab' fragment is a fragment produced by reducing the $F(ab')_2$ fragment with a reagent such as 2-mercaptoethanol and alkylating the reduced product with monoiodoacetic acid, thereby cleaving a disulfide bond between H chains, and having a molecular weight of about 50,000.

The Fab fragment (antigen-binding fragment) is one of fragments obtained by the papain digestion of IgG. When IgG is subjected to papain digestion in the presence of cysteine, its H chain is cleaved at a site on the N-terminal side away from the disulfide bond between H chains in a hinge area, thereby producing two Fab fragments and one Fc fragment (crystallizable fragment). The Fab fragment is a fragment in which an Fd fragment ($V_H$ domain+$C_H1$ domain) corresponding to about a half of the H chain on the N-terminal side is coupled to an L chain by a disulfide bond, said fragment having a molecular weight of about 45,000. The Fab fragment has one antigen-binding site. The Fv fragment is an antigen-binding fragment composed of a variable region of immunoglobulin heavy chain ($V_H$) and a variable region of immunoglobulin light chain ($V_L$), said variable regions being coupled to each other by a nonconjugate bond.

The recombinant Fv fragment can be obtained by sequencing a DNA from a hybridoma which produces a monoclonal antibody to determine base sequences which encode $V_H$ and $L_H$, respectively, and then integrating these DNA fragments in a vector to produce a monovalent active antibody fragment having a structure of $V_L$-Linker-$V_H$. In IgG, Fab or $F(ab')_2$. $V_H$ and $L_H$ are coupled to each other by an S—S bond. In the recombinant Fv fragment, a linker is inserted between $V_H$ and $L_H$ so as to take the same configuration as the state coupled by the S—S bond. This fragment may be simply called "Fv" in some cases. It may also be called "scFv (single chain FV)". The recombinant Fv fragment may also be expressed by microorganisms such as *Escherichia coli* and bacteriophages.

Although these fragments may be used singly, they may be bound to a substance such as albumin or polyethylene glycol to use them in the form of new complexes. In general, such a complex often exhibits its effect up to the maximum without being decomposed for a long period of time in vivo. A method of adding the substance such as albumin or polyethylene glycol to the active fragment is described in, for example, Antibodies, A. Laboratory Manual, Cold Spring Harbor Laboratory, 1988. In general, the use of a divalent reaction reagent such as SPDP (product of Pharmacia) permits easily binding the active fragment to albumin or the like.

Humanized antibodies may also be provided by such methods as, for example, a mouse-derived active fragment is used to replace a primary structure other than regions (for example, hypervariable regions) necessary to react with a Fas ligand in both H chain and L chain by its corresponding primary structure in a human antibody.

The monoclonal antibodies according to the present invention, and the hybridomas separately producing these monoclonal antibodies can be produced in accordance with the following process.

(1) An animal (for example, a rodent such as a mouse) not expressed with a functional Fas molecule is immunosensitized with cells (for example, COS cells) which have expressed a Fas ligand molecule or Fas ligand.

(2) Antibody-producing cells are prepared from the immunosensitized animal to form a suspension thereof. Splenocytes or lymphadenocytes are mainly used. However, peripheral lymphocytes may also be used. When splenocytes are used, the spleen is taken out of the immunosensitized rodent to form a suspension of splenocytes.

(3) The suspension of the antibody-producing cells is mixed with myeloma cells to fuse both cells. For example, the suspension of the splenocytes is mixed with myeloma cells of a mouse in the presence of a hybridization accelerator (for example, polyethylene glycol) to fuse both cells. The cell fusion may be conducted by an electrical treatment. As the myeloma cells used herein, those (for example, 8-azaguanine-resistant strain) distinguishable from the antibody-producing cells in a subsequent selective culture are used.

(4) The fused cells are diluted with a medium which does not favor unfused myeloma cells to culture the fused cells, thereby sorting hybridomas produced by the fusion of the antibody-producing cell with the myeloma cell. More specifically, the fused cells are cultured in a selective medium in which the antibody-producing cells are viable, but the myeloma cells are killed, thereby sorting hybridomas produced by the fusion of the antibody-producing cell with the myeloma cell. For example, when 8-azaguanine-resistant myeloma cells are used, an HAT medium (hypoxanthine-aminopterine-thymidine containing medium) is used.

(5) Whether antibodies secreted in a culture supernatant containing the hybridomas are against the desired antigen or not is determined using, as an indicator, the fact that the antibodies inhibit the attack of a Fas ligand present in a supernatant of Fas ligand-expressed cells (for example, COS cells) against Fas-expressed cells.

(6) A series of cells in culture wells in which cells secreting the desired antibodies exist is cloned. The cloning is generally performed by the limiting dilution technique.

(7) A clone from which the desired antibody is secreted is selected.

(8) Cloning is conducted again to establish a hybridoma clone which secretes a monoclonal antibody against the desired antigen.

(9) A monoclonal antibody is prepared from a culture supernatant of the hybridoma or ascites fluid obtained by intraperitoneally administering the hybridoma to a mouse (for example, a nude mouse).

More specifically, the monoclonal antibodies according to the present invention, and the hybridomas separately producing these monoclonal antibodies can be produced in accordance with the following process.

(1) Preparation of Fas ligand-expressed COS cells:

The gene of a human Fas ligand can be obtained by reference to the sequence described in S. Nagata et al., Int. Immunol. Vol. 6, No. 10, pp. 1567–1574. More specifically, respective complementary DNA primers as to both 5'-terminal and 3'-terminal sides of the Fas ligand cDNA were synthesized. Based on these primers, an amplification reaction was conducted in accordance with the PCR technique using, as a template, a cDNA prepared from human killer T cells and containing a Fas ligand, and the resultant cDNA was then transfected into a vector, PMKitNeo. This Fas ligand gene-transfected vector was transfected into COS cells (ATCC CRL 1650) in accordance with the DEAE-dextran method to prepare human Fas ligand-expressed COS cells.

(2) Immunosensitization:

A rodent (for example, MRL 1pr/1pr mouse) is immunosensitized with the Fas ligand-expressed COS cells as an antigen. The reason why MRL 1pr/1pr is used is that rodents including mice are observed expressing Fas in many tissues. Therefore, when a rodent such as a mouse is immunosensitized using, as an immunogen (=an antigen), Fas ligand-expressed cells, a signal of death mediated by Fas is inserted, resulting in killing the individual animal. It is therefore inconvenient to use such a rodent. As apparent from the report by Dr. Nagata et al. (Nature. Vol. 356, pp. 314–317, 1992), MRL 1pr/1pr does not express a functional Fas. Therefore, if the MRL 1pr/1pr mouse is inoculated with Fas ligand-expressed cells, the mouse is not killed, and so sufficient immunosensitization is feasible.

In addition, a CBA/1prc$^{cg}$ mouse may be used. This mouse normally expresses a Fas antigen. However, since the mouse has a point mutation in the intracellular region of the Fas antigen gene, it undergoes transfer aberration of an apoptotic signal mediated by Fas. Those skilled in the art may artificially produce Fas-defective mice other than these mice in view of the present techniques of molecular biology, of course.

As described above, the MRL gld mouse is a mouse having a mutation of Fas ligand, so that a Fas ligand cannot function therein. When this mouse is immunized with cells having a normal Fas ligand or a Fas ligand molecule, an antibody which recognizes a region necessary for the function of the Fas ligand can be obtained. The reason for it is that a difference between a normal Fas ligand and a mutant Fas ligand is only one site in terms of amino acid, and the MRL gld mouse has a high possibility that it may recognize this difference as an antigen, and so an antibody against the function of the Fas ligand is easy to be produced. Incidentally, as described in the literature by Nagata et al., Cell, Vol. 76, pp. 969–976 (1994), a difference between the normal Fas ligand and the mutant Fas ligand is such that only the No. 273 amino acid in the extracellular domain of a mouse Fas ligand is changed from phenylalanine to leucine.

The various mice described above are suitable for use in providing antibodies against Fas ligand, which were produced in this time. In this experiment, the MRL 1pr/1pr mice were used.

(3) The spleen is taken out of the immunosensitized rodent to form a suspension of splenocytes.

(4) The splenocytes of the immunosensitized mouse are mixed with myeloma cells of a mouse in the presence of a hybridization accelerator (for example, polyethylene glycol) to fuse both cells. As the myeloma cells, those (for example, 8-azaguanine-resistant strain) distinguishable from the antibody-producing cells in a subsequent selective culture are used.

(5) The fused cells are diluted with a medium which does not favor unfused myeloma cells to culture the fused cells, thereby sorting hybridomas produced by the fusion of the antibody-producing cell with the myeloma cell. More specifically, the fused cells are cultured in a selective medium (for example, an HAT medium) in which the antibody-producing cells are viable, but the myeloma cells are killed, thereby selectively culturing hybridomas produced by the fusion of the cell producing the intended antibody with the myeloma cell.

(6) The presence of an antibody in a supernatant in each of culture wells separately containing the hybridomas is confirmed using, as an indicator, the fact that the antibodies inhibit the attack of a Fas ligand present in a supernatant of Fas ligand-expressed COS cells against Fas-expressed cells, namely, that killer activity is blocked. More specifically, there is a method in which a supernatant in each of culture wells separately containing hybridomas is first reacted with the Fas ligand, and a transfectant which expresses a Fas antigen on a cell surface is then used as a target to determine whether the killer activity of the Fas ligand is blocked or not, thereby sorting hybridomas in culture supernatants which have blocked the killer activity. As the Fas ligand-expressed cells, for example, Fas ligand-expressed L5178Y cell may be used.

(7) After the hybridomas which separately produce the desired antibody are selected, they are monocloned by the limiting dilution technique.

(8) A monoclonal antibody is collected from a culture supernatant of the monoclone.

The monoclonal antibodies according to the present invention are antibodies which specifically react with a Fas ligand. The species of the Fas ligand is preferably the human or a mouse. In Examples which will be described subsequently, a human Fas ligand gene is used to prepare Fas ligand-expressed COS cells in accordance with a genetic engineering technique, thereby obtaining monoclonal antibodies of mouse origin.

The monoclonal antibody according to the present invention is a monoclonal antibody produced by, for example, any one of the hybridoma cell lines deposited as Accession Nos. FERM BP-5044 (Hybridoma NOK1), FERM BP-5045 (Hybridoma NOK2), FERM BP-5046 (Hybridoma NOK3), FERM BP-5047 (Hybridoma NOK4) and FERM BP-5048 (Hybridoma NOK5) in National Institute of Bioscience and Human-Technology, Agency of Industrial Science and Technology. On the other hand, the monoclonal antibody against mouse Fas ligand is a monoclonal antibody produced by, for example, the hybridoma cell line deposited as Accession No. FERM BP-5334 (Hybridoma KAY-10) in National Institute of Bioscience and Human-Technology, Agency of Industrial Science and Technology.

The monoclonal antibodies according to the present invention preferably react specifically with a human Fas ligand. The monoclonal antibodies according to the present invention preferably also react specifically with a monkey Fas ligand. Accordingly, the monoclonal antibodies according to the present Invention can preferably inhibit the physiological reaction of a human or monkey Fas ligand with Fas. However, they do preferably not inhibit the physiological reaction of a mouse Fas ligand with Fas. A representative example of the inhibition of the physiological reaction between the Fas ligand and Fas is the inhibition of apoptosis of Fas-expressed cells induced by a soluble Fas ligand secreted by the Fas ligand-expressed cells.

The monoclonal antibodies according to the present invention can react with an amino acid sequence region set forth in SEQ ID NO:31 of SEQUENCE LISTING in the extracellular region of the Fas ligand.

The monoclonal antibodies according to the present invention can inhibit apoptosis of Fas-expressed cells induced by a soluble Fas ligand at an apoptosis inhibition rate of at least 90%. The term "apoptosis inhibition rate" as used herein means a survival rate of target cells, to which an antibody has been added, in a cytotoxic reaction test in which a soluble Fas ligand contained in a 12-fold dilution of a culture supernatant of Fas ligand gene-transfected cells is used as an effector molecule, and on the other hand, Fas gene-transfected cells are used as target cells, and both are reacted in a reaction system of 100 µl in a 96-well plate to determine the survival rate of the target cells after 16 hours using a reagent for detecting viable cell numbers.

The survival rate (i.e., apoptosis inhibition rate) of the target cells can be enhanced to at least 90% when the monoclonal antibody is a monoclonal antibody produced by any one of the hybridomas NOK1 to NOK5, the soluble Fas ligand contained in the 12-fold dilution of the culture supernatant of the Fas ligand gene-transfected cells is used as the effector molecule in an amount of 25 µl in terms of such a dilution, the Fas gene-transfected cells (Fas/WR19L) are used as the target cells in an amount of 50 µl in terms of its solution at a concentration of $2 \times 10^5$ cells/ml, and a culture supernatant of the hybridoma containing the above monoclonal antibody is used in an amount of 25 µl to mix all these components with one another, thereby conducting a reaction at 37° C. for 16 hours.

The inhibitory activity of the monoclonal antibodies according to the present invention against apoptosis is higher than that of a Fas-Ig chimera molecule. More specifically, the monoclonal antibodies according to the present invention exhibit higher inhibitory activity against apoptosis at a concentration (effective concentration) of 0.01–8 µg/ml than the Fas-Ig chimera molecule at the same concentration.

The monoclonal antibodies according to the present invention can affinity-purify a soluble Fas ligand present in a culture supernatant of Fas ligand-expressed cells. In addition, the monoclonal antibodies according to the present invention can immunoprecipitate Fas ligand molecules on Fas ligand-expressed cell surfaces or soluble Fas ligand molecules secreted in a culture solution.

Since the monoclonal antibodies according to the present invention specifically react with a Fas ligand, they can serve to elucidate signal transfer mechanism for inducing apoptosis against cells, and a Fas system. In addition, the monoclonal antibodies according to the present invention and the active fragments thereof are useful in immunotheapy and immunodiagnoses, and industrial fields associated with them. For example, the monoclonal antibody specifically reacting with a Fas ligand is reacted with cells in blood, and a secondary antibody of a fluorescent marker is further bound thereto to measure the conjugate by flow cytometry or a fluorescent microscope, thereby being able to confirm that the Fas ligand has expressed in what cells. The binding of the monoclonal antibody according to the present invention to a fluorochrome such as FITC or PE can be easily performed in accordance with a method known per se in the art. Accordingly, the monoclonal antibodies according to the present invention and the active fragments thereof are useful as reagents for diagnoses.

When the monoclonal antibody according to the present invention is reacted with tissues and the like taken out of a patient suffered from various diseases (for example, an autoimmune disease, rheumatism and hepatitis), what tissue Fas ligand-expressed cells exist in can be determined.

Since the monoclonal antibodies according to the present invention can recognize (react with) a Fas ligand on human cell surfaces or a soluble Fas ligand and also a Fas ligand on monkey cell surfaces, they are useful in investigating antibodies for treating various diseases including AIDS and viral hepatitis. In addition, they are very useful in screening new remedies because their effects can be monitored.

The monoclonal antibodies of the present invention against human Fas ligand can inhibit a physiological reaction of a human Fas ligand in that they inhibit the physiological reaction between the Fas ligand and Fas. However, they cannot inhibit a physiological reaction of a mouse Fas ligand. Therefore, they are useful in investigation with SCID mice and the like. In addition, they are also useful in specifically inhibiting or monitoring the action and the like after human cells are transplanted into a mouse.

The monoclonal antibody against mouse Fas ligand according to the present invention does not react with a mouse-derived Fas ligand classified in the same type as the type of MHC class II of a mouse immunosensitized with a Fas ligand for the purpose of providing such an antibody. The monoclonal antibody against mouse Fas ligand according to the present invention recognizes (reacts with) Fas ligands of B6 and C3H mice, but does not recognize a Fas ligand of a Balb/c mouse. The monoclonal antibody (KAY-10 antibody) against mouse Fas ligand of the present invention is that obtained by immunosensitizing an MAL gld mouse with Fas ligand-expressed COS cells. The type of MHC class II of the MAL gld mouse is $H-2^d$, and the types of MHC class II of Balb/c and DBA mice, from which a Fas ligand not reacting with KAY-10 is derived are also $H-2^d$, and they are the same. On the other hand, the MHC class II of B6 and C3H mice from which a Fas ligand reacting with KAY-10 is derived are $H-2^b$ and $H-2^k$, respectively.

A Fas ligand in a solution (blood, culture supernatant, body fluids, urine or the like) can be detected (further quantified) by using a plurality (for example, two kinds) of the monoclonal antibodies according to the present invention in combination. A preferable detection method is as follows. One of the plural monoclonal antibodies is immobilized on a carrier. The other monoclonal antibody is labeled with a labeled compound. The carrier on which the monoclonal antibody has been immobilized is immersed in a solution of a specimen which is considered to contain a Fas ligand, thereby adsorbing the specimen. The adsorbed specimen is then detected by the monoclonal antibody labeled with the labeled compound. Incidentally, an ELISA plate is preferred as the carrier.

More specifically, there is mentioned a method in which a purified monoclonal antibody of IgM type is immobilized on a plate, and a Fas ligand in a solution is detected by a biotin-labeled monoclonal antibody of IgG type. According to, for example, a method in which a purified antibody of IgM type against Fas ligand is immobilized on a plate, and a Fas ligand is detected by a biotin-labeled monoclonal antibody of IgG type against Fas ligand, a Fas ligand molecule in a solution can be detected to a concentration of 1 ng/ml.

More particularly, a solution of a purified antibody of IgM type, for example, the NOK3 antibody, prepared at a concentration of 10 μg/ml with PBS (phosphate-buffered saline) is placed in an ELISA plate in a proportion of 50 μl/well to immobilize the antibody on its bottom. A specimen (sample) which is considered to contain a soluble Fas ligand to be measured is diluted to a proper concentration with PBS or 10% FCS•RPMI 1640 medium. This sample is adsorbed on the plate on which the NOK3 antibody of IgM type has been immobilized. The soluble Fas ligand in the sample thus adsorbed is detected by the NOK1 antibody which is another antibody and has been labeled with biotin or the like.

In this detection method, ① a first antibody is immobilized on a solid phase (for example, plate), ② the remaining part, on which the antibody is not adsorbed, is blocked with a blocking agent, ③ a sample to be measured is placed to be adsorbed on the antibody, and the remainder is washed out, ④ a second antibody is labeled with a suitable substance, and this antibody is further reacted to form a complex of "antibody-substance to be measured (Fas ligand)-labeled antibody" on the solid phase, and ⑤ a fluorescent substance or light absorbing substance, which binds to the marker, is added using the marker as an indicator, thereby finally determining its fluorescence intensity or light absorption intensity.

At this time, a standard of the Fas ligand molecule is required. This can be purified by using the monoclonal antibody against Fas ligand obtained in this time. More specifically, gene-transfected cells, hFasL/L5178Y, that are L5178Y (mouse T cell line; available from ATCC) into which a human Fas ligand gene has been transfected, are cultured in a large amount in a serum-free medium. A culture supernatant is collected from the cell culture solution (to remove cells by centrifugation), and concentrated using a separating membrane or the like. Purification is performed on the basis of this concentrated solution. The purification may preferably be carried out by using an affinity column in which the monoclonal antibody against Fas ligand has been immobilized on Sepharose beads. The affinity column can be prepared by binding an antibody against Fas ligand to Sepharose beads activated with CNBr (cyanogen bromide). In such a manner, 2–3 μg of a soluble Fas ligand can be obtained from 1 liter of the culture supernatant of hFasL/L5178Y.

In addition, a kit for use in detecting a Fas ligand can be provided by using in combination a plurality (for example, two kinds) of the monoclonal antibodies against Fas ligand. An example of a kit for use in detecting a soluble Fas ligand according to the present invention includes a kit comprising the following components.

TABLE 1

| ① | 96-Well microplate | one plate |
| ② | Biotinized NOK1 antibody (5 μg/ml) | 5 ml |
| ③ | NOK3 antibody (10 μg/ml) | 5 ml |
| ④ | Blocking solution (Block Ace diluted to ½) | 20 ml |

TABLE 1-continued

| ⑤ | AB Complex solution | |
| | Solution A | 2.5 ml |
| | Solution B | 2.5 ml |
| ⑥ | Substrate solution | 10 ml |
| ⑦ | Reaction terminating solution | 10 ml |

Of course, the kit may be provided in a state that one of the antibodies has been immobilized on the 96-well microplate. Besides, the kit may easily take a form that beads on which one of the antibodies has been immobilized are used, and the beads are placed in a small test tube to conduct a reaction. The quantitative proportions of the individual components may also be suitably changed.

Such a kit for detecting a Fas ligand can detect a Fas ligand in a solution containing a Fas ligand molecule at a concentration of at least 0.4325 ng/ml. In addition, the kit according to the present invention can detect a concentration of a Fas ligand in the blood of a person attacked by, for example, infectious mononucleosis (IM), systemic lupus erythematodes (SLE) or hepatitis. Accordingly, these diseases can be diagnosed by using, as an indicator, the fact that the concentration of a Fas ligand in the blood is significantly higher than a normal person.

The present inventors have determined the amino acid sequences of variable regions of H chains (heavy chains) and L chains (light chains) of the monoclonal antibodies (anti-FasL monoclonal antibodies) against human Fas ligand, and base sequences of DNAs encoding them. More specifically, respective cDNAs were extracted from hybridomas (for example, Hybridoma NOK1 to Hybridoma NOK5) which separately produce the anti-FasL monoclonal antibodies, and respective DNAs encoding variable regions ($V_H$) of the H chains and variable regions ($V_L$) of the L chains were collected from these cDNAs in accordance with the PCR technique and mini gel electrophoresis. After culturing a transformant in which each of the DNAs has been inserted, the plasmid DNA was subjected to DNA sequensing by the dye-terminator method to determine its base sequence.

In addition, an amino acid sequence, which is encoded by each of the base sequences, was determined from such a base sequence, thereby determining the amino acid sequences of the variable regions of each anti-FasL monoclonal antibody. Further, these amino acid sequences were investigated in detail to determine the respective amino acid sequences of hypervariable regions (CDR1 to CDR3) thereof. These sequences are shown in SEQUENCE LISTING which will be described subsequently.

A site of a monoclonal antibody at which the monoclonal antibody recognizes an antigen is referred to as a variable region. In this region, a site binding to the antigen is referred to as a hypervariable region (CDR). The variable region contains 3 hypervariable regions. The hypervariable regions are conserved, and the configurations of other portions of the variable region are well maintained and exchanged so as to be closer to those of another species, thereby providing an antibody according to such another species. For example, mouse antibodies were obtained in Examples which will be described subsequently. However, the hypervariable regions of each of these antibodies are conserved, other portions of the variable region are exchanged to those close to those of the human as much as possible, and the Fc portion thereof is exchanged to that of the human, thereby permitting the provision of a humanized antibody. Recently, antibodies for treatment have been about to shift from mere chimera antibodies (the variable regions thereof have been conserved) to antibodies only the hypervariable regions of which have been conserved due to the problem of HAMA.

The determination of the amino acid sequences of the variable regions of H chains and L chains of the anti-FasL monoclonal antibodies, and the base sequences of DNAs encoding them permits the provision of the following monoclonal antibodies or active fragments thereof.

1. A monoclonal antibody which is an antibody against human Fas ligand and has the following features: (1) the inhibitory effect on apoptosis being equal to that of an antibody produced by Hybridoma NOK1 deposited as Accession No. FERM BP-5044 in National Institute of Bioscience and Human-Technology, Agency of Industrial Science and Technology; (2) the hypervariable regions of the H chain extending ① from Ser of the 30th to Asn of the 34th, ② from Arg of the 49th to Gly of the 65th and ③ from Tyr of the 93th or Ser of the 98th to Tyr of the 109th of the amino acid sequence set forth in SEQ ID NO:1 of SEQUENCE LISTING; and/or (3) the hypervariable regions of the L chain extending ① from Arg of the 24th to Asn of the 34th, ② from Tyr of the 50th to Ser of the 56th and ③ from Gln of the 89th to Thr of the 97th of the amino acid sequence set forth in SEQ ID NO:3 of SEQUENCE LISTING, or active fragments thereof.

2. A monoclonal antibody which is an antibody against human Fas ligand and has the following features: (1) the inhibitory effect on apoptosis being equal to that of an antibody produced by Hybridoma NOK2 deposited as Accession No. FERM BP-5045 in National Institute of Bioscience and Human-Technology, Agency of Industrial Science and Technology; (2) the hypervariable regions of the H chain extending ① from Asn of the 30th to Gly of the 34th, ② from Tyr of the 49th to Gly of the 65th and ③ from Tyr of the 93th or Tyr of the 98th to Tyr of the 107th of the amino acid sequence set forth in SEQ ID NO:5 of SEQUENCE LISTING; and/or (3) the hypervariable regions of the L chain extending ① from Lys of the 24th to Gly of the 39th, ② from Leu of the 55th to Ser of the 61th and ③ from Phe of the 94th or Gln of the 95th to Thr of the 102th of the amino acid sequence set forth in SEQ ID NO:7 of SEQUENCE LISTING, or active fragments thereof.

3. A monoclonal antibody which is an antibody against human Fas ligand and has the following features: (1) the inhibitory effect on apoptosis being equal to that of an antibody produced by Hybridoma NOK3 deposited as Accession No. FERM BP-5046 in National Institute of Bioscience and Human-Technology, Agency of Industrial Science and Technology; (2) the hypervariable regions of the H chain extending ① from Ser of the 30th to Asn of the 34th, ② from Arg of the 49th to Gly of the 65th and ③ from Tyr of the 93th or Asp of the 98th to Val of the 105th of the amino acid sequence set forth in SEQ ID NO:9 of SEQUENCE LISTING; and/or (3) the hypervariable regions of the L chain extending ① from Lys of the 24th to Ser of the 34th, ② from Gly of the 50th to Thr of the 56th and ③ from Val of the 89th or Gln of the 90th to Thr of the 97th of the amino acid sequence set forth in SEQ ID NO:29 of SEQUENCE LISTING, or active fragments thereof.

4. A monoclonal antibody which is an antibody against human Fas ligand and has the following features: (1) the inhibitory effect on apoptosis being equal to that of an antibody produced by Hybridoma NOK4 deposited as Accession No. FERM BP-5047 in National Institute of Bioscience and Human-Technology, Agency of Industrial Science and Technology; (2) the hypervariable regions of the H chain extending ① from Tyr of the 32th to Asn of the 35th, ② from Tyr of the 50th to Asn of the 65th and ③ from Tyr of the 93th to Tyr of the 107th of the amino acid sequence set forth in SEQ ID NO:11 of SEQUENCE LISTING; and/or (3) the hypervariable regions of the L chain extending ① from Arg of the 24th to His of the 38th, ② from Arg of the 54th to Ser of the 60th and ③ from Gin of the 93th to Thr of the 101th of the amino acid sequence set forth in SEQ ID NO:13 of SEQUENCE LISTING, or active fragments thereof.

5. A monoclonal antibody which is an antibody against human Fas ligand and has the following features: (1) the inhibitory effect on apoptosis being equal to that of an antibody produced by Hybridoma NOK5 deposited as Accession No. FERM BP-5048 in National Institute of Bioscience and Human-Technology, Agency of Industrial Science and Technology; (2) the hypervariable regions of the H chain extending ① from Thr of the 30th to His of the 34th, ② from Tyr of the 49th to Asp of the 65th and ③ from Tyr of the 93th to Tyr of the 106th of the amino acid sequence set forth in SEQ ID NO:15 of SEQUENCE LISTING; and/or (3) the hypervariable regions of the L chain extending ① from Lys of the 24th to Ala of the 34th, ② from Tyr of the 50th to Thr of the 56th and ③ from Gin of the 89th to Thr of the 97th of the amino acid sequence set forth in SEQ ID NO:17 of SEQUENCE LISTING, or active fragments thereof.

6. A monoclonal antibody which is an antibody against human Fas ligand and has the following features: (1) the inhibitory effect on apoptosis being equal to that of an antibody produced by Hybridoma NOK1 deposited as Accession No. FERM BP-5044 in National Institute of Bioscience and Human-Technology, Agency of Industrial Science and Technology; (2) the variable region of the H chain consisting of the amino acid sequence set forth in SEQ ID NO:1 (the base sequence set forth in SEQ ID NO:2) of SEQUENCE LISTING; and/or (3) the variable region of the L chain consisting of the amino acid sequence set forth in SEQ ID NO:3 (the base sequence set forth in SEQ ID NO:4) of SEQUENCE LISTING, or active fragments thereof.

7. A monoclonal antibody which is an antibody against human Fas ligand and has the following features: (1) the inhibitory effect on apoptosis being equal to that of an antibody produced by Hybridoma NOK2 deposited as Accession No. FERM BP-5045 in National Institute of Bioscience and Human-Technology, Agency of Industrial Science and Technology; (2) the variable region of the H chain consisting of the amino acid sequence set forth in SEQ ID NO:5 (the base sequence set forth in SEQ ID NO:6) of SEQUENCE LISTING; and/or (3) the variable region of the L chain consisting of the amino acid sequence set forth in SEQ ID NO:7 (the base sequence set forth in SEQ ID NO:8) of SEQUENCE LISTING, or active fragments thereof.

8. A monoclonal antibody which is an antibody against human Fas ligand and has the following features: (1) the inhibitory effect on apoptosis being equal to that of an antibody produced by Hybridoma NOK3 deposited as Accession No. FERM BP-5046 in National Institute of Bioscience and Human-Technology, Agency of Industrial Science and Technology; and (2) the variable region of the H chain consisting of the amino acid sequence set forth in SEQ ID NO:9 (the base sequence set forth in SEQ ID NO:10) of SEQUENCE LISTING, or active fragments thereof.

9. A monoclonal antibody which is an antibody against human Fas ligand and has the following features: (1) the inhibitory effect on apoptosis being equal to that of an antibody produced by Hybridoma NOK4 deposited as Accession No. FERM BP-5047 in National Institute of Bioscience and Human-Technology, Agency of Industrial Science and Technology; (2) the variable region of the H chain consisting of the amino acid sequence set forth in SEQ ID NO:11 (the base sequence set forth in SEQ ID NO:12) of SEQUENCE LISTING; and/or (3) the variable region of the L chain consisting of the amino acid sequence set forth in SEQ ID NO:13 (the base sequence set forth in SEQ ID NO:14) of SEQUENCE LISTING, or active fragments thereof.

10. A monoclonal antibody which is an antibody against human Fas ligand and has the following features: (1) the inhibitory effect on apoptosis being equal to that of an antibody produced by Hybridoma NOK5 deposited as Accession No. FERM BP-5048 in National Institute of Bioscience and Human-Technology, Agency of Industrial Science and Technology; (2) the variable region of the H chain consisting of the amino acid sequence set forth in SEQ ID NO:15 (the base sequence set forth in SEQ ID NO:16) of SEQUENCE LISTING; and/or (3) the variable region of the L chain consisting of the amino acid sequence set forth in SEQ ID NO:17 (the base sequence set forth in SEQ ID NO:18) of SEQUENCE LISTING, or active fragments thereof.

According to the present invention, there are also provided DNAs or RNAs comprising at least a portion encoding the hypervariable regions of the H chain or L chain set forth in any one of the above Items 1–5 in the above-described monoclonal antibodies or active fragments thereof.

According to the present invention, there are further provided DNAs or RNAs comprising at least a portion encoding the variable region of the H chain or L chain set forth in any one of the above Items 6–10 in the above-described monoclonal antibodies or active fragments thereof.

According to the present invention, there are still further provided mutants of the monoclonal antibodies or active fragments thereof set forth in the above Items 6–10. Specific examples of these mutants include the following mutants.

11. A mutant of a monoclonal antibody which is an antibody against human Fas ligand and has the following features: (1) the inhibitory effect on apoptosis being equal to that of an antibody produced by Hybridoma NOK1 deposited as Accession No. FERM BP-5044 in National Institute of Bioscience and Human-Technology, Agency of Industrial Science and Technology; (2) the variable region of the H chain consisting of the amino acid sequence set forth in SEQ ID NO:19 (the base sequence set forth in SEQ ID NO:20) of SEQUENCE LISTING; and/or (3) the variable region of the L chain consisting of the amino acid sequence set forth in SEQ ID NO:21 (the base sequence set forth in SEQ ID NO:22) of SEQUENCE LISTING, or active fragments thereof.

12. A mutant of a monoclonal antibody which is an antibody against human Fas ligand and has the following features: (1) the inhibitory effect on apoptosis being equal to that of an antibody produced by Hybridoma NOK2 deposited as Accession No. FERM BP-5045 in National Institute of Bioscience and Human-Technology, Agency of Industrial Science and Technology; (2) the variable region of the H chain consisting of the amino acid sequence set forth in SEQ ID NO:23 (the base sequence set forth in SEQ ID NO:24) of SEQUENCE LISTING; and/or (3) the variable region of the L chain consisting of the amino acid sequence set forth in SEQ ID NO:25 (the base sequence set forth in SEQ ID NO:26) of SEQUENCE LISTING, or active fragments thereof.

13. A mutant of a monoclonal antibody which is an antibody against human Fas ligand and has the following features: (1) the inhibitory effect on apoptosis being equal to that of an antibody produced by Hybridoma NOK3 deposited as Accession No. FERM BP-5046 in National Institute of Bioscience and Human-Technology, Agency of Industrial Science and Technology; (2) the variable region of the H chain consisting of the amino acid sequence set forth in SEQ ID NO:27 (the base sequence set forth in SEQ ID NO:28) of SEQUENCE LISTING; and/or (3) the variable region of the L chain consisting of the amino acid sequence set forth in SEQ ID NO:29 (the base sequence set forth in SEQ ID NO:30) of SEQUENCE LISTING, or active fragments thereof.

According to the present invention, there are yet still further provided DNAs or RNAs comprising at least a portion encoding the variable region of the H chain or L chain set forth in any one of the above Items 11–13 in the above-described monoclonal antibodies or active fragments thereof.

EXAMPLES

The present invention will hereinafter be described more specifically by the following Examples. However, the present invention is not limited to these examples only.

Example 1

Preparation and Characterization of Monoclonal Antibodies (1) Isolation of Fas Ligand Gene ① Preparation of Primers A human Fas ligand gene was isolated on the basis of the report by Nagata et al. More specifically, Xho I-5' FasL obtained by adding a sequence of 18mers of the 5' end of a human Fas ligand to a sequence of the Xho-I site on the 5' end side of human Fas ligand cDNA, and Not1-3' FasL obtained by adding a sequence of 18mers of the 3' end of a human Fas ligand to a sequence of the Not1 site on the 3' end side of human Fas ligand cDNA were separately subjected to DNA synthesis using Model 392 DNA/RNA synthesizer (manufactured by ABI) on a scale of 0.2 $\mu$mol. The product DNAs were purified in accordance with the protocol to prepare primers for PCR.

② Preparation of Template of Fas Ligand cDNA

A template was prepared from human killer T cells in which a human Fas ligand had been expressed. More specifically, human killer T cells were activated with PMA and ionomycin to collect $1\times10^7$ cells. The collected cells were suspended in 1 ml of RNAz01B (product of Cosmo Bio). After 100 $\mu$l of chloroform were further added to the suspension, the mixture was left to stand for 30 minutes on an ice bath. Thereafter, a phenol layer was separated from a water layer by centrifugation (at 4° C.) for 15 minutes at 15,000 rpm to recover only the upper water layer. An equiamount of isopropanol was added to the water layer, and the resultant mixture was left to stand for 30 minutes at −80° C., followed by precipitation of RNA by centrifugation (15,000 rpm, 15 minutes, 4° C.). After the precipitate thus obtained was centrifugally washed once with 1 ml of ethanol, it was suspended in 11.5 $\mu$l of water subjected to DEPC treatment. Added to this RNA suspension were 0.5 $\mu$l (0.5 mg/ml) of synthetic oligo dT, followed by a heat treatment for 10 minutes at 70° C. The mixture thus treated was then treated on an ice bath for 5 minutes.

Thereafter, 4 $\mu$l of 5×RT buffer (product of Stratagene), 1 $\mu$m of 10 mM dNTP, 2 $\mu$l of 0.1 M DTT and 1 $\mu$l of SUPERSCRIPT RTase (product of Stratagene) were added to conduct a reaction at 42° C. for 50 minutes, thereby reversely transcribing RNA into cDNA. After the reaction mixture was treated at 90° C. for 5 minute to deactivate the RTase, it was left to stand for 5 minutes on an ice bath. After 1 μl of RNaseH (product of Stratagene) was then added to this sample to conduct a reaction further for 20 minutes at 37° C., thereby decomposing unnecessary RNA to provide a template for cDNA containing Fas ligand.

③ PCR

PCR was performed by reference to PCR Experimental Manual (HBJ Press, pp. 75–85) under the following conditions.

Namely, 1 μl of 10 mM dNTPmix (product of Pharmacia), 1 μl of Xho I Site-5' human FasL of 18mers (50 μM), 1 μl of Not I-3' human FasL of 18mers (50 μM), 4 μl of 10×PCR buffer (product of Perkin-Elmer), 0.5 μl of AMPLITAQ™ (product of Perkin-Elmer) and 30.5 μl of water were added to 2 μl of the cDNA produced in Step ② into a solution of 40 μl in total. After this solution was topped with 40 μl of mineral oil (product of Sigma), an amplification reaction was carried out by means of a DNA thermal cycler for PCR (manufactured by Perkin-Elmer Japan). More specifically, the amplification reaction was carried out under conditions of successively 5 minutes at 94° C., 2 minutes at 55° C., 3 minutes at 72° C., 1 minute at 94° C., 2 minutes at 55° C. and 10 minutes at 72° C. by repeating the treatment between 2 minutes at 55° C. and 1 minute at 94° C. 30 cycles.

④ Integration into PMKitNeo Vector

After conducting the amplification reaction by PCR, only a water layer was extracted with a mixture of phenol and chloroform. Each 1.0 unit of Xho I and Not I (both, products of Boehringer Co.) were added to the extract thus obtained, and an accessory buffer was added, followed by a reaction at 37° C. for 16 hours. The reaction mixture was electrophoresed in a 1% agarose gel. A band of about 850 bp corresponding to the Fas ligand was got out of the gel under UV irradiation.

DNA was extracted from this agarose gel using a GENECLEAN II kit (product of BIO101, Funakoshi). More specifically, an accessory NaI solution was added to the gel to incubate the gel at 65° C. for 10 minutes, thereby dissolving the gel in the solution. Glass milk was then added to the solution, and the mixture was rotationally stirred for 5 minutes to adsorb DNA on the glass milk. After this glass milk was washed three times with New-WASH solution, it was suspended in 10 μof a TE buffer. The suspension was incubated at 65° C. for 3 minutes, thereby dissolving DNA out of the glass milk.

A PMKitNeo vector in an amount of 1 μg was then treated with the restriction enzymes Xho I and Not I in the same manner as described above to electrophorese it in a 0.75% agarose gel, followed by purification with the GENECLEAN II kit.

The Fas ligand cDNA and PMKitNeo vector were then ligated. More specifically, they were mixed so as to give a molar ratio of the vector to cDNA of 1:2, and the mixture was subjected to a ligation reaction at 16° C. for 16 hours using a DNA ligation kit produced by Takara Shuzo Co., Ltd.

⑤ Integration into *Escherichia coli*

The reaction mixture obtained in the step ④ was mixed with *Escherichia coli* competent cells (product of Toyobo) to incubate the mixture for 30 minutes on an ice bath and for 40 seconds at 42° C., thereby inserting DNA into *Escherichia coli*. After an SOC medium was added thereto to conduct shaking culture at 37° C. for 1 hour, the culture was poured into an LB agar medium containing ampicillin to conduct culture at 37° C. for 1 day. Thereafter, appeared colonies were cultured at 37° C. for 1 day in the LB medium, and the resultant plasmid (human Fas ligand-PMKitNeo) was then recovered by the alkali method.

(2) Transfection into COS Cell

The transfection of the plasmid (human Fas ligand-PMKitNeo) into COS cells (ATCC CRL 1650) was carried out in accordance with the DEAE-dextran method (Extra Issue of Experimental Medicine, Biomanual Series 4, Gene Transfection and Analysis of Expression, pp. 16–22, 1994, Yodo-sha). More specifically, DEAE-dextran produced by Armacia was used to perform the DEAE-dextran method in a proportion of (the human Fas ligand-PMKitNeo 5 μl)/(2× $10^6$ COS cells), thereby obtaining Fas ligand-expressed COS cells.

(3) Immunosensitization

A suspension of the Fas ligand-expressed COS cells prepared in the step (2) was intraperitoneally injected into a Balb/c mouse in a proportion of $1 \times 10^7$ cells/mouse. After a week, the suspension of the Fas ligand-expressed COS cells was injected in the same mouse once a week, 3 times in total, thereby immunosensitizing the mouse.

(4) Cell Fusion

After 3 days from the final immunization, the spleen was taken out of the mouse. The spleen was minced, filtered through a mesh and then suspended in an RPMI 1640 medium (product of Nissui), thereby obtaining $1 \times 10^8$ splenocytes. The splenocytes and a mouse-derived 8-azaguanine-resistant strain (hypoxanthine-guanine phosphoribosyl transferase defective strain) P3X63Ag8.653 (ATCC CRL 1580) ($1 \times 10^7$ cells) were mixed with each other in a proportion of about 5:1, and the resulting mixture was centrifuged (1500 rpm, 5 minutes).

To the cell pellet thus obtained, 2 ml of a 50% solution of polyethylene glycol 4000 (product of Merck) in an RPMI 1640 medium were added over 1 minute with stirring on a hot water bath of 37° C. Added to the resulting mixture were 15 ml of an RPMI 1640 medium over 6 minutes with stirring, thereby conducting cell fusion. After the cell fusion, a great amount (about 40 ml) of an RPMI 1640 medium was added, and the mixture was centrifuged (1500 rpm, 5 minutes) to remove a supernatant. The splenocytes were then adjusted to $1 \times 10^6$ cells/ml with a 10% FCS (fetal calf serum)-RPMI 1640 medium (HAT medium) containing hypoxanthine (100 μM), aminopterine (0.4 μM) and thymidine (10 μM).

(5) Selection of Hybridoma

The cell suspension prepared in the step (4) was poured in 200-μl portions into 10 microplates each having 96 wells to culture the cells in a $CO_2$-incubator controlled at 37° C. and $CO_2$ concentration of 5%. After a week, it was confirmed that only hybridomas formed colonies and proliferated.

(6) Sorting of Hybridomas

A culture supernatant of the Fas ligand-expressed COS cells was used as an effector molecule, and a transfectant which expresses a Fas antigen on a cell surface was used as a target to sort out hybridomas in the culture supernatants which blocked the killer activity of the Fas ligand molecule against the transfectant.

① Preparation of Soluble Fas Ligand Molecule

A soluble Fas ligand molecule present in the culture supernatant of the Fas ligand-expressed COS cells was used as the Fas ligand molecule. More specifically, after Fas ligand-PMKIT$_{neo}$ was transfected into COS cells by the DEAE-dextran method, the cells were cultured with 100 ml of a 10% FCS-DME medium for a week, followed by collection of a culture supernatant thereof. The supernatant was sterilized through a filter having a pore size of 0.45 µm, thereby providing it as the soluble Fas ligand molecule.

② Preparation of Target Cells

WR19L cells in which a human Fas gene had been transfected were used as the target cells. The transfection of the human Fas gene into WR19L (ATCC TIB52) (Deposited as Accession Number FERM BP-6909, in National Institute of Bioscience and Human Technology, Agency of Industrial Science and Technology) was performed in accordance with a method known per se in the art. More specifically, the cells were prepared by reference to literature by Hanabuchi et al. (Proc. Natl. Acad. Sci. USA, Vol. 91, No. 11, pp. 4930–4934, 1994). The Fas-WR19L cells thus obtained were cultured and adjusted to $2 \times 10^5$ cells/ml with a 10% FCS•RPMI medium.

③ Screening Assay

The soluble Fas ligand molecule prepared in the step ① was first diluted to 1/12 with a 10% FCS-DME medium. A 96-well flat-bottomed plate (manufacture by Corning) was used to add 25 µl of the diluted solution and 25 µl of the culture supernatant of the hybridoma to each well, followed by incubation at 37° C. for 1 hour. Thereafter, the Fas-WR19L cells prepared in the step 2 were added in a proportion of 50 µl/well and incubated for 12 hours under conditions of 37° C. and 5% $CO_2$.

An ALMAR BLUE™ assay kit (product of Kanto Chemical Co.) was used to determine survival cell rate (regarding a control containing no antibody or Fas ligand as 100%), thereby selecting hybridomas in wells which inhibited the killer activity of the soluble Fas ligand molecule against the Fas-WR19L cells.

(7) Cloning

The antibody-producing cells (hybridomas) were separately poured into wells of a 96-well microplate by the limiting dilution technique so as to give a cell concentration of one cell/well to culture each cell. After culturing for 10 days, the proliferation of a single colony could be confirmed. Therefore, the process of detecting the antibody by the blocking of killer activity was performed again. As a result, clones reacting specifically with the Fas ligand were obtained. An antibody was recovered from a culture supernatant containing the hybridoma of a monoclone, thereby obtaining a monoclonal antibody which specifically reacts with the intended Fas ligand.

The thus-obtained hybridomas which separately produce a monoclonal antibody were named "NOK". Examples thereof may include hybridoma cell lines deposited as Accession Nos. FERM BP-5044 (NOK1), FERM BP-5045 (NOK2), FERM BP-5046 (NOK3), FERM BP-5047 (NOK4) and FERM BP-5048 (NOK5) in National Institute of Bioscience and Human-Technology, Agency of Industrial Science and Technology.

(8) Characterization of Monoclonal Antibody Characterization ① (Staining of FasL-Expressed Cell)

Whether an antibody produced by the thus-obtained hybridoma, for example, the cell line NOK5, reacts with a Fas ligand expressed on a cell surface or not was investigated by comparing the Fas ligand-expressed L5178Y cells with the L5178Y cells (ATCC CRL 1723) which are a parent strain thereof.

A method of transfecting a human Fas ligand gene into L5178Y (preparing FasL-L5178Y) is as follows.

Namely, each 1.0 unit of restriction enzymes, Xho I and Not I (both, products of Boehringer Co.) were added to 1 µg of the human Fas ligand gene integrated into PMKit Neo, and an accessory buffer was added, followed by a reaction at 37° C. for 2 hours. The reaction mixture was electrophoresed in a 1% agarose gel. A band of about 850 bp corresponding to the Fas ligand was got out of the gel under UV irradiation.

DNA was extracted from this agarose gel using a GENECLEAN II kit (product of BIO101, Funakoshi). More specifically, an accessory NaI solution was added to the gel to incubate the gel at 65° C. for 10 minutes, thereby dissolving the gel in the solution. Glass milk was then added to the solution, and the mixture was rotationally stirred for 5 minutes to adsorb DNA on the glass milk. After this glass milk was washed three times with New-WASH solution, it was suspended in 10 µl of a TE buffer. The suspension was incubated at 65° C. for 3 minutes, thereby dissolving DNA out of the glass milk. A $BCMGS_{neo}$ vector in an amount of 1 µg was then treated with the restriction enzymes Xho I and Not I in the same manner as described above to electrophorese it in a 0.75% agarose gel, followed by purification with the GENECLEAN II kit.

The Fas ligand cDNA and $BCMGS_{neo}$ vector were then ligated by mixing them so as to give a molar ratio of the vector to cDNA of 1:2, and subjecting the mixture to a ligation reaction at 16° C. for 16 hours using a DNA ligation kit produced by Takara Shuzo Co., Ltd.

The reaction mixture thus obtained was mixed with *Escherichia coli* competent cells (product of Toyobo) to incubate the mixture for 30 minutes on an ice bath and for 40 seconds at 42° C., thereby inserting DNA into *Escherichia coli*. After an SOC medium was added thereto to conduct shaking culture at 37° C. for 1 hour, the culture was poured into an LB agar medium containing ampicillin to conduct culture at 37° C. for 1 day. Thereafter, appeared colonies were cultured at 37° C. for 1 day in the LB medium, and the resultant plasmid (human Fas ligand-$BCMGS_{neo}$) was then recovered by the alkali method.

The transfection of this human Fas ligand-$BCMGS_{neo}$ into L5178Y cells was carried out in a proportion of (the human Fas ligand-$BCMGS_{neo}$ 1 µg)/($1 \times 10^6$ L5178Y cells) in accordance with the electro oration method under conditions that a GENE PULSER (manufacture by Bio-Rad) was used at 296 V and 960 µF. The cells were suspended again in 5 ml of a 10% FCS•RPMI 1640 medium. The suspension of the cells was poured into a 6-well plate to conduct culture. At this time, G418 (product of GIBCO) was added so as to give a concentration of 0.4 mg/ml. After 10 days from the culture, colonies were obtained, so that cells were cloned by the limiting dilution technique. A clone having the highest human Fas ligand mRNA content was sorted from the thus-obtained clones by the northern hybridization technique and cultured. The cells thus obtained were regarded as the Fas ligand-L5178Y cells.

The L5178Y cells and Fas ligand-L5178Y cells were separately adjusted to $1 \times 10^6$ cells/ml with PBS. These cells (each. $1 \times 10^6$ cells) were placed into tubes (Falcon No. 2008). Then, 100 µl of a culture supernatant of Hybridoma NOK5 were placed to conduct a reaction for 30 minutes on a water bath. The reaction mixtures were then centrifugally washed (1500 rpm, 1 minute, twice) with PBS, and 1 µl of FITC-anti-mouse Ig's (product of Cosmo Bio/Cappel) was added to conduct a further reaction for 20 minutes on an ice bath. After the reaction, the reaction mixture was centrifugally washed twice with PBS and suspended in 200 µl of PBS, followed by determination by means of an FACScan.

Figure 1:
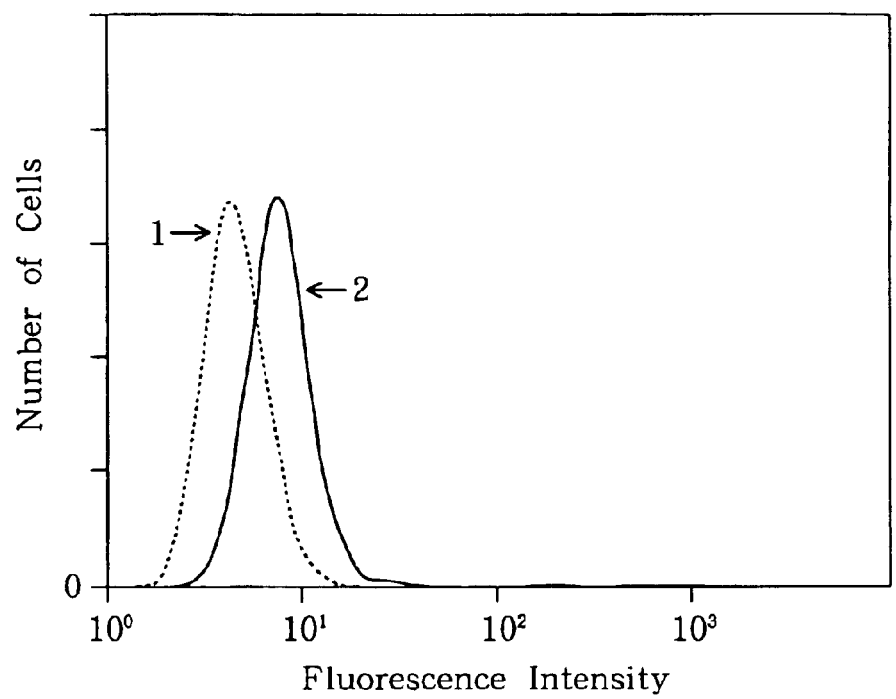
FIG. 1 is an FACScan chart illustrating stain patterns of Fas ligand-L5178Y cells, wherein reference numerals 1 and 2 represent the cases where "no NOK5 antibody was added" and "an NOK5 antibody was added", respectively.
Figure 2:
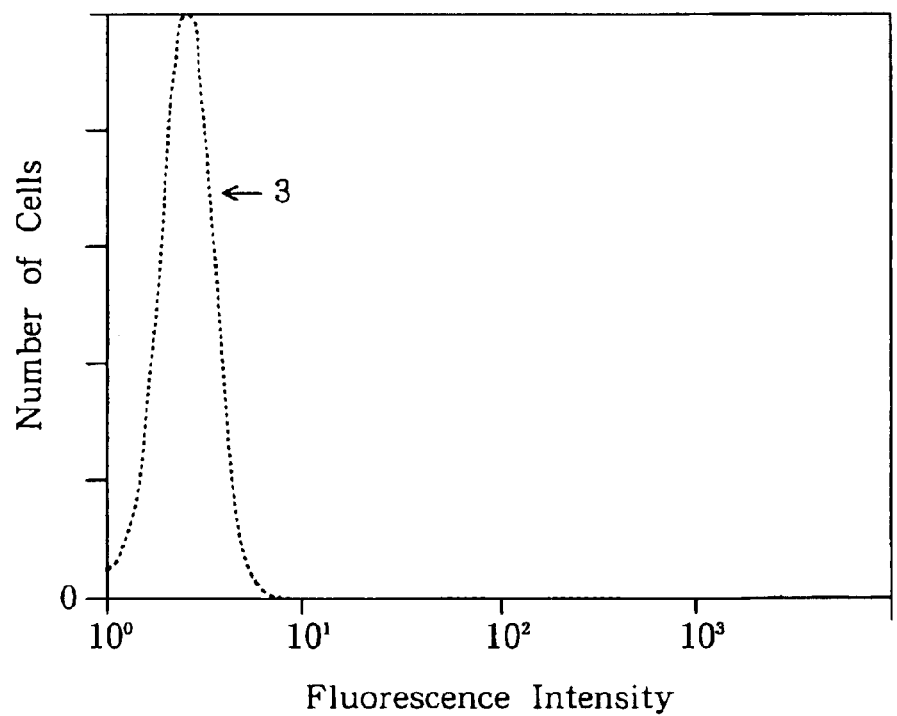
FIG. 2 is an FACScan chart illustrating a stain pattern of a parent L5178Y strain in the case where no NOK5 antibody was added, wherein reference numeral 3 represents the case where "no NOK5 antibody was added".
Figure 3:
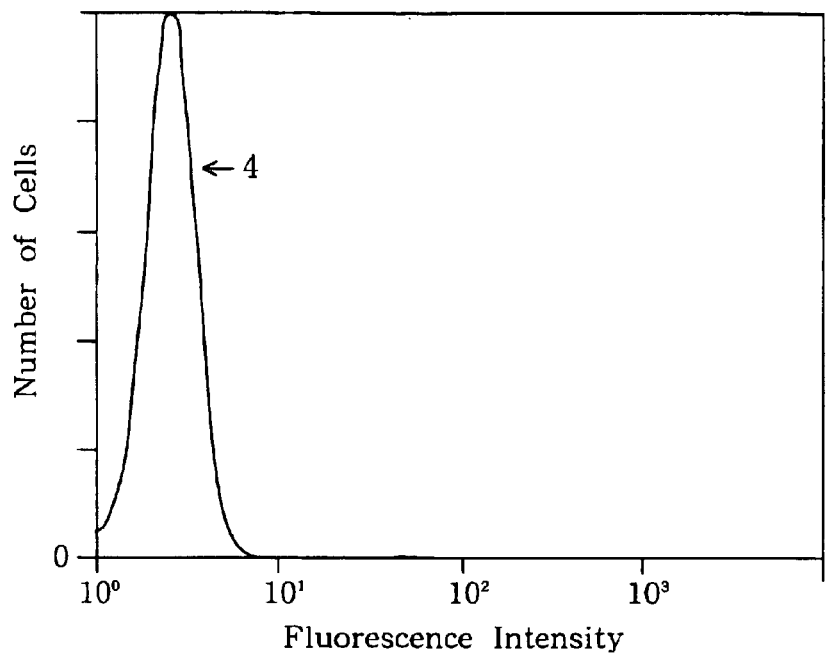
FIG. 3 is an FACScan chart illustrating a stain pattern of the parent L5178Y strain in the case where an NOK5 antibody was added, wherein reference numeral 4 represents the case where "an NOK5 antibody was added".

As a result, it was revealed that the antibody produced by NOK5 reacts with the Fas ligand-expressed L5178Y cells, but does not react with the L5178Y cells of the parent strain thereof as illustrated in FIGS. 1 to 3. Namely, as illustrated in FIGS. 2 and 3, the stain patterns of the parent L5178Y cell strain do not differ from each other irrespective of the addition of the NOK5 antibody. As illustrated in FIG. 1, however, the stain patterns of the Fas ligand-L5178Y cells clearly differ from each other depending on whether the NOK5 antibody is added or not.

The use of the cell lines of NOK1 to NOK4 achieved the same results as those in the above-described NOK5.

Characterization ② (Determination of Subclass)

Subclasses of monoclonal antibodies produced by the hybridomas NOK1 to NOK5 were determined.

The subclasses were determined by using MAB typing kits (products of PharMingen Co.) in accordance with the accessory protocol. As a result, the subclasses of NOK1, NOK2, NOK3. NOK4 and NOK5 were mouse $IgG_1$, mouse $IgG_{2a}$, mouse IgM, mouse $IgG_3$ and mouse $IgG_{2a}$, respectively.

Characterization ③

As described above, the ALMAR BLUE™ assay kit (products of Kanto Chemical Co.) was used to determine the survival cell rate, thereby selecting hybridomas in wells which inhibited the killer activity of the soluble Fas ligand molecule against the Fas-WR19L cells. When the measurement was carried out in accordance with the method described above in the step (6) ①–③, the monoclonal antibodies separately produced by the hybridomas NOK1 to NOK5 inhibit the killer activity of the soluble Fas ligand molecule against the Fas-WR19L cells at a high rate of at least 90%, preferably at least 98% as shown in the following Table. Namely, the apoptosis inhibition rates of these antibodies are at least 90%, preferably at least 98%.

TABLE 2

| Clone | Survival rate |
| --- | --- |
| No addition of any antibody | 3.5% |
| Addition of culture supernatant of NOK1 | 99.3% |
| Addition of culture supernatant of NOK2 | 105.2% |
| Addition of culture supernatant of NOK3 | 101.0% |
| Addition of culture supernatant of NOK4 | 109.8% |
| Addition of culture supernatant of NOK5 | 98.2% |

Example 2

Characterization of Monoclonal Antibodies

The characteristics of the respective monoclonal antibodies secreted by the hybridomas NOK1 to NOK3 were further investigated by the following methods.

(1) Preparation of Purified Antibodies

① Each of the hybridomas NOK1 to NOK3 was proliferated to $3 \times 10^7$ cells in an RPMI 1640 medium containing 10% FCS. The $3 \times 10^7$ cells were prepared on a scale that 30 ml of the culture solution was placed in a 75-cm² flask (product of Falcon) to conduct cell culture. Specifically, the culture was started at a concentration of $2 \times 10^5$ cells/ml, and cells were collected when reaching a concentration of $1 \times 10^6$ cells/ml.

② In each of NOK1 to NOK3, the hybridoma thus collected was suspended in 1.5 ml of PBS, and 0.5 ml (corresponding to 1×10 7 cells) of the suspension was intraperitoneally administered to nude mice. After breeding for 10 days, ascites fluid stored in their abdominal cavities was collected.

③ The amounts of the ascites fluid collected were 6.9 ml/mouse for NOK1, 6.7 ml/mouse for NOK2 and 7.4 ml/mouse for NOK3. Each 10 ml of the ascites fluid were used to purify its corresponding monoclonal antibody.

④ The purification was started from the salting-out with ammonium sulfate in which 10 ml (equiamount) of saturated ammonium sulfate were added dropwise to the ascites fluid to mix them. After the mixture was stirred at 4° C. for 2 hours, it was centrifuged for 15 minutes at 10,000 g. After removing the resultant supernatant, the precipitate was dissolved in 5 ml of PBS. The solution was dialyzed against 3 liters of PBS for 1 day.

⑤ With respect to NOX1 and NOK2, after each dialyzed sample was recovered, only IgG adsorbed on protein G was purified using a Protein G column (manufactured by Pharmacia) by an FPLC system. This sample was further dialyzed against PBS for a day. On the next day, the quantification of protein concentration and the purity test thereof were performed. With respect to NOK3, after the dialyzed sample was recovered, it was subjected to gel filtration using a SUPERDEX 200 (product of Pharmacia) column for gel filtration by an FPLC system, and IgM come out in the void volume was collected. The IgM thus collected was also investigated as to the quantification of protein and purity thereof.

The quantification of protein was conducted using a protein assay reagent produced by Bio-Rad, and the purity was determined by conducting SDS electrophoresis under reducing conditions. Thereafter, each of the antibodies NOK1 to NOK3 was adjusted to 1 mg/ml with PBS and then sterilized through a filter having a pore size of 0.2 μm.

(2) Cytotoxic Reaction

① Preparation of Soluble Fas Ligand Molecule

A soluble Fas ligand molecule present in the culture supernatant of the Fas ligand-expressed COS cells was used as the Fas ligand molecule. More specifically, after Fas ligand-PMKit $N_{eo}$ was transfected into COS cells by the DEAE-dextran method, the cells were cultured with 100 ml of a 10% FCS-DME medium for a week, followed by collection of a culture supernatant thereof. The supernatant was sterilized through a filter having a pore size of 0.45 μm, thereby providing it as the soluble Fas ligand molecule.

② Preparation of Antibody Against Fas Ligand

With respect to each of the respective antibodies produced by the hybridomas NOK1 to NOK3, 13 solutions of different concentrations were prepared with a 10% FCS-RPMI 1640 medium. The concentrations of the antibody were 32 μg/ml, 16 μg/ml, 8 μg/ml. 4 μg/ml, 2 μl/ml, 1 μg/ml, 0.5 μg/ml, 0.25 μg/ml, 0.125 μg/ml, 0.0625 μl/ml, 0.03125 μg/ml, 0.015625 μl/ml and 0.0078125 μl/ml. The solutions of these concentrations were separately prepared by 1 ml.

Incidentally, these antibodies were separately placed in 100 μl of a reaction system in an amount of 25 μl corresponding to a fourth of the original volume. Therefore, the final effective concentration of each solution amounted to a fourth of its corresponding original concentration.

③ Preparation of Fas-Ig

How to prepare Fas-Ig is described in detail in the literature by Yagita and Okumura who are co-inventors of the present application, et al. (Hanabuchi et al., Proc. Natl. Acad. Sci. USA, Vol. 91, No. 11, pp. 4930–4934, 1994). In this embodiment, the same method as in such literature was used.

More specifically, sequences of both ends of a region corresponding to an extracellular domain of Fas as to Fas cDNA were used as primers for PCR. Based on these primers, the extracellular domain of Fas was amplified by PCR to subclone it to a vector, pBluescript II, in which Fc of human immunoglobulin IgG had been transfected. Thereafter, a Fas-Ig fragment was recovered from this vector and integrated into a CDM8-expressed vector. The Fas-Ig/

CDM8 vector was transfected into COS cells to culture the cells. After about 10 days, a culture supernatant was collected. The culture supernatant was purified using a Protein A SEPHAROSE beads column (product of Pharmacia). The purified supernatant was dialyzed against PBS, adjusted to 1 mg/ml and then sterilized through a filter having a pore size of 0.2 μm. As with the antibodies NOK1 to NOK3 against Fas ligand, this Fag-Ig was prepared into 13 solutions of different concentrations ranging from 32 μg/ml to 0.0078125 μg/ml.

④ Preparation of Target Cell

WR19L cells in which a human Fas gene had been transfected were used as the target cells. The transfection of the human Fas gene into WR19L (ATCC TIB52) was performed in accordance with a method known per se in the art. More specifically, the cells were prepared by reference to literature by Yagita and Okumura who are co-inventors of the present application, and by Hanabuchi et al. (Proc. Natl. Acad. Sci. USA, Vol. 91, No. 11, pp. 4930–4934, 1994). The Fas-WR19L cells thus obtained were cultured and adjusted to $2 \times 10^5$ cells/ml with a 10% FCS•RPMI medium.

⑤ Cytotoxic Reaction

The soluble Fas ligand molecule prepared in the step ① was first diluted to 1/12 with a 10% FCS-DME medium. A 96-well flat-bottomed plate was used to add 25 μl of the diluted solution to each well. The solutions of the antibodies NOK1 to NOK 3 against Fas ligand and Fas-Ig, which had the respective concentrations, were then added to each 3 wells in a proportion of 25 μl/well. Thereafter, each well was incubated for 1 hour under conditions of 37° C. and 5% $CO_2$. Thereafter, the Fas-WR19L cells prepared in the step ④ were added in a proportion of 50 μl/well and incubated for 12 hours under conditions of 37° C. and 5% $CO_2$. Thereafter, 10 μl of 1/10 vol ALMAR BLUE™ available from Cosmo-Bio) was placed in each well, followed by a further incubation for 4 hours under conditions of 37° C. and 5% $CO_2$. Thereafter, a FLUOROSCAN II (manufactured by Titertec) fluorescent microplate reader was used to measure fluorescence.

A culture prepared by adding 50 μl of a 10% FCS-RPMI 1640 medium to a well containing 50 μl of Fas-WR19L cells, but containing none of the soluble Fas ligand, antibody and Fas-Ig was regarded as a control for the survival rate of 100%, while a culture prepared by adding 25 μl of a 10% FCS-RPMI 1640 medium and 50 μl of Fas-WR19L cells to 25 μl of the soluble Fas ligand was regarded as a control for apoptosis. The results are shown in FIG. 4.

Figure 4:
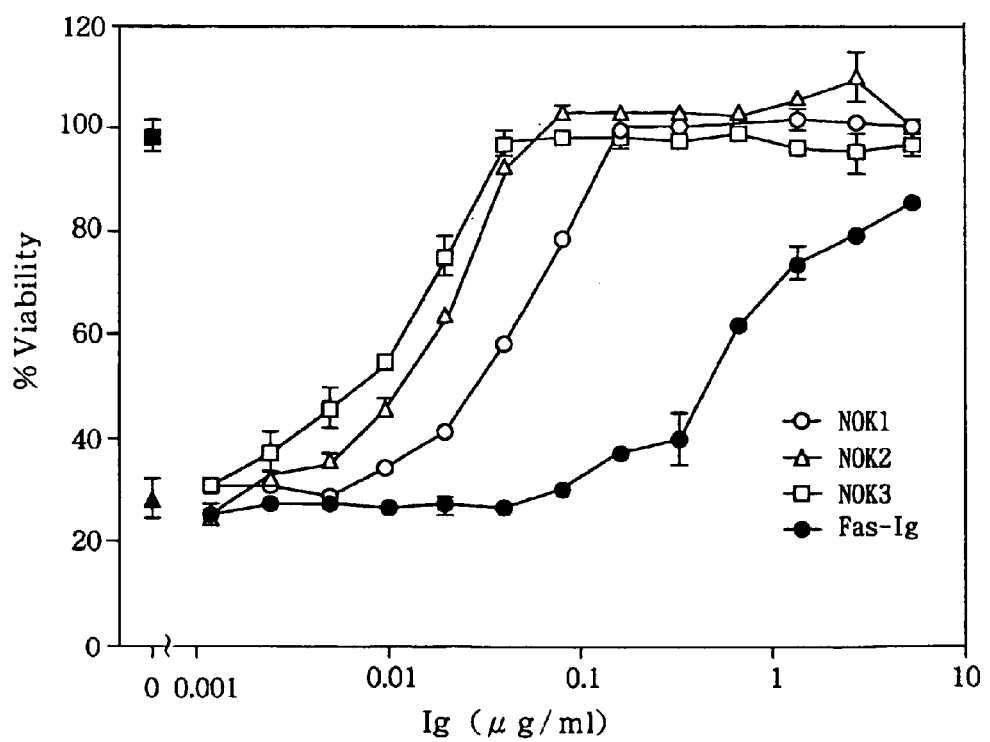
FIG. 4 is a graph illustrating the inhibitory effects of monoclonal antibodies against Fas ligand, and Fas-Ig on the cytotoxicity of a Fas ligand.

As illustrated in FIG. 4, it was demonstrated that all the monoclonal antibodies NOK1 to NOK3 neutralize (inhibit) the apoptosis induction activity of the soluble Fas ligand against the Fas-expressed cells depending on their concentrations. In addition, with respect to their inhibitory effects, it was revealed from FIG. 4 that the monoclonal antibodies according to the present invention exhibit higher inhibitory activities against apoptosis at a concentration (effective concentration) of 0.01–8 μg/ml than the Fas-Ig chimera molecule at the same concentration. Namely, it was demonstrated that the monoclonal antibodies according to the present invention have higher affinity for Fas than Fas-Ig and are more effective.

It is easily considered from this fact that if any one of the monoclonal antibodies NOK1 to NOK3 exists in the living body, a Fas ligand binds to the monoclonal antibody rather than Fas, so that the physiological reaction between Fas and the Fas ligand can be satisfactorily inhibited.

Example 3

Immunoprecipitation of Fas Ligand Molecule

Whether the monoclonal antibody against Fas ligand thus obtained can immunoprecipitate Fas ligand molecules or not was confirmed.

① Fas ligand-L5178Y cells, in which a human Fas ligand had been transfected, were adjusted with 1 ml of a 10% FCS•DME medium containing neither cysteine nor methionine so as to give a concentration of $1 \times 10^6$ cells/ml. $^{35}$S-CyS/Met (Translabel; product of ICN Biomedical Inc.) was added to this cell solution so as to give a concentration of 3.7 MBq/ml to culture the cells at 37° C. for 16 hours in a 24-well plate. Thereafter, a culture supernatant was collected, and a usual 10% FCS•DME medium containing both cysteine and methionine was added to the cells to culture them further for 4 hours.

② After collecting cells, 1 ml of a lytic solution (0.5% Triton X-100, 20 mM Tris-HCl pH 7.6, 150 mM NaCl, 10 μM PMSF, 50 μg/ml trypsin inhibitor) was added to lyse the cells. The lysis was carried out by leaving the mixture to stand for 30 minutes on an ice bath. Thereafter, the mixture was centrifuged for 15 minutes at 15,00 rpm to collect a supernatant of the lytic solution in which the cells had been lysed.

As a control, preclear was first conducted with Sepharose beads, to which mouse IgG had been bound, for the culture supernatant obtained in the step ① and the supernatant of the lytic solution obtained in the step ②. More specifically, 100 μl of the IgG bound beads were added to each of the supernatants to conduct a reaction at 4° C. for 16 hours. The beads were removed by centrifugation, thereby removing substances nonspecifically binding to IgG.

Figure 5:
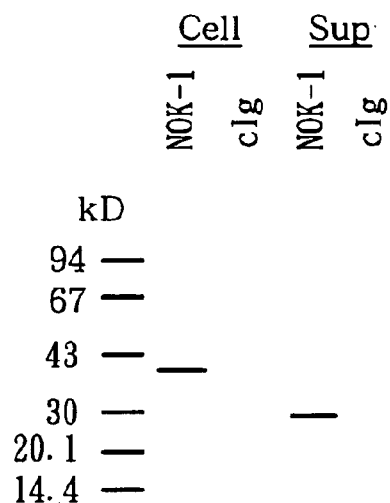
FIG. 5 is a diagram illustrating the results of immunoprecipitation of Fas ligand molecules by a monoclonal antibody NOK1.

Thereafter. 100 μl (amount of beads: 50 μl) of Sepharose beads, to which a purified antibody of NOK1 had been bound, were added to the supernatant to conduct a reaction further for 16 hours at 4° C. A portion not adsorbed on the beads was removed by centrifugation, and the beads were centrifugally washed twice with the lytic solution. Added to the thus-washed beads were 20 μl of a reducing sample buffer for SDS-PAGE to boil them for 5 minutes. Thereafter, 10–20% concentration-gradient gel was used to conduct electrophoresis. After the electrophoresis, the gel was taken out and incubated for 30 minutes by AMPLIFY™ (product of Amersham Japan). Thereafter, the gel was dried and exposed with an X-ray film. As a result, a membrane Fas ligand molecule of about 40 kd and a soluble Pas ligand molecule of about 27 kd were detected from the cell sample (Cell) and the cell culture supernatant (Sup), respectively, as illustrated in FIG. 5. When control mouse IgG-Sepharose beads (clg) were used as a control in place of NOK1-Sepharose beads, detection was infeasible. As a result, it was found that the monoclonal antibody NOK1 can immunoprecipitate the Fas ligand molecules.

Example 4

Quantification of Soluble Fas Ligand

Whether the combination of the antibodies against Fas ligand permits the quantification of a soluble Fas ligand or not was investigated.

① Preparation of Soluble Fas Ligand

Human Fas ligand-L5178Y cells were cultured in a large amount in a serum-free medium EXCELL 300™ (product of JRH Biociences). More specifically, the Fas ligand-L5178Y cells at a concentration of $1 \times 10^6$ cells/ml were cultured in an amount of 30 liters in total using 30 1-liter CULTURE BAGS (manufacture by Sekisui). The culture was conducted for 5 days, and supernatants were then collected by centrifugation at 1,000 g for 15 minutes. Thereafter, the collected supernatant was concentrated to 300 ml by means of a MINITAN™ (manufacture by Milllpore).

The concentrated culture supernatant of the Fas ligand-L5178Y cells was purified through a column made of NOK1-Sepharose beads. The purification was conducted by connecting the column to FPLC to adsorb 300 ml of the concentrated culture supernatant on the beads and then fully washing the column, followed by elution with 0.1 M glycine-hydrochloric acid at pH 3.0. After the eluate was dialyzed against PBS, a portion of the dialyzate was subjected to SDS-PAGE, and the gel was silver-stained to confirm that it was a single band. Thereafter, the amount of protein was determined with a protein assay reagent produced by Bio-Rad. In this culture, 10 μg of a soluble Fas ligand were obtained. This was used as a standard soluble Fas ligand.

② Biotinization of NOK1

The monoclonal antibody NOK1 was labeled with biotin. The labeling was performed in accordance with a method known per se in the art. Namely, the monoclonal antibody NOK1 adjusted to 10 mg/ml with PBS was dialyzed against a 0.1 M carbonate, pH 9.2, buffer to conduct buffer exchange.

To 1 ml of this antibody solution were added 0.2 ml of a solution of 1 mg of NHS-LC-Biotin (product of Pierce Company) in 1 ml of the same carbonate buffer to conduct a reaction for 1 hour at room temperature. The reaction mixture was dialyzed for a day against PBS. The thus-obtained product was used as biotinized monoclonal antibody NOK1.

③ Sandwich ELISA Technique (Quantification of Soluble Fas Ligand)

The quantification of the soluble Fas ligand was performed in accordance with the protocol of the sandwich ELISA technique described below. A soluble Fas ligand molecule was used as a sample to prepare a standard calibration curve.

1) The NOK3 antibody (a purified antibody diluted to 10 μg/ml with PBS) was added to a 96-well ELISA plate (No. MS-8996F manufactured by Sumitomo Bakelite) in a proportion of 50 μl/well. This plate was left to stand for 16 hours at 4° C. to immobilize the monoclonal antibody NOK3 on its bottom. The monoclonal antibody NOK3 may be immobilized on the bottom by leaving the plate over for 4 hours at 37° C.

2) The solution of the NOK3 antibody used in the immobilization was thrown out, and BLOCK ACE (product of Dainippon Pharmaceutical) diluted to ½ with PBS was poured in portions of 200 μl/well into wells to conduct blocking. This treatment was conducted by leaving the plate to stand for 2 hours at 37° C.

3) The blocking solution was thrown out, and the solution of the soluble Fas ligand was poured in portions of 50 μl/well into the wells so as to give concentrations of 7 ng/ml, 3.5 ng/ml, 1.75 ng/ml. 0.875 ng/ml and 0.4325 ng/ml, followed by a reaction at room temperature for 1 hour.

(4) After 1 hour, the plate was washed 5 times with PBS containing 0.05% Tween 20, and the biotinized monoclonal antibody NOK1, which had been diluted to 5 μl/ml with 0.05% Tween 20/PBS containing 5% mouse serum, was poured in portions of 50 μl/well into the wells to conduct a reaction further for 1 hour at room temperature.

(5) The plate was washed 5 times with 0.05% Tween 20/PBS likewise, and an AB COMPLEX solution (product of Vector Company) diluted to ¹⁄₁₅₀ with 0.05% Tween 20/PBS was poured in portions of 50 μl/well into the wells to conduct a reaction further for 1 hour at room temperature.

(6) After the plate was washed 5 times with 0.05% Tween 20/PBS, a 0.1 M citric acid-sodium phosphate (pH 5.0) buffer containing 1 mg/ml of o-phenylenediamine (product of Wako Pure Chemical Industries, Ltd.) and 0.03% aqueous hydrogen peroxide was poured in portions of 100 μl/well into the wells to conduct a reaction for about 20 minutes at room temperature.

7) Thereafter, 2N sulfuric acid were placed in a proportion of 100 μl/well in the wells to stop the reaction, thereby measuring absorbance values at 490 nm by a microplate reader (manufactured by Bio-Rad).

As a result, the soluble Fas ligand was able to be quantified. A standard curve at this time is illustrated in FIG. 6.

Figure 6:
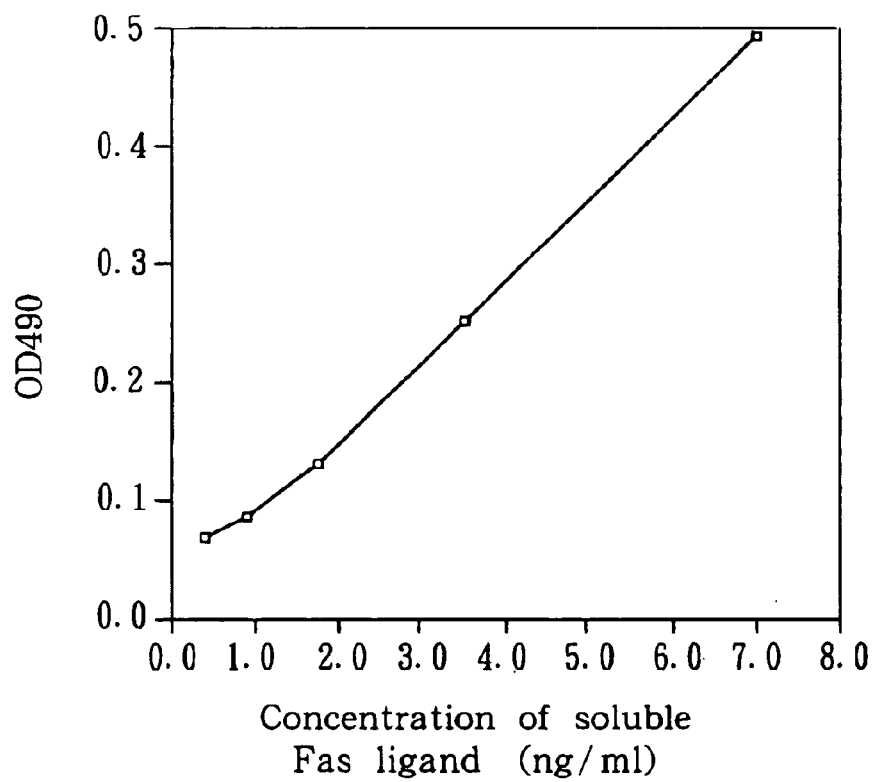
FIG. 6 is a graph (standard curve) illustrating the quantification result of a soluble Fas ligand by a sandwich ELISA technique using two kinds of monoclonal antibodies against Fas ligand in combination.

As illustrated in FIG. 6, it was clarified for the first time that this method permits the detection of the soluble Fas ligand at a concentration ranging from 7 ng/ml to 0.4325 ng/ml.

Example 5

Quantification of Fas Ligand in Serum

Figure 7:
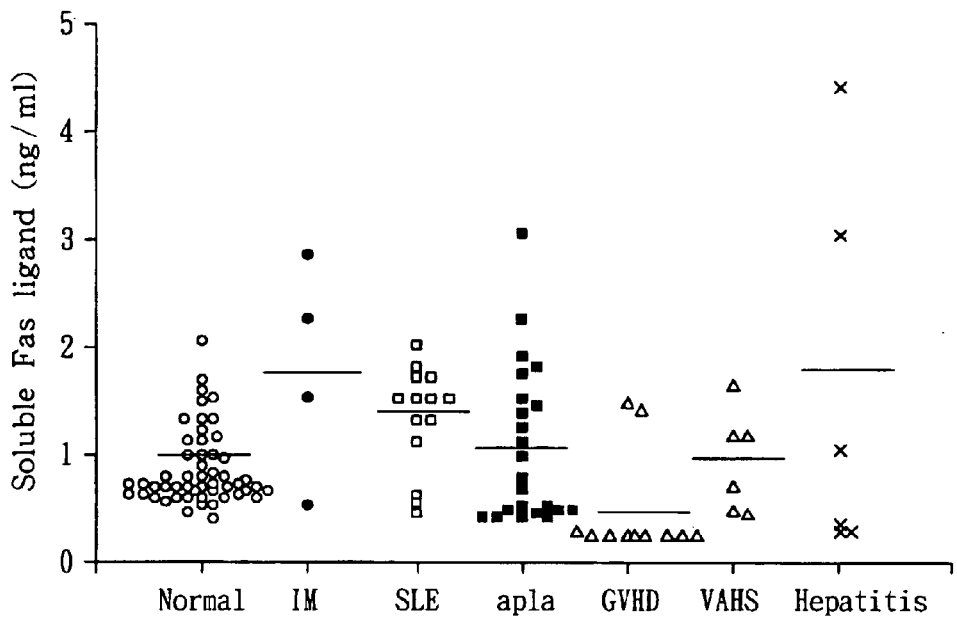
FIG. 7 is a graph illustrating the measurement results of a soluble Fas ligand contained in sera of various diseases.

Sera of patients suffered from diseases described below were actually used to quantify a Fas ligand in the sera in accordance with the protocol of the sandwich ELISA described in Example 4. The method was as follows. Following the step ③ of 3) in Example 4, measurements were conducted by using the standard of the soluble Fas ligand, and sera from patients of IM (infectious mononucleosis), SLE (systemic lupus erythematodes), apla (aplastic anemia), GVHD (graft-versus-host disease), VAHS (virus-associated hemophagocytic syndrome) and hepatitis and a normal person, thereby quantifying a Fas ligand in the respective sera in comparison with the standard of the soluble Fas ligand. The results are illustrated in FIG. 7. According to this method, it was revealed from FIG. 7 that the concentrations of the Fas ligand in the sera from the patients of IM. SLE and hepatitis are higher than that of the normal person, and so it was clarified for the first time that the diagnoses of these diseases can be conducted by this method.

Example 6

Investigation as to Reactivity to Monkey Fas Ligand

Five milliliters of peripheral blood were collected from a rhesus monkey using a heparinized syringe. After the blood was diluted to ½ with PBS, its lymphocyte fraction was recovered by the specific gravity centrifugation using Separate L. These monkey peripheral blood mononuclear lymphocytes were cultured for 2 days in a 10% FCS•RPMI 1640 medium containing 10 μg/ml of Con A to activate them. Thereafter, the cells were recovered by centrifugation, and then cultured further for a week in a 10% FCS•RPMI 1640 medium containing 50 units/ml of human IL-2 (interleukin-2). After a week, PMA and ionomycin were added to give concentrations of 10 ng/ml and 500 ng/ml, respectively, to activate the cells further for 4 hours. At this time, BB94 (matrix protease inhibitor) was added in a proportion of 10 μM at the same time. The Fas ligand was expressed in a large amount on the lymphocytes by these activation processes. After 4 hours, the cell were collected to analyze them by flow cytometry. After collecting the cells, the number of cells was first counted to adjust the cells to $1 \times 10^6$ cells/ml with PBS. Thereafter, the cells were placed in portions of 1 ml into tubes (Farcon No-2008), and 100 μl of control PBS, 1 μg of NOK1 antibody (100 μl of one diluted to a concentration of 10 μg/ml with PBS), 1 μg of monoclonal antibody NOK2 (similarly, 100 μl at a concentration of 10 μg/ml) and 1 μg of monoclonal antibody NOK3 (similarly, 100 μl at a concentration of 10 µl/ml) were separately placed in the tubes, thereby conducting a reaction for 30 minutes on an ice bath.

After the respective cultures were centrifugally washed twice with PBS. 1 µl of PE-anti-mouse Ig's were placed in the tubes to conduct a reaction further for 30 minutes on the ice bath. After the cultures were washed with PBS and separately suspended in 200 µl of PBS, they were analyzed by FACScan.

Figure 8:
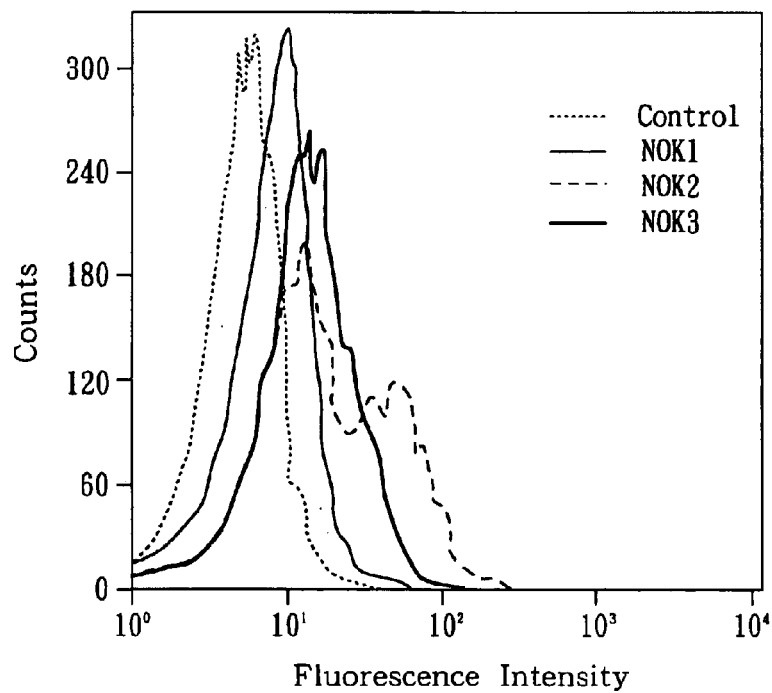
FIG. 8 is an FACScan chart illustrating the analytical results of reactivity of monoclonal antibodies to a Fas ligand present on activated monkey peripheral blood mononuclear cell surfaces.

As a result, as illustrated in FIG. 8, peaks of fluorescence intensity as to all the monoclonal antibodies NOK1 to NOK3 appeared at different places from the control. Namely, it was clarified that the respective antibodies react with the Fas ligand on monkey cell surfaces.

Example 7

Inhibitory Effect on the Action of Mouse Fas Ligand

Mouse Fas ligand gene-transfected cells, mFasL/L5178Y, were used in place of the human Fas ligand gene-transfected cells, hFasL/L5178Y, to carry out an investigation. The investigation was conducted by using a cytotoxic reaction test making use of $^{51}$Cr. The protocol thereof will hereinafter be described.

① Preparation of Effector Cells hFasL/L5178Y and mFasL/L5178Y (prepared in the same process as in the hFasL/L5178Y) were separately collected from culturing flasks to adjust them $1 \times 10^6$ cells/ml with a 10% FCS•RPMI 1640 medium.

② Preparation of Target Cells

With respect to hFas/WR in which a human Fas gene had been transfected, and WR which is a parent strain thereof, 100 µl of cultures containing $5 \times 10^6$ cells/ml were separately prepared in a 10% FCS•RPMI 1640 medium. Na$_2$$^{51}$CrO$_4$ (product of ICN) was then added in an amount of 3.7 MBq (100 µl at 37 MBq/ml) to the cultures to incubate them at 37° C. for 1 hour. Thereafter, the cultures were centrifugally washed 3 times with a 10% FCS-RPMI 1640 medium and then diluted to $1 \times 10^5$ cells/ml with the same medium.

③ Cytotoxic Reaction

The effector cell samples were separately placed in 96-well•Multiplate U Bottoms (product of Corning) in a proportion of 100 µl/well. Culture supernatants of the hybridomas NOK1 to NOK3 were used as respective monoclonal antibodies against Fas ligand, and these were poured in a proportion of 40 µl/well into wells. Those containing no antibody were used as a control. In order to conduct controls of 100% survival and 100% death, the medium was placed in a proportion of 100 µl/well into 6 wells without putting any effector cells therein. The target cells were then added to the respective wells in a proportion of 100 µl/well. Further, 20 µl of 10% SDS were added to the wells intended for 100% death.

Figure 9:
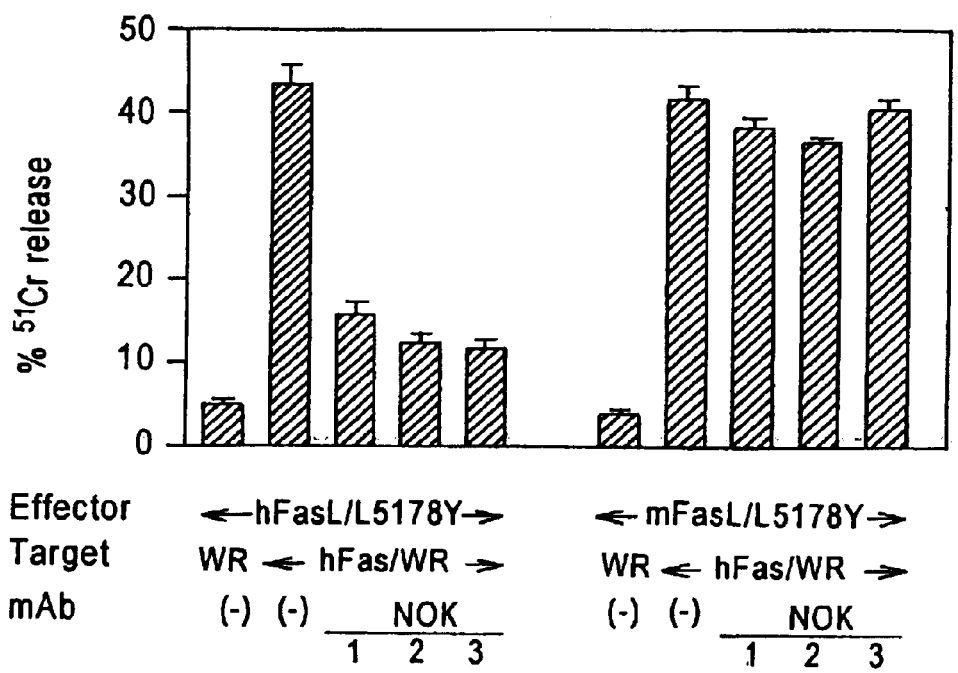
FIG. 9 is a graph illustrating the inhibitory effects of monoclonal antibodies against Fas ligand on a cytotoxic reaction mediated by a Fas ligand and Fas.

Thereafter, a reaction was conducted in each well for 6 hours (incubated under conditions of 37° C. and 5% CO$_2$), and the plate was centrifuged to precipitate cells on the bottoms of each well. Supernatants were collected by each 100 µl from the wells to count $^{51}$Cr isolated in the supernatant by a γ-ray scintillation counter (manufactured by Pharmacia). The measurement results thereof are shown in FIG. 9. Incidentally, the average of the wells added with 10% SDS and the average of the wells containing only the target cells were regarded as 100% death and 100% survival, respectively, to determine killer activities (cytotoxicities) of the respective Fas ligands. As a result, it was found that the antibodies against human Fas ligand typified by the monoclonal antibodies NOK1 to NOK3 inhibit the action of the human Fas ligand, but do not inhibit the action of the mouse Fas ligand.

Example 8

Sequencing (1) of V Region Genes of Anti-FasL Antibody

Using the hybridomas NOK1 to NOK5, variable region (V region) genes of monoclonal antibodies against Fas ligand were sequenced.

1. Preparation of cDNA (1) The hybridomas NOK1 to NOK5 were separately cultured in 25-cm2 flasks. After cultured cells were collected and centrifugally washed with PBS, the cells were suspended in 1 ml of PBS to count the number of cells. The cells were placed in an amount of $1 \times 10^6$ cells in a sterile Eppendorf tube. A supernatant was drawn out by centrifugation to tap the resultant pellet.

(2) Added to the tube were 200 µl of RNA$_{zol}$B (product of Cosmo-Bio) to fully stir the mixture with a tip of a pipetteman, thereby dissolving the cells therein. After 20 µl of chloroform were added, and the tube was shaken, it was left to stand for 5 minutes on an ice bath. After the tube was centrifuged for 15 minutes at 4° C. and 15,000 rpm, the resultant colorless, transparent portion of an upper layer was recovered and transferred to a new tube. After the upper portion was centrifuged for 15 minutes at 4° C. and 15,000 rpm, a supernatant was thrown out, 800 µl of 75% ethanol were added to the residual pellet, and the mixture was left to stand for 30 minutes at −20° C. After the mixture was centrifuged for 15 minutes at 4° C. and 15,000 rpm, 11.5 µl of distilled water were added to the pellet.

(3) Oligo dT (0.5 mg/ml) in an amount of 0.5 µl was added, and the mixture was left to stand for 10 minutes at 70° C. and for 5 minutes on an ice bath.

TABLE 3

| | |
|---|---|
| 5 × RT buffer | 4 µl |
| 10 mM dNTPmix | 1 µl |
| SUPERSCRIPT RTase (product of Stratagene) | 1 µl |

(product of Stratagene).

The above components were added, and the mixture was left to stand for 5 minutes at 90° C. and then for 5 minutes on an ice bath.

(4) Added to the mixture was 1 µl of RNaseH, and the resultant mixture was left to stand for 20 minutes at 37° C. In the above-described manner, a mixture of cDNAs was obtained.

2. PCR (1) The cDNAs obtained by the above-described process were used to conduct PCR in the following conditions.

TABLE 4

| | VH | VL |
|---|---|---|
| cDNA | 2 µl | 2 µl |
| dNTPmix | 1 µl | 1 µl |
| Primer (product of Pharmacia) | 2 µl | 1 µl |
| 10 × PCR buffer | 4 µl | 4 µl |
| DDW | 30.5 µl | 31.5 µl |
| AMPLITAQ | 0.5 µl | 0.5 µl |

After the mixture was topped with 40 µl of mineral oil and left over for 5 minutes at 94° C., an amplification reaction was carried out by repeating the cycle of "2 minutes at 55° C. 3 minutes at 72° C. and 1 minute at 94° C." 30 cycles. The reaction mixture was then left to stand for 2 minutes at 55° C. and for 10 minutes at 72° C.

Figure 10:
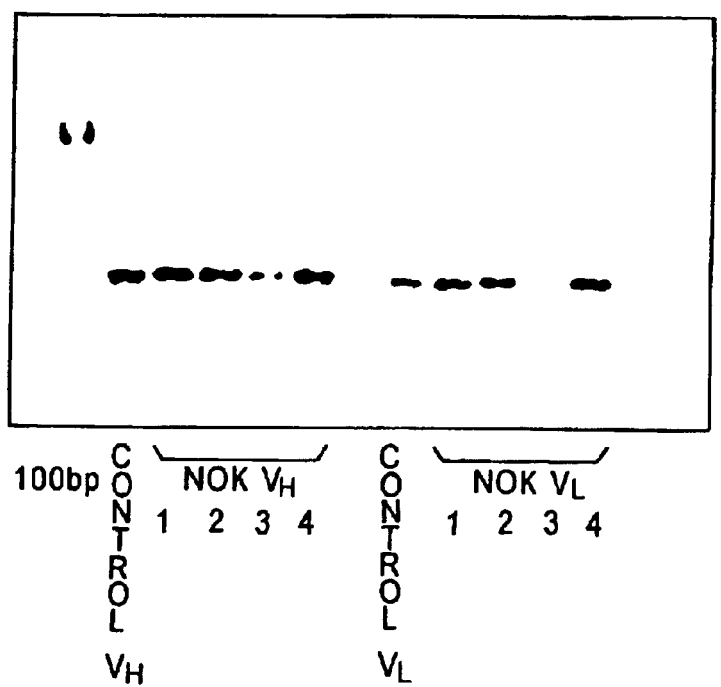
FIG. 10 is a mini gel electrophorogram of reaction mixtures in PCR of VH genes and VL genes of anti-FasL antibodies.

(2) The reaction mixture in an amount of 4 µl was checked by mini gel electrophoresis (1.5% agarose gel). The result is illustrated in FIG. 10. It was confirmed that DNA fragments except for the L chain of the monoclonal antibody NOK3 were amplified by PCR.

3. Recovery of VH and VL Fragments (1) The PCR products prepared above were subjected to mini gel electrophoresis (1.5% agarose gel) to get bands of VH (variable region of H chain) and VL (variable region of L chain) out of the gel.

Figure 11:
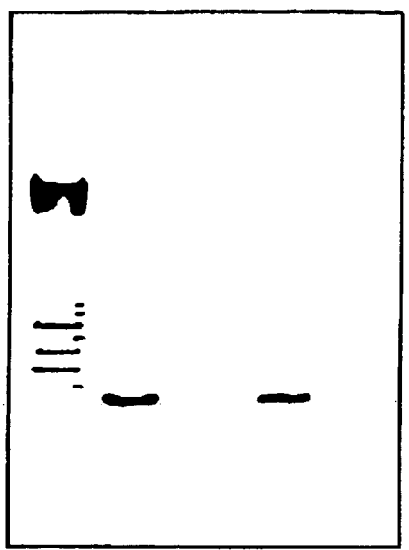
FIG. 11 is a mini gel electrophorogram of a product in PCR of a VL gene of NOK4.

(2) The PCR products were recovered by GENECLEAN to check the bands by mini gel electrophoresis (1.5% agarose gel). As an example, the result as to the VH of NOK4 is illustrated in FIG. 11.

4. Ligation

The following TA cloning kit was used to conduct ligation of DNA.

TABLE 5

| | |
|---|---|
| ADDW | 5 µl |
| 10 × Ligation buffer | 1 µl |
| PCR vector | 2 µl |
| PCR product | 1 µl |
| T4DNA Ligase | 1 µl |

The reaction was conducted overnight at 14° C. to obtain a ligation mixture.

5. Transformation

The TA cloning kit was used to conduct transformation.

(1) After 2 µl of 0.5 M β-mercaptoethanol and the ligation mixture prepared above were added to 50 µl of the cells on an ice bath, and the mixture was left over for 30 minutes and then left to stand for 30 seconds on a hot water bath of 42° C. and then for 20 minutes on an ice bath. The mixture was added with 450 µl of an SOC medium and incubated at 37° C. for 1 hour (225 rpm).

(2) The cells were then spread on LB agar plates (+Amp, X-Gal, IPTG). The respective samples were of 50 µl, 100 µl and 200 µl. After incubation was conducted at 37° C. for 18 hours, the medium was left to stand for 2 minutes at 4° C. As a result, white and blue colonies were expressed.

6. Mini Culture (1) Four white colonies were taken out of each sample plate.

(2) One colony was added to 3 ml of an LB medium (+Amp), and the medium was shaken overnight at 37° C.

7. Mini Preparation (1) A culture solution in an amount of 1.5 ml was taken in an Eppendorf tube. (It was spread on an LB plate for conservation and cultured at 37° C.) The culture was centrifuged for 2 minutes at 4° C. and 6,000 rpm.

(2) After the precipitate was added with 100 µl of Solution 1 (5 mg/ml of lysozyme) and left to stand for 5 minutes at room temperature, the resultant mixture was added with 200 µl of Solution 2 (mixed gently for 5 minutes on an ice bath) and with 150 µl of Solution 3 (mixed for 15 minutes on an ice bath), and then centrifuged for 5 minutes at 4° C. and 12,000 rpm.

(3) A supernatant was taken in a new Eppendorf tube. An equal volume of phenol was added thereto, and the tube was then centrifuged for 1 minute at 12,000 rpm.

(4) A supernatant was taken in a new Eppendorf tube. An equal volume of a mixture of CHCl$_3$:iAA (99:1) was added thereto, and the tube was then centrifuged for 1 minute at 12,000 rpm.

(5) A supernatant was taken in a new Eppendorf tube. The supernatant was added with 1 µl of Mussel glycogen and 900 µl of ethanol, left to stand for 30 minutes at −80° C. and then centrifuged for 5 minutes at 4° C. and 15,000 rpm.

(6) Precipitate was dried, added with 20 µl of TE and 1 µl of RNaseA (5 mg/ml) and then left to stand for 20 minutes at 65° C.

(7) In the above-described manner, plasmid DNAs were obtained.

Figure 12:
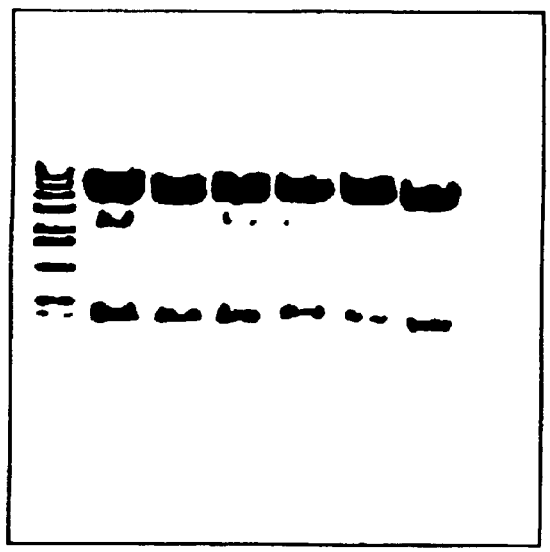
FIG. 12 is a mini gel electrophorogram of plasmid DNAs.

(8) Mini gel electrophoresis was performed under the following conditions to check bands. The results as to NOK4 $V_L$, NOK5 $V_L$ and NOK5 $V_L$ are illustrated in FIG. 12.

TABLE 6

| | |
|---|---|
| H Buf. | 1 µl |
| Eco RI | 1 µl (1U) |
| DNA | 1 µl |
| ADDW | 7 µl |

The sample was incubated at 37° C. for 1 hour and then added with 0.75% agarose gel to conduct electrophoresis.

8. DNA Sequencing (1) Each plasmid DNA in an amount of 1 µl was taken out and diluted with 99 µl of TE.

(2) The A260 value thereof was determined to calculate its DNA value (A260 of 1.0=50 µg/ml).

(3) Based on the A260 value, the plasmid DNA was diluted with TE in such a manner that the concentration of DNA reaches 1 µg/µl.

(4) DNA sequencing performed by the Dye-terminator method (using Autosequencer; ABI Model 373A).

9. Analysis of V Regions

Based on the DNA sequences thus obtained, the amino acid sequences of the V regions were determined by computer analysis. The results are illustrated in FIG. 13 (amino acid sequences of the VH regions of the monoclonal antibodies NOK1 to NOK5) and FIG. 14 (amino acid sequences of the VL regions of the monoclonal antibodies NOK1 to NOK5). In these drawings, portions enclosed with a rectangle represent hypervariable regions (CD1 to CD3).

Example 9

Sequencing (2) of V Region Genes of Anti-FasL Antibody

With respect to the hybridomas NOK1 to NOK3, V region genes were sequenced by using other primers for PCR than those used in Example 8.

1. Preparation of cDNA (1) The hybridomas NOK1 to NOK3 were separately cultured in 25-cm³ flasks. After cultured cells were collected and centrifugally washed with PBS, the cells were suspended in 1 ml of PBS to count the number of cells. The cells were placed in an amount of 1×10⁶ cells in a sterile Eppendorf tube. A supernatant was drawn out by centrifugation to tap the resultant pellet.

(2) Total RNA was prepared from this cell pellet using an ISOGEN kit (product of Nippon Gene) and then purified into mRNA using a POLY(A)QUICK Kit (product of Stratagene).

(3) cDNAs were then synthesized by the oligo dT method. This process was conducted by using a FIRST STRAND cDNA Synthesis kit (product of Pharmacia) to synthesize the cDNAs.

2. PCR

The cDNAs obtained by the above-described process were used to conduct PCR in the following conditions. With respect to both VH and VL, the reaction was performed under the same conditions except for primers. In the PCR of VH, primers suitable for use in amplifying VH were used, while primers suitable for use in amplifying VL were used in the PCR of VL.

TABLE 7

| | |
|---|---|
| cDNA | 5 μl |
| dNTPmix (25 mM each) | 1 μl |
| Primer mixture (50 pmol/μl) | |
| Anti-sense primer | 1 μl |
| Sense primer | 1 μl |
| 10 × PCR buffer | 10 μl |
| Takara EX Taq (5 u/μl) | 0.5 μl |
| DW | 81.5 μl |
| total | 100 μl |

After the mixture was topped with 100 μl of mineral oil and left over for 1 minute at 95° C., an amplification reaction was carried out by repeating the cycle of "2 minutes at 60° C., 2 minutes at 72° C. and 1 minute at 94° C." 35 cycles.

Incidentally, the primers were prepared by a DNA synthesizer with reference to the following materials.

A new sense primer was designed in a leader region situated upstream from a variable region based on E. A. Kabat et al., Classification of Variable Region Genes of Antibodies (Sequences of Proteins of Immunological Interest 4th ed., Public Health Service, NHI, Washington D.C., 1987). An anti-sense primer was designed in a constant region by reference to "Gene Sequences of Constant Regions of Mouse Antibodies" described in a book of D. M. Weir et al. (HANDBOOK OF EXPERIMENTAL IMMUNOLOGY VOLUME 3: GENETICS AND MOLECULAR IMMUNOLOGY).

3. Recovery of VH and VL Fragments (1) The PCR products prepared above were subjected to mini gel electrophoresis (1.5% agarose gel) to get bands of VH (variable region of H chain) and VL (variable region of L chain) out of the gel.

(2) The PCR products were recovered by GENECLEAN to check the bands by mini gel electrophoresis (1.5% agarose gel).

4. Ligation

The following TA cloning kit was used to conduct ligation of DNA.

TABLE 8

| | |
|---|---|
| ADDW | 5 μl |
| 10 × Ligation buffer | 1 μl |
| PCR vector | 2 μl |
| PCR product | 1 μl |
| T4DNA Ligase | 1 μl |

The reaction was conducted overnight at 14° C. to obtain a ligation mixture.

5. Transformation

The TA cloning kit was used to conduct transformation.

(1) After 2 μl of 0.5 M β-mercaptoethanol and the ligation mixture prepared above were added to 50 μl of cells on an ice bath, and the mixture was left over for 30 minutes and then left to stand for 30 seconds on a hot water bath of 42° C. and then for 20 minutes on an ice bath. The mixture was added with 450 μl of an SOC medium and incubated at 37° C. for 1 hour (225 rpm).

(2) The cells were then spread on LB agar plates (+Amp, X-Gal, IPTG). The respective samples were of 50 μl, 100 μl and 200 μl. After incubation was conducted at 37° C. for 18 hours, the medium was left to stand for 2 minutes at 4° C. As a result, white and blue colonies were expressed.

6. Mini Culture (1) Four white colonies were taken out of each sample plate.

(2) One colony was added to 3 ml of an LB medium (+Amp), and the medium was shaken overnight at 37° C.

7. Mini Preparation (1) A culture solution in an amount of 1.5 ml was taken in an Eppendorf tube. (It was spread on an LB plate for conservation and cultured at 37° C.) The culture was centrifuged for 2 minutes at 4° C. and 6,000 rpm.

(2) After the precipitate was added with 100 μl of Solution 1 (5 mg/ml of lysozyme) and left to stand for 5 minutes at room temperature, the resultant mixture was added with 200 μl of Solution 2 (mixed gently for 5 minutes on an ice bath) and with 150 μl of Solution 3 (mixed for 15 minutes on an ice bath), and then centrifuged for 5 minutes at 4° C. and 12,000 rpm.

(3) A supernatant was taken in a new Eppendorf tube. An equal volume of phenol was added thereto, and the tube was then centrifuged for 1 minute at 12,000 rpm.

(4) A supernatant was taken in a new Eppendorf tube. An equal volume of a mixture of $CHCl_3$:iAA (99:1) was added thereto, and the tube was then centrifuged for 1 minute at 12,000 rpm.

(5) A supernatant was taken in a new Eppendorf tube. The supernatant was added with 1 μl of Mussel glycogen and 900 μl of ethanol, left to stand for 30 minutes at −80° C. and then centrifuged for 5 minutes at 4° C. and 15,000 rpm.

(6) Precipitate was dried, added with 20 μl of TE and 1 μl of RNaseA (5 mg/ml) and then left to stand for 20 minutes at 65° C.

(7) In the above-described manner, plasmid DNAs were obtained.

8. DNA Sequencing (1) Each plasmid DNA in an amount of 1 μl was taken out and diluted with 99 μl of TE.

(2) The A260 value thereof was determined to calculate its DNA value (A260 of 1.0=50 μg/ml).

(3) Based on the A260 value, the plasmid DNA was diluted with TE in such a manner that the concentration of DNA reaches 1 μg/μl.

(4) DNA sequencing was performed by the Dye-terminator method (using ABI Model 373A).

9. Analysis of V Regions

Based on the DNA sequences thus obtained, the amino acid sequences of the V regions were determined by computer analysis. The results are illustrated in FIG. 15 (amino acid sequences of the VH regions of the monoclonal antibodies NOK1 to NOK3) and FIG. 16 (amino acid sequences of the VL regions of the monoclonal antibodies NOK1 to NOK3). In these drawings, portions enclosed with a rectangle represent hypervariable regions (CD1 to CD3).

Example 10

Preparation and Characterization of Monoclonal Antibodies (1) Isolation of Fas Ligand Gene ① Preparation of Primers A mouse Fas ligand gene was isolated on the basis of the report by Nagata et al. More specifically, Xho I-5' FasL obtained by adding a sequence of 18mers of the 5' end of a mouse Fas ligand to a sequence of the Xho-I site on the 5' end side of mouse Fas ligand cDNA, and Not1-3' FasL obtained by adding a sequence of 18mers of the 3' end of a mouse Fas ligand to a sequence of the Not1 site on the 3' end side of mouse Fas ligand cDNA were separately subjected to DNA synthesis using Model 392 DNA/RNA synthesizer (manufactured by ABI) on a scale of 0.2 μmol. The product DNAs were purified in accordance with the protocol to prepare primers for PCR.

② Preparation of Template of Fas Ligand cDNA

A template was prepared from B6 mouse-derived cells in which a mouse Fas ligand had been expressed. More specifically, splenocytes of a B6 mouse were activated with an anti-CD3 antibody-immobilized plate to collect $1 \times 10^7$ cells. The collected cells were suspended in 1 ml of RNA-zolB (product of Cosmo Bio). After 100 μl of chloroform were further added to the suspension, the mixture was left to stand for 30 minutes on an ice bath. Thereafter, a phenol layer was separated from a water layer by centrifugation (at 4° C.) for 15 minutes at 15,000 rpm to recover only the upper water layer. An equiamount of isopropanol was added to the water layer, and the resultant mixture was left to stand for 30 minutes at −80° C., followed by precipitation of RNA by centrifugation (15,000 rpm, 15 minutes, 4° C.). After the precipitate thus obtained was centrifugally washed once with 1 ml of ethanol, it was suspended in 11.5 μl of water subjected to DEPC treatment. Added to this RNA suspension were 0.5 μl (0.5 mg/ml) of synthetic oligo dT, followed by a heat treatment for 10 minutes at 70° C. The mixture thus treated was then treated on an ice bath for 5 minutes.

Thereafter, 4 μl of 5×RT buffer (product of Stratagene), 1 μm of 10 mM dNTP, 2 μl of 0.1 M DTT and 1 μl of SUPERSCRIPT RTase (product of Stratagene) were added to to conduct a reaction at 42° C. for 50 minutes, thereby reversely transcribing RNA into cDNA. After the reaction mixture was treated at 90° C. for 5 minutes to deactivate the RTase, it was left to stand for 5 minutes on an ice bath. After 1 μl of RNaseH (product of Stratagene) was then added to this sample to conduct a reaction further for 20 minutes at 37° C., thereby decomposing unnecessary RNA to provide a template for cDNA containing a Fas ligand.

③ PCR

PCR was performed by reference to PCR Experimental Manual (HBJ Press, pp. 75–85) under the following conditions.

Namely, 1 μl of 10 mM dNTPmix (product of Pharmacia), 1 μl of Xho I Site-5' mouse FasL 18mer (50 μM), 1 μl of Not I-3' mouse FasL 18mer (50 μM), 4 μl of 10×PCR buffer (product of Perkin-Elmer), 0.5 μl of AMPLITAQ™ (product of Perkin-Elmer) and 30.5 μl of water were added to 2 μl of the cDNA produced in Step ② into a solution of 40 μl in total. After this solution was topped with 40 μl of mineral oil (product of Sigma), an amplification reaction was carried out by means of a DNA thermal cycler for PCR (manufactured by Perkin-Elmer Japan). More specifically, the amplification reaction was carried out under conditions of successively 5 minutes at 94° C., 2 minutes at 55° C., 3 minutes at 72° C., 1 minute at 94° C., 2 minutes at 55° C. and 10 minutes at 72° C. by repeating the treatment between 2 minutes at 55° C. and 1 minute at 94° C. 30 cycles.

④ Integration into BCMGSneo Vector

After conducting the amplification reaction by PCR, only a water layer was extracted with a mixture of phenol and chloroform. Each 1.0 unit of Xho I and Not I (both, products of Boehringer Co.) were added to the extract thus obtained, and an accessory buffer was added, followed by a reaction at 37° C. for 16 hours. The reaction mixture was electrophoresed in a 1% agarose gel. A band of about 850 bp corresponding to the Fas ligand was got out of the gel under UV irradiation.

DNA was extracted from this agarose gel using a GENECLEAN II kit (product of BIO101, Funakoshi). More specifically, an accessory NaI solution was added to the gel to incubate the gel at 65° C. for 10 minuets, thereby dissolving the gel in the solution. Glass milk was then added to the solution, and the mixture was rotationally stirred for 5 minutes to adsorb DNA on the glass milk. After this glass milk was washed three times with New-WASH solution, it was suspended in 10 μl of a TE buffer. The suspension was incubated at 65° C. for 3 minutes, thereby dissolving DNA out of the glass milk.

A BCMGSneo vector in an amount of 1 μl was then treated with the restriction enzymes Xho I and Not I in the same manner as described above to electrophorese it in a 0.75% agarose gel, followed by purification with the GENECLEAN II kit.

The Fas ligand cDNA and BCMGSneo vector were then ligated. More specifically, they were mixed so as to give a molar ratio of the vector to cDNA of 1:2, and the mixture was subjected to a ligation reaction at 16° C. for 16 hours using a DNA ligation kit produced by Takara Shuzo Co., Ltd.

⑤ Integration into *Escherichia coli*

The reaction mixture obtained in the step ④ was mixed with *Escherichia coli* competent cells (product of Toyobo) to incubate the mixture for 30 minutes on an ice bath and for 40 seconds at 42° C., thereby inserting DNA into *Escherichia coli*. After an SOC medium was added thereto to conduct shaking culture at 37° C. for 1 hour, the culture was poured into an LB agar medium containing ampicillin to conduct culture at 37° C. for 1 day. Thereafter, appeared colonies were cultured at 37° C. for 1 day in the LB medium, and the resultant plasmid (mouse Fas ligand-BCMGSneo) was then recovered by the alkali method.

(2) Transfection into L5178Y Cell

The transfection of this mouse Fas ligand-BCMGSneo into L5178Y cells was carried out in a proportion of (the mouse Fas ligand-BCMGSneo 1 μg)/($1 \times 10^6$ L5178Y cells) in accordance with the electroporation method under conditions that a GENE PULSER (manufacture by Bio-Rad) was used at 296 V and 960 μF. The cells were suspended again in 5 ml of a 10% FCS•RPMI 1640 medium. The suspension of the cells was poured into a 6-well plate to conduct culture. At this time, G418 (product of GIBCO) was added so as to give a concentration of 0.4 mg/ml. After 10 days from the culture, colonies were obtained, so that cells were cloned by the limiting dilution technique. A clone having the highest mouse Fas ligand mRNA content was sorted from the thus-obtained clones by the northern hybridization technique and cultured. The cells thus obtained were regarded as the mouse Fas ligand-L5178Y cells.

(3) Immunosensitization

A suspension of the Fas ligand-expressed COS cells prepared in the step (2) was intraperitoneally injected into an MRL gld mouse (female, aged 4 weeks) in a proportion of $1 \times 10^7$ cells/mouse. After a week, the suspension of the Fas ligand-expressed COS cells was injected in the same mouse once a week, 3 times in total, thereby immunosensitizing the mouse.

(4) Cell Fusion

After 3 days from the final immunization, the spleen was taken out of the mouse. The spleen was minced, filtered through a mesh and then suspended in an RPMI 1640 medium (product of Nissui), thereby obtaining $1 \times 10^8$ splenocytes. The splenocytes and a mouse-derived 8-azaguanine-resistant strain (hypoxanthine-guanine phosphoribosyl transferase defective strain) P3X63Ag8.653

(ATCC CRL 1580) ($1\times10^7$ cells) were mixed with each other in a proportion of about 5:1, and the resulting mixture was centrifuged (1500 rpm, 5 minutes).

To the cell pellet thus obtained, 2 ml of a 50% solution of polyethylene glycol 4000 (product of Merck) in an RPMI 1640 medium was added over 1 minute with stirring in a hot water bath of 37° C. Added to the resulting mixture were 15 ml of an RPMI 1640 medium over 6 minutes with stirring, thereby conducting cell fusion. After the cell fusion, a great amount (about 40 ml) of an RPMI 1640 medium was added, and the mixture was centrifuged (1500 rpm, 5 minutes) to remove a supernatant. The splenocytes were then adjusted to $1\times10^6$ cells/ml with a 10% FCS (fetal calf serum)-RPMI 1640 medium (HAT medium) containing hypoxanthine (100 $\mu$M), aminopterine (0.4 $\mu$M) and thymidine (10 $\mu$M).

5) Selection of Hybridoma

The cell suspension prepared in the step (4) was poured in 200-$\mu$l portions into 10 microplates each having 96 wells to culture the cells in a $CO_2$-incubator controlled at 37° C. and $CO_2$ concentration of 5%. After a week, it was confirmed that only hybridomas formed colonies and proliferated.

(6) Sorting of Hybridomas

A transfectant mFasL/L5178Y in which a mouse Fas ligand had been transfected was used as an effector molecule, and a transfectant which expresses a Fas antigen on a cell surface was used as a target to sort out hybridomas in the culture supernatants which blocked the killer activity of the mouse Fas ligand-expressed transfectant against the Fas-expressed transfectant.

① Preparation of Effector Cells

Fas ligand gene-transfected cells (transfectant) were used as effector cells. Namely, the above-described transfectant obtained by transfecting mouse Fas ligand-BCMGSneo into L5178Y cells using the electroporation method was used. The cells were adjusted to $1\times10^6$ cells/ml with a 10% FCS•RPMI 1640 medium to provide them in an amount of 50 ml.

② Preparation of Target Cells

WR19L cells in which a human Fas gene had been transfected were used as the target cells. The transfection of the human Fas gene into WR19L (ATCC TIB52) was performed in accordance with a method known per se in the art. More specifically, the cells were prepared by reference to literature by Hanabuchi et al. (Proc. Natl. Acad. Sci. USA, Vol. 91, No. 11, pp. 4930–4934, 1994). The Fas-WR19L cells thus obtained were cultured and collected by $1\times10^7$ cells in a 10% FCS•RPMI medium. The cells were cultured overnight at 37° C. in 10 ml of a 10% FCS•RPMI medium containing 1 mCi of $^3$H-thymidine, thereby incorporating $^3$H-thymidine into the cells.

After collecting the cells by centrifugation, they were centrifugally washed 3 times with a 10% FCS•RPMI medium and adjusted to $2\times10^5$ cells/ml with a 10% FCS•RPMI medium. This cell suspension was used as the target cells.

③ Screening Assay

The effector cells prepared in the step ① was first poured in portions of 50 $\mu$l/well into 10 96-well U type plates (manufacture by Corning), and 100 $\mu$l of the culture supernatant of each hybridoma were added, followed by incubation at 37° C. for 1 hour. Thereafter, the Fas/WR19L target cells prepared in the step ② were added in a proportion of 50 $\mu$l/well and incubated for 6 hours under conditions of 37° C. and 5% $CO_2$.

Thereafter, the plates were centrifuged to count $^3$H in the resultant supernatants by means of a liquid scintillation counter. Incidentally, as a control for 100% survival, a supernatant obtained by adding 50 $\mu$l of a medium in place of 50 $\mu$l of the effector cells was used, while as a control for 100% death, a supernatant obtained by adding 100 $\mu$l of a 2% Triton ×100 solution in place of 100 $\mu$l of the culture supernatant was used. Based on the $^3$H counts of these 100% survival and 100% death, cell survival rates in the respective wells were calculated, thereby selecting wells high in survival rate.

(7) Cloning

The antibody-producing cells (hybridomas) were separately poured into wells of a 96-well microplate by the limiting dilution technique so as to give a cell concentration of one cell/well to culture each cell. After culturing for 10 days, the proliferation of a single colony could be confirmed. Therefore, the process of detecting the antibody by the blocking of killer activity was performed again. As a result, clones reacting specifically with the Fas ligand were obtained. An antibody was recovered from a culture supernatant containing the hybridoma of a monoclone, thereby obtaining a monoclonal antibody which specifically reacts with the intended Fas ligand.

The thus-obtained hybridoma which produces a monoclonal antibody was named "KAY-10" and deposited as Accession No. FERM BP-5334 in National Institute of Bioscience and Human-Technology, Agency of Industrial Science and Technology.

(8) Preparation of Anti-Mouse Fas Ligand Antibody

The established hybridoma KAY-10, which produces an anti-mouse Fas ligand antibody, were inoculated in a proportion of $1\times10^7$ cells/mouse into 3 ICR nude mice (Charles River Japan Inc.) to which 0.5 ml of pristane had been intraperitoneally administered in advance before a week. After breeding them for about 2 weeks, ascites fluid was collected therefrom. The collected ascites fluid was purified into IgG with Protein G Sepharose.

The purified antibody was designated KAY-10. This antibody was used to conduct the following experiments.

(9) Analysis of Fas Ligand Using Flow Cytometer

As mouse FasL-expressed cell samples, L5178Y cells and BHK cells were used. A method of transfecting a mouse Fas ligand into BHK cells was conducted by the electroporation method like the L5178Y cells.

The following cell samples were used to investigate the reactivity of the KAY-10 antibody.

① BHK cells, ② mouse Fas ligand/BHK cells, ③ L5178Y cells, ④ mouse Fas ligand/L5178Y cells and ⑤ human Fas ligand/L5178Y cells.

These cell samples had been separately cultured in a 10% FCS-RPMI medium containing 10 $\mu$M BB-94 the day before and were collected. Thereafter, these cell samples were separately adjusted to $1\times10^6$ cells/ml with PBS. The thus-adjusted cell samples were separately placed into tubes (Farcon No. 2008) in a proportion of $1\times10^6$ cells/tube (2 tube samples were prepared as to each cell sample). Then, 1 $\mu$g of the KAY-10 antibody was placed in one of two tubes, while 1 $\mu$l of PBS was placed in the other tube as a negative control, thereby conducting a reaction for 30 minutes in a water bath. Each reaction mixture was then centrifugally washed twice with PBS (1,500 rpm, 1 minute, twice) and added with 1 $\mu$l of PE-anti-mouse Ig's (product of Dainippon Pharmaceutical Co., Ltd./Cultag Co.) to further conduct a reaction for 20 minutes on an ice bath. After the reaction, the reaction mixture was centrifugally washed twice with PBS to suspend it in 200 $\mu$l of PBS, followed by measurement by FACScan.

As a result, it was found that the KAY-10 antibody reacts only with the mouse Fas ligand-expressed BHK and L5178Y cells, but not react with their parent strains, BHK and L5178Y cells, and human Fas ligand-expressed L5178Y cells. These results are illustrated in FIGS. 17 to 21.

(10) Analysis with Activated T Cells Derived from Mouse Spleen

The resultant KAY-10 antibody was investigated as to what kinds of mice the antibody reacts with Fas ligands of cell lines derived from.

The spleens were taken out of B6, Balb/c, C3H and DBA mice, minced and then filtered through a mesh, thereby preparing respective cell suspensions. Each of the cell suspensions was adjusted through a nylon wool column in such a manner that T cells were rich. The thus-adjusted cell suspension was cultured at 37° C. for 2 days in a 10% FCS•RPMI medium containing con A (10 μg/ml). After 2 days, the cells were collected by centrifugation and cultured further for 5 days in a 10% FCS•RPMI medium containing 50 U/ml of IL-2. After the cultured cells were collected, they were cultured further for 4 hours on a Petri dish precoated with 10 μg/ml of anti-CD3 antibody. At this time, a 10% FCS•RPMI medium containing 10 μM BB94 was used as a medium. After the cultured cells were collected, FACS analysis was performed in the same manner as in the experiment (9). As a result, as shown in FIGS. 22 to 25, results that the KAY-10 antibody well reacts with the Fas ligands of the cells derived from the B6 mouse and C3H mouse, but weakly or scarcely reacts with the Fas ligands of the cells derived from the DBA mouse and Balb/c mouse were obtained, and so the antibody was found to have species specificity.

The types of MHC class II of the DBA and Balb/c mice are of H-$2^d$, and the type of MHC class II of the MRL gld mouse immunosensitized with the Fas ligand-expressed COS cells for the purpose of providing the KAY-10 antibody is also H-2. On the other hand, the types of MHC class II of the B6 and C3H mice are H-$2^b$ and H-$2^k$, respectively, and different from the type of MHC class II of the MRL gld mouse. This indicates that the anti-mouse Fas ligand antibody according to the present invention does not react with a mouse-derived Fas ligand classified in the same type as the type of MHC class II of a mouse immunosensitized with a Fas ligand for the purpose of providing such an antibody.

(11) Inhibition of Apoptosis Inducibility that Mouse Fas Ligand has, to Fas-Expressed Cells A purified KAY-10 antibody was used to conduct the cytotoxic reaction performed in (6) Sorting of hybridoma. More specifically, mouse Fas ligand/L5178Y cells and human Fas/WR19L were used as effector cells and target cells, respectively, and the antibody KAY-10 was adjusted so as to give a final concentration of 10 μg/ml to investigate the reactivity among them. The result thereof is illustrated in FIG. 26. An axis of ordinate in FIG. 26 indicates in terms of % that how many cells are killed compared with the 100% death and 100% survival (0% death) defined in the step (6) ③ in Example 10. As apparent from FIG. 26, it is understood that apoptosis induction of the Fas ligand against the hFas/WR19L is completely inhibited by adding the antibody.

(12) Investigation as to Inhibition of Apoptosis Induced by Various Th1 Type T Cell Lines with Antibody Various Th1 type cell lines were used as effector cells. More specifically, 129 cell. BK1 cell, POK cell and T16D cell lines were used. These cell lines were activated in advance with 10 mM PMA and 500 nM ionomycin by incubation for 6 hours to use them as effector cells. Thereafter, their assay was performed. As a result, as illustrated in FIG. 27 (an axis of ordinate thereof has the same meaning as in FIG. 26), it was found that the KAY-10 antibody inhibits apoptosis induction activities that these Th1 clones have, depending on its concentration. The antibody had no effect only on the BK1 cell line. Since the BK1 cell line is a Th1 cell strain derived from a Ba/b/c mouse, however, this consist with the result of the FACS analysis described above. Namely, the KAY-10 antibody does not react with the Fas ligand of Balb/c.

Example 11

1. A peptide library was constructed by synthesizing 44 kinds of 10-mer peptides with amino acid units shifted by 4mers, such as a peptide of 10mers from the N-terminal of an extracellular domain of the Fas ligand, a peptide of 10mers from the 5th to the 14th, a peptide of 10mers from the 9th to the 19th and a peptide of 10mers from the 13th to the 22th. (PEPSET (trade mark, product of Chylone Co.) was used).

2. A culture supernatant of the NOK2 hybridoma was used to specifying the site of the Fas ligand with which the anti-Fas ligand antibody reacts.

① Each well of a 96-well plate (MAXISORP, trade mark, product of Nunc Co.) was filled with a blocking solution [Block Ace (product of Dainippon Pharmaceutical), diluted to ¼ with distilled water], and a pin (one of the synthesized peptides was immobilized on a tip thereof) of the Pepset was inserted into the well to block the tip of the pin for 2 hours at room temperature.

② After completion of the blocking, the pin of the Pepset was taken out of the well and washed with PBS.

③ The culture supernatant of the hybridoma NOK2 was poured in portions of 100 μl/well into wells of a new 96-well plate. As a control, an antibody solution accessory to the Pepset was used (the Pepset is provided with a pin for a positive control, a pin for a negative control and antibody solutions against them).

④ Thereafter, the pin of the Pepset was inserted into each well of the plate described in the step ③ to conduct a reaction for 2 hours at room temperature.

⑤ The pin of the Pepset was taken out of the well of the plate described in the step ④ and transferred to a pad containing PBS to conduct shake-washing 3 times for 10 minutes.

⑥ An HRP (horseradish peroxidase)-labeled anti-mouse IgG (product of Cappel Co.) diluted to ¹⁄₁,₀₀₀ with PBS was poured in portions of 100 μl/well into wells of a new 96-well plate. The pin of the Pepset was inserted into each of the wells of this plate to conduct a reaction for 2 hours at room temperature.

⑦ After the reaction, the pin of Pepset was taken out of the well and shake-washed 3 times with PBS for 10 minutes.

⑧ A liquid substrate having the following composition was poured in portions of 100 μl/well into wells of a new 96-well plate. The pin of the Pepset was inserted into each of the wells of this plate to conduct a reaction for 2 hours at room temperature.

Composition of the Liquid Substrate:
OPD 0.4 mg/ml, 30% $H_2O_2$ 0.4 μl/ml, 0.1 M citric acid-phosphate buffer (pH 5.1).

⑨ After the pin of the Pepset was taken out of the well of the plate, 2N $H_2SO_4$ was added in an amount of 50 μl to each well to stop the reaction.

⑩ The absorbance of the liquid contained in each well of this plate was measured by a plate reader (manufactured by Bio-Rad Co.).

⑪ As a result, with respect to the culture supernatant of the hybridoma NOK2, a color change due to the enzymatic reaction of HRP bound to the peptide immobilized on the pin was observed in wells into which pins on which peptides of consisting of residues 1 to 10 and residues 5 to 14 of SEQ ID NO: 31 had been separately immobilized, were separately inserted. Namely, it was found that the anti-Fas ligand antibody produced by the hybridoma NOK2 recognizes the region, LSHKVYMRNSKYPQ (SEQ ID NO: 31), of the Fas ligand.

INDUSTRIAL APPLICABILITY

Since the monoclonal antibodies against Fas ligand according to the present invention specifically react with a Fas ligand, they can serve to elucidate signal transfer mechanism for inducing apoptosis against cells, and a Fas system, for example, by analyzing the interaction between a Fas antigen and its ligand.

The monoclonal antibodies against Fas ligand according to the present invention are useful in immunothearpy and immunodiagnoses, and industrial fields associated with them. More specifically, the monoclonal antibody against Fas ligand is reacted with cells in blood, and a secondary antibody of a fluorescent marker is further bound thereto to measure the conjugate by flow cytometry or a fluorescent microscope, thereby being able to confirm that the Fas ligand has expressed in what cells. The monoclonal antibody against Fas ligand can be easily bound to a fluorochrome such as FITC or PE. Accordingly, analysis can be conducted without using any secondary antibody. The concentration of a Fas ligand can be detected by using a plurality of the monoclonal antibodies in combination. Therefore, the monoclonal antibodies according to the present invention are very useful in fields of diagnoses and fundamental researches.

When the monoclonal antibody according to the present invention is reacted with tissues and the like taken out of a patient suffered from various diseases (for example, an autoimmune disease, rheumatism and hepatitis), what tissue Fas ligand-expressed cells exist in can be determined. This permits the diagnoses and treatments of the various diseases. Since the monoclonal antibodies against Fas ligand inhibit the reaction (binding) of a Fas ligand, they are useful in treating diseases such as AIDS, rheumatism and hepatitis. When an antibody-producing gene is synthesized from the monoclonal antibody according to the present invention, and only a region related to binding with a Fas ligand is transplanted into a human IgG antibody, a humanized antibody can be obtained. The humanized antibody is useful in treating the many diseases described above.

Since the monoclonal antibodies according to the present invention also react with monkey Fas ligand, they are useful in investigating antibodies for treating various diseases including AIDS and viral hepatitis. In addition, they are very useful in screening new remedies because their effects can be monitored. In many cases, experimental systems in mice as to, in particular, virus-infected diseases and the like can not be constructed. Therefore, the fact that the monoclonal antibodies according to the present invention react with human and monkey Fas ligands has great merit.

In addition, the fact that the monoclonal antibodies against human Fas ligand do not react with a mouse Fas ligand serves for investigation with SCID mice and the like. In addition, they are also useful in specifically inhibiting or monitoring the action and the like after human cells are transplanted into a mouse.

International Depositary Institution

Hybridomas NOK1 to NOK5 and KAY-10 are deposited in the following international depositary institution with the following respective accession numbers and deposition dates.

Name: National Institute of Bioscience and Human-Technology, Agency of Industrial Science and Technology, Ministry of International Trade and Industry.

Address: 1–3, Higashi 1-chome, Tsukuba-shi, Ibaraki-ken 305, Japan.

Accession number and deposition date:

① Hybridoma NOK1
FERM BP-5044; Mar. 20, 1995
② Hybridoma NOK2
FERM BP-5045; Mar. 20, 1995
③ Hybridoma NOK3
FERM BP-5046; Mar. 20, 1995
④ Hybridoma NOK4
FERM BP-5047; Mar. 20, 1995
⑤ Hybridoma NOK5
FERM BP-5048; Mar. 20, 1995
⑥ Hybridoma KAY-19
FERM BP-5334; Dec. 14, 1995

---

What is claimed is:

1. A monoclonal antibody or active fragment of the monoclonal antibody that specifically reacts with a human or a mouse FAS ligand, wherein the antibody is produced by any one of hybridoma cell lines deposited as Accession Nos. FERM BP-5044 (Hybridoma NOK1), FERM BP-5045 (Hybridoma NOK 2), FERM BP-5046 (Hybridoma NOK3), FERM BP-5047 (Hybridoma NOK 4), FERM BP-5048 (Hybridoma NOK5) and FERM BP-5334 (Hybridoma KAY-10) in National Institute of Bioscience and Hyman-Technology, Agency of Industrial Science and Technology, wherein the active fragment is F(ab')$_2$, Fab', Fab, Fv or recombinant Fv, and wherein the antibody produced by any one of the hybridoma cell lines deposited as Accession Nos. FERM BP-5044 (Hybridoma NOK1), FERM BP-5045 (Hybridoma NOK 2), FERM BP-5046 (Hybridoma NOK3), FERM BP-5047 (Hybridoma NOK 4) and FERM BP-5048 (Hybridoma NOK5) or active fragment of the monoclonal antibody reacts specifically with a human Fas ligand, and said antibody or fragment thereof inhibits apoptosis more than a control FAS-Ig chimera at a concentration of 0.01–8 µg/ml, and further wherein the antibody produced by the hybridoma cell line deposited as Accession No. FERM BP-5334 (Hybridoma KAY-10) or active fragment of the monoclonal antibody reacts specifically with the Fas ligands of cells derived from the B6 mouse and C3H mouse.

2. The monoclonal antibody or active fragment of the monoclonal antibody according to claim 1, wherein the antibody produced by any one of the hybridoma cell lines deposited as Accession Nos. FERM BP-5044 (Hybridoma NOK1), FERM BP-5045 (Hybridoma NOK 2), FERM BP-5046 (Hybridoma NOK3), FERM BP-5047 (Hybridoma NOK 4) and FERM BP-5048 (Hybridoma NOK5) can inhibit the apoptosis of Fas-expressed cells induced by a soluble human Fas ligand at an apoptosis inhibition rate of at least 90%, said apoptosis inhibition rate meaning a survival rate of target cells, to which an antibody has been added, in a cytotoxic reaction test in which a soluble human Fas ligand contained in a 12-fold dilution of a culture supernatant of Fas ligand gene-transsfected cells are used as an effector molecule, and Fas gene-transfected cells are used as target cells, and both are reacted in a reaction system of 100 µl in a 96-well plate to determine the survival rate of the target cells after 16 hours using a reagent for detecting viable cell numbers.

3. The monoclonal antibody or active fragment of the monoclonal antibody according to claim 2, wherein the survival rate of the target cells can be enhanced to at least 90% when the soluble human Fas ligand contained in the 12-fold dilution of the culture supernatant of the Fas ligand gene-transfected cells is used as the effector molecule in an amount of 25 µl in terms of such a dilution, the Fas gene-transfected cells (Fas/WR19L) are used as the target cells in an amount of 50 µl in terms of its solution at a concentration of $2\times10^5$ cells/ml, and a culture supernatant of the hybridoma containing said monoclonal antibody is used in an amount of 25 µl to mix all these components with one another, thereby conducting a reaction at 37° C. for 16 hours.

4. The monoclonal antibody or active fragment of the monoclonal antibody according to claim 1, wherein the antibody produced by any one of hybridoma cell lines deposited as Accession Nos. FERM BP-5044 (Hybridoma NOK1), FERM BP-5045 (Hybridoma NOK 2), FERM BP-5046 (Hybridoma NOK3), FERM BP-5047 (Hybridoma NOK 4) and FERM BP-5048 (Hybridoma NOK5) can inhibit a physiological reaction of a human Fas ligand and Fas, but not inhibit a physiological reaction of a mouse Fas ligand.

5. The monoclonal antibody or active fragment of the monoclonal antibody according to claim 1, wherein the antibody or active fragment can affinity-purify a human or mouse Fas ligand present in a culture supernatant of Fas ligand-expressed cells.

6. The monoclonal antibody or active fragment of the monoclonal antibody according to claim 1, wherein the antibody or active fragment can immunoprecipitate Fas ligand molecules on Fas ligand-expressed cell surfaces or soluble Fas ligand molecules secreted in a culture solution.

7. A method of detecting a human or mouse Fas ligand in a solution, which comprises combining a plurality of monoclonal antibodies against Fas ligand according to claim 1.

8. The detection method according to claim 7, wherein one of the monoclonal antibodies is immobilized on a carrier, another monoclonal antibody is labeled with a labeled compound, the carrier on which the monoclonal antibody has been immobilized is brought into contact with a solution of a specimen which is considered to contain a human or mouse Fas ligand, thereby adsorbing the specimen, and the adsorbed specimen is detected by the monoclonal antibody labeled with the labeled compound.

9. The detection method according to claim 8, wherein a monoclonal antibody of IgM type is immobilized on a carrier, and a human or mouse Fas ligand in a solution is detected by a biotin-labeled monoclonal antibody of IgG type.

10. A kit for use in detecting a human or mouse Fas ligand, comprising in combination a plurality of monoclonal antibodies against Fas ligand according to claim 1.

11. The monoclonal antibody or active fragment of the monoclonal antibody according to claim 1, wherein the antibody or active fragment can affinity-purify a soluble human or mouse Fas ligand present in a culture supernatant of human or mouse Fas ligand-expressed cells.

12. A monoclonal antibody which specifically reacts with a human or mouse Fas ligand, or an active fragment of the monoclonal antibody according to claim 1, wherein the antibody is produced by a process comprising the steps of (1) immunosensitizing an animal, which does not express a functional Fas molecule, with a Fas ligand human or mouse Fas ligand molecule or Fas ligand-expressing cells, (2) and selecting the hybridoma that produced the monoclonal antibody according to claim 1.

13. The monoclonal antibody or the active fragment thereof of the monoclonal antibody according to claim 12, wherein the animal is a rodent belonging to MRL 1 pr/1pr mice.

14. The monoclonal antibody or the active fragment thereof of the monoclonal antibody according to claim 12, wherein the animal is a rodent belonging to MRL gld mice.

15. A process for producing monoclonal antibodies specifically reacting with a human or mouse FAS ligand according to claim 1, which comprises the steps of (1) immunosensitizing a rodent, which does not express a functional Fas molecule, with a Fas ligand human or mouse molecule or Fas ligand-expressing cells, (2) preparing antibody-producing cells from the immunosensitized animal to form a suspension of the antibody-producing cells, (3) mixing the suspension of the antibody-producing cells with myeloma cells to fuse both cells, (4) diluting the fused cells with a medium that does not favor unfused myeloma cells so that the fused cells are cultured, thereby sorting hybridomas produced by the fusion of the antibody-producing cells with the myeloma cells, (5) determining whether antibodies secreted in a culture supernatant containing the hybridomas are against the desired human or mouse Fas ligand antigen, (6) cloning a series of cells in culture wells in which cells secreting the desired antibodies exist, (7) selecting a clone from which the desired antibody is secreted, (8) establishing hybridoma clone which secretes the monoclonal antibody against the Fas ligand antigen, and (9) purifying the monoclonal antibody from a culture supernatant of the hybridoma or ascites fluid obtained by intraperitoneally administering the hybridoma to a mouse.

\* \* \* \* \*

UNITED STATES PATENT AND TRADEMARK OFFICE
CERTIFICATE OF CORRECTION

PATENT NO. : 6,946,255 B1
DATED : September 20, 2005
INVENTOR(S) : Nobuhiko Kayagaki et al.

It is certified that error appears in the above-identified patent and that said Letters Patent is hereby corrected as shown below:

Title page,
Item [54], Title, change "MONOCLONAL ANTIBODY REACTING SPECIFICALLY REACTING WITH FAX LIGAND AND PRODUCTION PROCESS THEREOF" to -- MONOCLONAL ANTIBODY SPECIFICALLY REACTING WITH FAX LIGAND AND PRODUCTION PROCESS THEREOF --.
Item [86], PCT No., after "(2), (4) Date:", change "Sep. 17, 1997" to -- Sep. 19, 1997 --.

Signed and Sealed this

Twenty-seventh Day of December, 2005

JON W. DUDAS
*Director of the United States Patent and Trademark Office*